(12) United States Patent
Meduna et al.

(10) Patent No.: US 8,775,128 B2
(45) Date of Patent: Jul. 8, 2014

(54) SELECTING FEATURE TYPES TO EXTRACT BASED ON PRE-CLASSIFICATION OF SENSOR MEASUREMENTS

(71) Applicant: Sensor Platforms, Inc., San Jose, CA (US)

(72) Inventors: Deborah Meduna, San Francisco, CA (US); Tom Waite, El Sobrante, CA (US); Dev Rajnarayan, Mountain View, CA (US)

(73) Assignee: Sensor Platforms, Inc., San Jose, CA (US)

( * ) Notice: Subject to any disclaimer, the term of this patent is extended or adjusted under 35 U.S.C. 154(b) by 0 days.

(21) Appl. No.: 13/939,126

(22) Filed: Jul. 10, 2013

(65) Prior Publication Data

US 2014/0129178 A1    May 8, 2014

Related U.S. Application Data

(60) Provisional application No. 61/794,032, filed on Mar. 15, 2013, provisional application No. 61/723,744, filed on Nov. 7, 2012.

(51) Int. Cl.
   *G21C 17/00* (2006.01)
   *G06F 17/40* (2006.01)

(52) U.S. Cl.
   USPC ........... 702/189; 702/179; 702/182; 702/183; 702/187

(58) Field of Classification Search
   USPC .......................... 702/179, 182, 183, 187–189
   See application file for complete search history.

(56) References Cited

U.S. PATENT DOCUMENTS

| 7,028,547 | B2 * | 4/2006 | Shiratori et al. | 73/495 |
| 2010/0134241 | A1 * | 6/2010 | Gips et al. | 340/5.1 |
| 2010/0174506 | A1 | 7/2010 | Joseph et al. | |
| 2012/0265716 | A1 * | 10/2012 | Hunzinger et al. | 706/12 |

OTHER PUBLICATIONS

Hjorth, Technical Contributions, EEG Analysis Based on Time Domain Properties, Research and Development Laboratory, Solna, Sweden, Jan. 30, 1970, 5 pgs.
Hjorth, Technical Contributions, The Physical Significance of Time Domain Descriptors in EEG Analysis, Research and Development Labaoratory, Solna, Sweden, Aug. 10, 1972, 5 pgs.
Hjorth, Technical Contributions, An On-line Transformation of EEG Scalp Potentials Into Orthogonal Source Derivations, Research and Development Laboratory, Solna, Sweden, Jul. 1, 1975, 5 pgs.
Jimenez, A Comparison of Pedestrian Dead-Reckoning Algorithms Using a Low-Cost MEMS IMU, 6th International Symposium on Intelligent Signal Processing, Aug. 26-28, 2009, 6 pgs.

* cited by examiner

*Primary Examiner* — Janet Suglo
(74) *Attorney, Agent, or Firm* — Morgan, Lewis & Bockius LLP

(57) ABSTRACT

A processing apparatus including one or more processors and memory receives sensor measurements generated by one or more sensors of one or more devices, pre-classifies the sensor measurements as belonging to one of a plurality of pre-classifications, and selects one or more feature types to extract from the sensor measurements based at least in part on the pre-classification of the sensor measurements. The processing apparatus also extracts features of the one or more selected feature types from the sensor measurements and determines a state of a respective device of the one or more devices in accordance with a classification of the sensor measurements determined based on the one or more features extracted from the sensor measurements.

159 Claims, 18 Drawing Sheets

SELECTING FEATURE TYPES TO EXTRACT BASED ON PRE-CLASSIFICATION OF SENSOR MEASUREMENTS

RELATED APPLICATIONS

This application claims priority to U.S. Provisional Patent Application Ser. No. 61/794,032, filed Mar. 15, 2013, entitled "Selecting Feature Types to Extract Based on Pre-Classification of Sensor Measurements" and U.S. Provisional Patent Application Ser. No. 61/723,744, filed Nov. 7, 2012, entitled Selecting Feature Types to Extract Based on Pre-Classification of Sensor Measurements," which applications are incorporated by reference herein in their entirety.

TECHNICAL FIELD

The disclosed embodiments relate generally to determining a state associated with a device in accordance with a classification of sensor measurements associated with the device.

BACKGROUND

Devices have access to sensor measurements from one or more sensors. These sensor measurements can be used to determine information about states associated with the device such as a coupling state of the device to one or more entities, a state of one or more entities physically associated with the device and/or a state of an environment in which the device is located.

SUMMARY

As the number of sensor measurements available to the device increases, the task of selecting appropriate sensor measurements and analyzing the sensor measurements to determine information about states associated with the device becomes increasingly complicated. The increasing complexity of this task can negatively impact both device performance and energy efficiency of the device. As such, it would be advantageous to find ways to reduce the processing cost and/or increase the energy efficiency of determining a state associated with a device while maintaining the accuracy of the determination. One approach to improving the efficiency of determining a state associated with a device is to use one or more pre-classifications of sensor measurements to determine which features to extract from sensor measurements available to the device. Thus, the device can forgo extracting features that are not likely to be useful for determining a current state of the device while extracting features that are likely to be useful for determining the current state of the device.

Some embodiments provide a method for determining a state associated with a device at a processing apparatus having one or more processors and memory storing one or more programs that, when executed by the one or more processors, cause the respective processing apparatus to perform the method. The method includes receiving sensor measurements generated by one or more sensors of one or more devices, pre-classifying the sensor measurements as belonging to one of a plurality of pre-classifications, and selecting one or more feature types to extract from the sensor measurements based at least in part on the pre-classification of the sensor measurements. The method further includes extracting features of the one or more selected feature types from the sensor measurements and determining a state of a respective device of the one or more devices in accordance with a classification of the sensor measurements determined based on the one or more features extracted from the sensor measurements.

In accordance with some embodiments, a computer system (e.g., a navigation sensing device or a host computer system) includes one or more processors, memory, and one or more programs; the one or more programs are stored in the memory and configured to be executed by the one or more processors and the one or more programs include instructions for performing the operations of any of the methods described above. In accordance with some embodiments, a non-transitory computer readable storage medium (e.g., for use by a navigation sensing device or a host computer system) has stored therein instructions which when executed by one or more processors, cause a computer system (e.g., a navigation sensing device or a host computer system) to perform the operations of any of the methods described above.

BRIEF DESCRIPTION OF THE DRAWINGS

Like reference numerals refer to corresponding parts throughout the drawings.

DESCRIPTION OF EMBODIMENTS

Exemplary Use Cases

Figure 1:
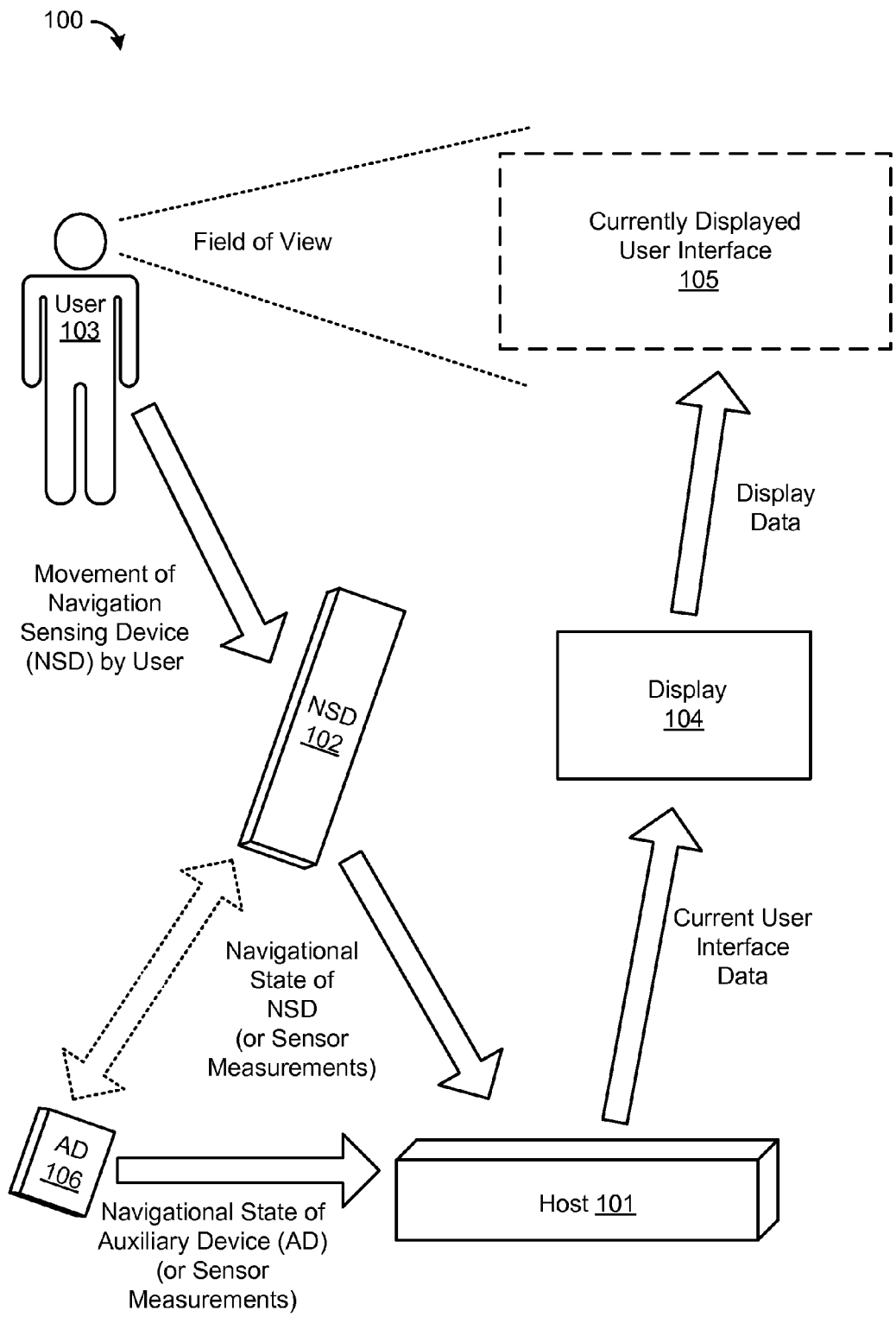
FIG. 1 illustrates a system for using a navigation sensing device, according to some embodiments.

Navigation sensing devices (e.g., human interface devices or motion tracking device) that have a determinable multi-dimensional navigational state (e.g., one or more dimensions of displacement and/or one or more dimensions of rotation or attitude) are becoming increasingly common for providing input for many different applications. For example, such a navigation sensing device may be used as a motion tracking device to track changes in position and/or orientation of the device over time. These tracked changes can be used to map movements and/or provide other navigational state dependent services (e.g., location or orientation based alerts, etc.). In some situations, pedestrian dead reckoning (PDR) is used to determine changes in position of an entity that is physically associated with a device (e.g., by combining direction of motion information for the entity with stride count and stride length information). However, in circumstances where the physical coupling between the navigation sensing device and the entity is variable, the navigation sensing device uses sensor measurements to determine both changes in the physical coupling between the navigation sensing device and the entity (e.g., a "device-to-entity orientation") and changes in direction of motion of the entity.

As another example, such a navigation sensing device may be used as a multi-dimensional pointer to control a pointer (e.g., a cursor) on a display of a personal computer, television, gaming system, etc. As yet another example, such a navigation sensing device may be used to provide augmented reality views (e.g., by overlaying computer generated elements over a display of a view of the real world) that change in accordance with the navigational state of the navigation sensing device so as to match up with a view of the real world that is detected on a camera attached to the navigation sensing device. In other situations, such a navigation sensing device may be used to provide views of a virtual world (e.g., views of portions of a video game, computer generated simulation, etc.) that change in accordance with the navigational state of the navigation sensing device so as to match up with a virtual viewpoint of the user based on the orientation of the device. In this document, the terms orientation, attitude and rotation are used interchangeably to refer to the orientation of a device or object with respect to a frame of reference. Additionally, a single navigation sensing device is optionally capable of performing multiple different navigation sensing tasks described above either simultaneously or in sequence (e.g., switching between a multi-dimensional pointer mode and a pedestrian dead reckoning mode based on user input).

In order to function properly (e.g., return results to the user that correspond to movements of the navigation sensing device in predictable ways), these applications rely on sensors that determine accurate estimates of the current state(s) associated with the device (e.g., a navigational state of the device, a user-device coupling state, a state of a user physically associated with the device and/or a state of an environment of the device). While specific use cases are described above and will be used to illustrate the general concepts described herein, it should be understood that these examples are non-limiting examples and that the embodiments described herein would apply in an analogous manner to any device that would benefit from an accurate estimate of the current state(s) associated with the device (e.g., a navigational state of the device, a user-device coupling state, a state of a user who is physically associated with the device and/or a state of an environment of the device).

System Overview

Attention is now directed to FIG. 1, which illustrates an example system 100 for using a navigation sensing device (e.g., a human interface device such as a multi-dimensional pointer) to manipulate a user interface. As shown in FIG. 1, an example Navigation Sensing Device 102 (hereinafter "Device 102") is coupled to a Host Computer System 101 (hereinafter "Host 101") through a wireless interface, according to some embodiments. In these embodiments, a User 103 moves Device 102. These movements are detected by sensors in Device 102, as described in greater detail below with reference to FIG. 2. Device 102, or Host 101, generates a navigational state of Device 102 based on sensor measurements from the sensors and transmits the navigational state to Host 101. Alternatively, Device 102 generates sensor measurements and transmits the sensor measurements to Host 101, for use in estimating a navigational state of Device 102. Host 101 generates current user interface data based on the navigational state of Device 102 and transmits the current user interface data to Display 104 (e.g., a display or a projector), which generates display data that is displayed to the user as the currently displayed User Interface 105. While Device 102, Host 101 and Display 104 are shown in FIG. 1 as being separate, in some embodiments the functions of one or more of these elements are combined or rearranged, as described in greater detail below with reference to FIGS. 3A-3E.

In some embodiments, an Auxiliary Device 106 also generates sensor measurements from one or more sensors and transmits information based on the sensor measurements (e.g., raw sensor measurements, filtered signals generated based on the sensor measurements or other device state information such as a coupling state of Auxiliary Device 106 or a navigational state of Auxiliary Device 106) to Device 102 and/or Host 101 via wired or wireless interface, for use in determining a state of Device 102. It should be understood that Auxiliary Device 106 optionally has one or more of the features, components, or functions of Navigation Sensing Device 102, but those details are not repeated here for brevity.

In some implementations, the user can use Device 102 to issue commands for modifying the user interface, control objects in the user interface, and/or position objects in the user interface by moving Device 102 so as to change its navigational state. In some embodiments, Device 102 is sensitive to six degrees of freedom: displacement along the x-axis, displacement along the y-axis, displacement along the z-axis, yaw, pitch, and roll. In some other situations, Device 102 is a navigational state tracking device (e.g., a motion tracking device) that tracks changes in the navigational state of Device 102 over time but does not use these changes to directly update a user interface that is displayed to the user. For example, the updates in the navigational state can be recorded for later use by the user or transmitted to another user or can be used to track movement of the device and provide feedback to the user concerning their movement (e.g., directions to a particular location near the user based on an estimated location of the user). When used to track movements of a user without relying on external location information (e.g., Global Positioning System signals), such motion tracking devices are also sometimes referred to as pedestrian dead reckoning devices.

In some embodiments, the wireless interface is selected from the group consisting of: a Wi-Fi interface, a Bluetooth interface, an infrared interface, an audio interface, a visible light interface, a radio frequency (RF) interface, and any combination of the aforementioned wireless interfaces. In some embodiments, the wireless interface is a unidirectional wireless interface from Device 102 to Host 101. In some embodiments, the wireless interface is a bidirectional wireless interface. In some embodiments, bidirectional communication is used to perform handshaking and pairing operations. In some embodiments, a wired interface is used instead of or in addition to a wireless interface. As with the wireless interface, the wired interface is, optionally, a unidirectional or bidirectional wired interface.

In some embodiments, data corresponding to a navigational state of Device 102 (e.g., raw measurements, calculated attitude, correction factors, position information, etc.) is transmitted from Device 102 and received and processed on Host 101 (e.g., by a host side device driver). Host 101 uses this data to generate current user interface data (e.g., specifying a position of a cursor and/or other objects in a user interface) or tracking information.

Figure 2:
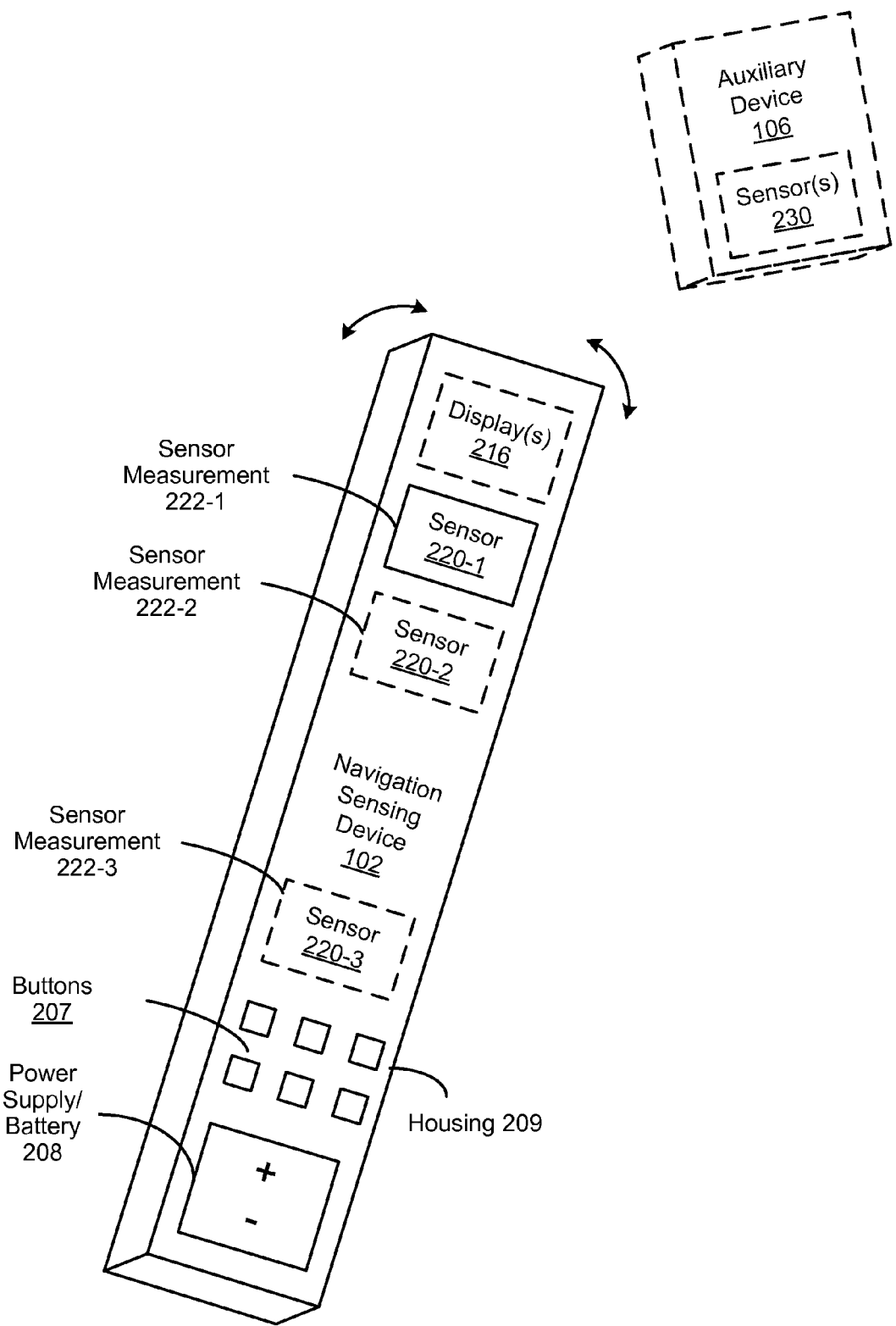
FIG. 2 is a block diagram illustrating an example navigation sensing device and auxiliary device, according to some embodiments.

Attention is now directed to FIG. 2, which illustrates an example of Device 102 and Auxiliary Device 106, according to some embodiments. In accordance with some embodiments, Device 102 includes one or more Sensors 220 which produce corresponding sensor outputs, which can be used to determine a state associated with Device 102 (e.g., a navigational state of the device, a user-device coupling state, a state of a user physically associated with the device and/or a state of an environment of the device). For example, in one implementation, Sensor 220-1 is a multi-dimensional magnetometer generating multi-dimensional magnetometer measurements (e.g., a rotation measurement), Sensor 220-2 is a multi-dimensional accelerometer generating multi-dimensional accelerometer measurements (e.g., a rotation and translation measurement), and Sensor 220-3 is a gyroscope generating measurements (e.g., either a rotational vector measurement or rotational rate vector measurement) corresponding to changes in orientation of the device. In some implementations Sensors 220 include one or more of gyroscopes, beacon sensors, inertial measurement units, temperature sensors, barometers, proximity sensors, single-dimensional accelerometers and multi-dimensional accelerometers instead of or in addition to the multi-dimensional magnetometer and multi-dimensional accelerometer and gyroscope described above. In accordance with some embodiments, Auxiliary Device 106 includes one or more Sensors 230 which produce corresponding sensor outputs, which can be used to determine a state associated with Auxiliary Device 106 (e.g., a navigational state of the device, a user-device coupling state, a state of a user physically associated with the device and/or a state of an environment of the device). In some implementations, information corresponding to the sensor outputs of Sensors 230 of Auxiliary Device 106 is transmitted to Device 102 for use in determining a state of Device 102. Similarly, in some implementations, information corresponding to the sensor outputs of Sensors 220 of Device 102 is transmitted to Auxiliary Device 106 for use in determining a state of Auxiliary Device 106. For example Device 102 is a phone and Auxiliary Device 106 is a Bluetooth headset that is paired with the phone, and the phone and the Bluetooth headset share information based on sensor measurements to more accurately determine a state of Device 102 and/or Auxiliary Device 106. As another example two mobile phones near each other can be configured to share information about their environmental context and/or their position. Additionally, a wrist watch with an accelerometer can be configured to share accelerometer measurements and/or derived posture information with a mobile phone held by the user to improve posture estimates for the user.

In some embodiments, Device 102 also includes one or more of: Buttons 207, Power Supply/Battery 208, Camera 214 and/or Display 216 (e.g., a display or projector). In some embodiments, Device 102 also includes one or more of the following additional user interface components: one or more processors, memory, a keypad, one or more thumb wheels, one or more light-emitting diodes (LEDs), an audio speaker, an audio microphone, a liquid crystal display (LCD), etc. In some embodiments, the various components of Device 102 (e.g., Sensors 220, Buttons 207, Power Supply 208, Camera 214 and Display 216) are all enclosed in Housing 209 of Device 102. However, in implementations where Device 102 is a pedestrian dead reckoning device, many of these features are not necessary, and Device 102 can use Sensors 220 to generate tracking information corresponding changes in navigational state of Device 102 and transmit the tracking information to Host 101 wirelessly or store the tracking information for later transmission (e.g., via a wired or wireless data connection) to Host 101.

In some embodiments, one or more processors (e.g., 1102, FIG. 6) of Device 102 perform one or more of the following operations: sampling Sensor Measurements 222, at a respective sampling rate, produced by Sensors 220; processing sampled data to determine displacement; transmitting displacement information to Host 101; monitoring the battery voltage and alerting Host 101 when the charge of Battery 208 is low; monitoring other user input devices (e.g., keypads, buttons, etc.), if any, on Device 102 and, as appropriate, transmitting information identifying user input device events (e.g., button presses) to Host 101; continuously or periodically running background processes to maintain or update calibration of Sensors 220; providing feedback to the user as needed on the remote (e.g., via LEDs, etc.); and recognizing gestures performed by user movement of Device 102.

Attention is now directed to FIGS. 3A-3E, which illustrate configurations of various components of the system for generating navigational state estimates for a navigation sensing device. In some embodiments, there are three fundamental components to the system for determining a navigational state of a navigation sensing device described herein: Sensors 220, which provide sensor measurements that are used to determine a navigational state of Device 102, Measurement Processing Module 322 (e.g., a processing apparatus including one or more processors and memory) which uses the sensor measurements generated by one or more of Sensors 220 to generate estimates of the navigational state of Device 102 which can be used to determine current user interface data and/or track movement of Device 102 over time (e.g., using pedestrian dead reckoning), and, optionally, Display 104, which displays the currently displayed user interface to the user of Device 102 and/or information corresponding to movement of Device 102 over time. It should be understood that these components can be distributed among any number of different devices.

In some embodiments, Measurement Processing Module 322 (e.g., a processing apparatus including one or more processors and memory) is a component of the device including Sensors 220. In some embodiments, Measurement Processing Module 322 (e.g., a processing apparatus including one or more processors and memory) is a component of a computer system that is distinct from the device including Sensors 220. In some embodiments a first portion of the functions of Measurement Processing Module 322 are performed by a first device (e.g., raw sensor data is converted into processed sensor data at Device 102) and a second portion of the functions of Measurement Processing Module 322 are performed by a second device (e.g., processed sensor data is used to generate a navigational state estimate for Device 102 at Host 101).

Figure 3A:
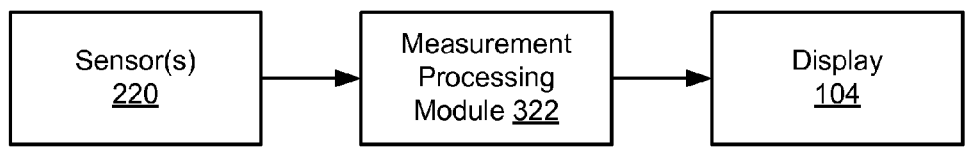
FIGS. 3A-3E are block diagrams illustrating configurations of various components of the system including a navigation sensing device, according to some embodiments.
Figure 3B:
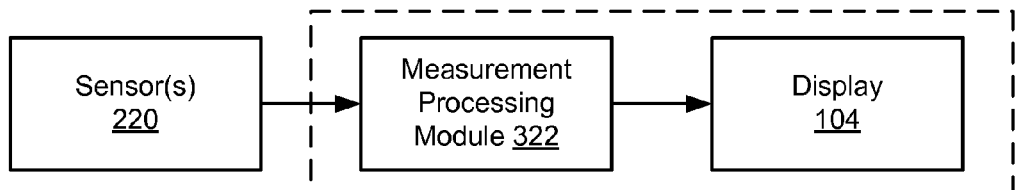
Figure 3C:
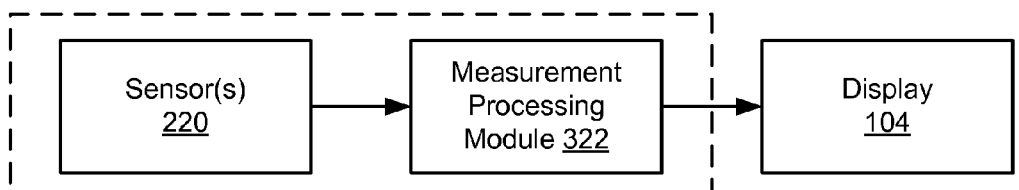

As one example, in FIG. 3A, Sensors 220, Measurement Processing Module 322 and Display 104 are distributed between three different devices (e.g., a navigation sensing device such as a multi-dimensional pointer, a set top box, and a television, respectively; or a motion tracking device, a back-end motion processing server and a motion tracking client). As another example, in FIG. 3B, Sensors 220 are included in a first device (e.g., a multi-dimensional pointer or a pedestrian dead reckoning device), while the Measurement Processing Module 322 and Display 104 are included in a second device (e.g., a host with an integrated display). As another example, in FIG. 3C, Sensors 220 and Measurement Processing Module 322 are included in a first device, while Display 104 is included in a second device (e.g., a "smart" multi-dimensional pointer and a television respectively; or a motion tracking device such as a pedestrian dead reckoning device and a display for displaying information corresponding to changes in the movement of the motion tracking device over time, respectively).

Figure 3D:
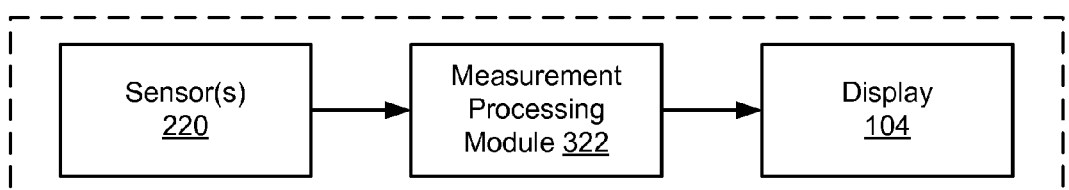
Figure 3E:
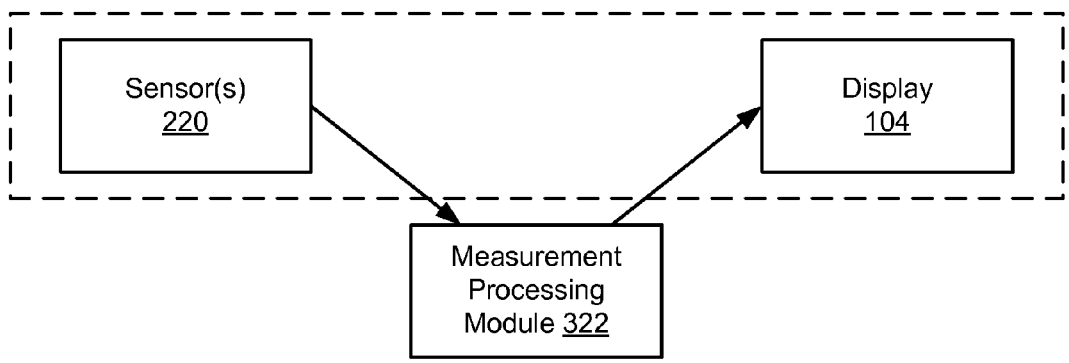

As yet another example, in FIG. 3D, Sensors 220, Measurement Processing Module 322 and Display 104 are included in a single device (e.g., a mobile computing device, such as a smart phone, personal digital assistant, tablet computer, pedestrian dead reckoning device etc.). As a final example, in FIG. 3E, Sensors 220 and Display 104 are included in a first device (e.g., a game controller with a display/projector), while Measurement Processing Module 322 is included in a second device (e.g., a game console/server). It should be understood that in the example shown in FIG. 3E, the first device will typically be a portable device (e.g., a smart phone or a pointing device) with limited processing power, while the second device is a device (e.g., a host computer system) with the capability to perform more complex processing operations, or to perform processing operations at greater speed, and thus the computationally intensive calculations are offloaded from the portable device to a host device with greater processing power. While a plurality of common examples have been described above, it should be understood that the embodiments described herein are not limited to the examples described above, and other distributions of the various components could be made without departing from the scope of the described embodiments.

Determining a State Associated with a Device

Attention is now directed to FIGS. 4A-4D, which include block diagrams illustrating an example of determining a state associated with a device, in accordance with some embodiments.

Figure 4A:
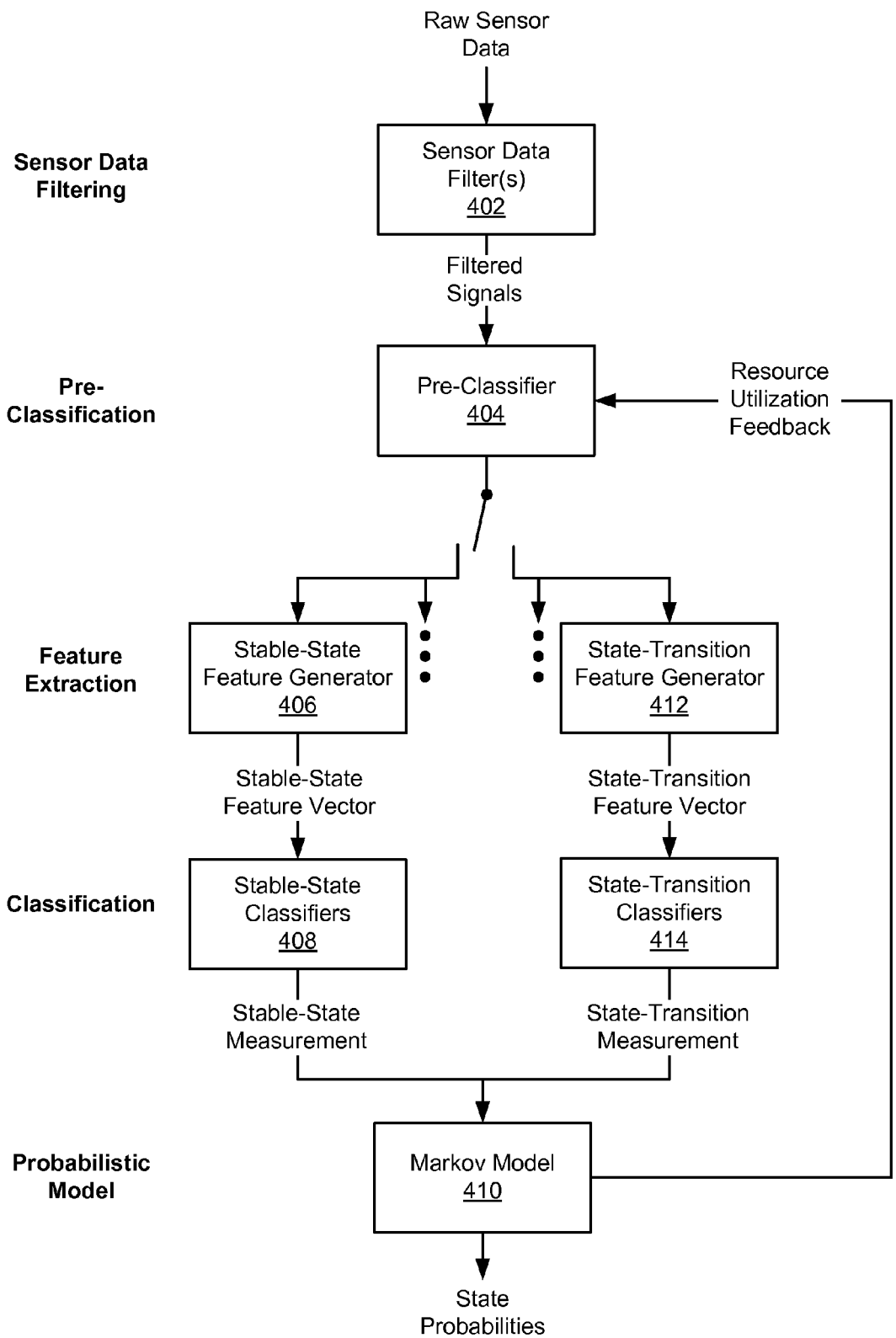
FIG. 4A-4D are diagrams illustrating an example of determining a state associated with a device, according to some embodiments.

The implementation of determining a state associated with a device described below with reference to FIGS. 4A-4D is explained with reference to a particular example of determining a coupling state of a device (e.g., determining if and how a device is associated with an entity). However, it should be understood that the general principles described below are applicable to a variety of different states associated with a device (e.g., a navigational state of the device, a state of a user physically associated with the device and/or a state of an environment of the device). FIG. 4A illustrates an overview of a method of determining probabilities of a state associated with the device based on raw sensor data. During a sensor data filtering stage, raw sensor data is converted into filtered signals by one or more Sensor Data Filters 402. During a pre-classification stage, a pre-classification of the state is determined by Pre-Classifier 404 based on the filtered signals, so as to determine whether to pass the filtered signals to a set of stable-state modules or to pass the filtered signals to a set of state-transition modules. After the state has been pre-classified, if the pre-classification indicates that the device is likely in a stable-state, Stable-State Feature Generator 406 generates a stable-state feature vector from the filtered signals and passes the stable-state feature vector to one or more Stable-State Classifiers 408 (described in greater detail below with reference to FIG. 4C) which provide estimations of a probability that the device is associated with different states in Markov Model 410 (described in greater detail below with reference to FIG. 4B).

Markov Model 410 combines the estimations from Stable-State Classifiers 408 with historical probabilities based on prior state estimates and probabilities of transitions between the states of Markov Model 410. Markov Model 410 is subsequently used to produce state probabilities corresponding to a probability for a state associated with the device (e.g., whether the device is in a user's pocket or on a table).

After the state has been pre-classified, if the pre-classification indicates that the device is likely in a state-transition, State-Transition Feature Generator 412 generates a state-transition feature vector from the filtered signals and passes the state-transition feature vector to one or more State-Transition Classifiers 414 (described in greater detail below with reference to FIG. 4D) which provide estimations of a probability of transitions between various states in Markov Model 410 (described in greater detail below with reference to FIG. 4B). Markov Model 410 uses the estimations from State-Transition Classifiers 414 to determine/adjust model transition probabilities for Markov Model 410. Markov Model 410 is subsequently used to produce state probabilities corresponding to a probability for a state associated with the device (e.g., assigning a probability that the device is in a user's pocket and a probability that the device is on a table).

In some embodiments, only one feature vector (e.g., stable-state feature vector or state-transition feature vector) is generated. In some embodiments, multiple feature vectors (e.g., multiple sets of stable-state features or multiple sets of state-transition features) are generated. For example, if there is some uncertainty as to a current condition under which the device is operating (e.g., the filtered signals indicated that the device is operating under either "Walking," or "Stationary" conditions), Pre-Classifier 404 selects multiple different stable-state feature vectors to be generated by Stable-State Classifiers 408 (e.g., Pre-Classifier 404 selects generation of a first set of stable state features to produce a first stable-state feature vector for use in identifying stable states of the respective device under "Walking" conditions and a second set of stable state features to produce a second stable-state feature vector for use in identifying stable states of the respective device under "Stationary" conditions). In some situations, there is some overlap between the multiple feature vectors, and a feature is generated once and used in two or more of the feature vectors. When there are multiple feature vectors, the feature vectors are used by corresponding classifiers (e.g., stable-state classifiers or state-transition classifiers) to generate stable-state measurements or state-transition measurements that are provided to Markov Model 410, which is used to produce state probabilities corresponding to a probability for a state associated with the device (e.g., whether the device is in a user's pocket, in the user's hand or on a table).

In some embodiments, there is resource utilization feedback from Markov Model 410 to Pre-Classifier 404 and information from Markov Model 410 is used to control Pre-Classifier 404. For example, if there is a high degree of certainty that the device is associated with a particular state and has been associated with that state for a long time (e.g., a device has been sitting on a table for the last 15 minutes), then Markov Model 410 optionally provides this information to Pre-Classifier 404 and Pre Classifier 404 uses this information to reduce the frequency with which measurement epochs (e.g., cycles of Pre-Classification, Feature Extraction and Classification) are performed.

Information about a device coupling state can be used for a variety of purposes at the device. For example, an estimate of a device coupling state can improve power management (e.g., by enabling the device to enter a lower-power state when the user is not interacting with the device). As another example, an estimate of a device coupling state can enable the device to turn on/off other algorithms (if the device is off Body, and thus is not physically associated with the user it would be a waste of energy for the device to perform step counting for the user). In some embodiments, the classification of device coupling includes whether the device is on Body or off Body, as well as the specific location of the device in the case that it is physically associated with the user (e.g., in a pocket, bag, the user's hand). Determinations about device coupling can be made by the device based on signatures present in small amplitude body motion as well as complex muscle tremor features that are distributed across X, Y and Z acceleration signals measured by the device. In some implementations, these signals are acquired at sampling rates of 40 Hz or greater.

In some embodiments, Sensor Data Filters 402 take in three axes of raw acceleration data and generate filtered versions of the acceleration data to be used in both Pre-Classifier 404 and either Stable-State Feature Generator 406 or State-Transition Feature Generator 412. One example of filtered signals used for user-device coupling are described in Table 1 below.

TABLE 1

Filtered Signals

| Filter Type | Filter Specifics |
| --- | --- |
| Low Pass | 0-2.5 Hz band. Uses 51 tap FIR (finite impulse response) filter. |
| High Pass | 1.5-20 Hz band. Uses 51 tap FIR filter. |
| Derivative Low Pass | Central difference derivative of low pass signal. |
| Envelope Derivative Low Pass | Uses a 31 tap Hilbert transform. The Hilbert transform produces complex analytic signal, and taking the magnitude of the analytic signal produces the envelope. |
| Envelope High Pass | Low pass filter the high pass using an 11 tap tent FIR filter. |

Pre-Classifier 404 is responsible for determining which types of features to generate (e.g., stable-state features or state-transition features), and passing an appropriate segment of sensor data (e.g., at least a subset of the filtered signals) to these feature generators (e.g., Stable-State Feature Generator 406 or State-Transition Feature Generator 412). In some embodiments, the determination of segment type is performed based on a combination of device motion context as well as based on features of the filtered signals generated by Sensor Data Filters 402.

In some embodiments, Pre-Classifier 404 serves as a resource allocation manager. For example, Pre-Classifier 404 allocates resources by specifying that one type of feature set is produced at a time (e.g., either producing stable-state features or state-transition features but not both). Additionally, in a situation where Pre-Classifier 404 determines that the device is in a stable-state (e.g., based on information from Markov Model 410), Pre-Classifier 404 manages the rate at which the device iterates through measurement epochs (e.g., a rate at which sets of filtered signals are sent to Stable-State Feature Generator 406). For example, if the model state has remained constant with high confidence for a predetermined amount of time (e.g., 1, 5, 10, 15 minutes, or a reasonable amount of time), the rate of the measurement epochs is decreased. Conversely, if a transition just occurred or if the model state is uncertain (e.g., the most likely model state has less than a predefined amount of certainty or the difference between the probability of the two most likely model states is below a predefined threshold), the rate of the measurement epochs is increased. In some embodiments, the provision of filtered signals to one of the feature generators (e.g., Stable-State Feature Generator 406 or State-Transition Feature Generator 412) determines whether or not the device is working to generate features from the filtered signals. As such, reducing or increasing the measurement epoch rate will have a corresponding effect on the overall processor utilization of the device, reducing the processor utilization when the device has been in the same state for a long time and increasing the processor utilization when the device has recently transitioned between states, which increases the overall energy efficiency of the device.

As one example (e.g., when a coupling state of the device is being determined), Pre-Classifier 404 determines whether to provide the filtered signals to Stable-State Feature Generator 406 or State-Transition Feature Generator 412 based on finding corresponding peaks in the low and high pass envelope signals indicative of sudden and/or sustained changes in motion of the device. The classifiers (e.g., Stable-State Classifiers 408 and/or State-Transition Classifiers 414) receive signal features. These features are extracted from either a state-transition or stable-state segment of low and high pass filtered signals (e.g., the filtered signals generated by Sensor Data Filters 402) provided by the Pre-Classifier 404. In some embodiments, the features used by Stable-State Classifiers 408 for stable-state classification differ from the features used by State-Transition Classifiers for state-transition classification, however both use the same underlying filtered signals produced by Sensor Data Filter(s) 402. For example, Stable-State Classifiers 408 use one or more of the Stable-State Features described in Tables 2a-2c, below, while State-Transition Classifiers 414 use one or more of the State-Transition Features described in Table 3, below. It should be understood that the features described in Tables 2a-2c and 3 are not an exhaustive list but are merely examples of features that are used in some embodiments.

TABLE 2a

Stable-State Features (Walking or Standing)

| Feature | Signal Processing to Derive Feature |
| --- | --- |
| Coordinated Movement (low pass) | Correlation of the XY, XZ and YZ zero-mean low pass filtered signals |
| Spectral Energy | Normalized power of the spectrum of the high pass signal and normalized spectral bins, 4 Hz in width, between 0 and 20 Hz. Normalization of the power is based on training subject distribution and bin normalization is based on the power of the subjects given time segment |

TABLE 2b

Stable-State Features (Standing)

| Feature | Signal Processing to Derive Feature |
| --- | --- |
| Tilt Variation and High Frequency Variation | Variance of the low and high pass signals |
| Coordinated Movement (high pass) | Correlation of the XY, XZ and YZ envelope of the high pass filtered signals |
| Variability in Signal Bandwidth | Hjorth mobility for X, Y and Z where Hjorth mobility is calculated from the power of the first derivative of the high pass signal scaled by the variance of the high pass signal. |
| Signal Bandwidth | Hjorth purity for X, Y and Z where Hjorth purity is calculated from the square of the power of the first derivative of the high pass signal scaled by the product of the variance of the high pass signal and the power of the second derivative of the high pass signal |
| Spectral Energy (high pass) | Normalized power of the spectrum of the high pass signal and normalized spectral bins, 4 Hz in width, between 0 and 20 Hz. Normalization of the power is based on training subject distribution and bin normalization is based on the power of the subjects given time segment |

TABLE 2c

Stable-State Features (Walking)

| Feature | Signal Processing to Derive Feature |
|---|---|
| Tilt Angle at the start of a step | Median + low-pass filtered accelerometer signals |
| Tilt Variation over a stride (two steps) and a single step | Difference in tilt angle between start and end of a stride as well as between start and end of individual steps |
| Step Symmetry | Ratio of the difference in inertial Z peaks at start and end of a step for two successive steps (a single stride) |
| Relative power and range of signals in the User's Vertical vs Horizontal directions. | Signals are transformed to a pseudo-user frame using the median + low-pass based tilt angle estimates Ratio of the range in the horizontal versus vertical low-pass filtered signals over a stride Ratio of the signal energy in the horizontal versus vertical low-pass filtered signal |
| Amplitude and Phase of Step Impact Response | Peak of the high-pass filtered signal in the pseudo-user frame vertical direction, as well as phase of the peak relative to the start of a step |
| Spectral power of walk and stride signals | Normalized power of the spectrum of the zero-mean signal in pseudo-user frame in spectral bins, 0.5 Hz in width, at the estimated walk(step) and stride frequencies. Walk and stride frequencies are estimated by finding two harmonic peaks in the spectrum of the vertical signal within a predefined frequency range (below 2.25 Hz) |
| Range and variance of signals in the User's Vertical and Horizontal directions. | Range and variance of signals transformed into a pseudo-user frame over a single stride |
| Spectral power of signals in the User's Vertical and Horizontal directions. | Normalized and unnormalized power of the spectrum of the signal in pseudo-user frame in spectral bins, 2.5 Hz and 6 Hz in width, between 0 and 17.5 Hz |

In some embodiments, the term "Hjorth mobility" used in Table 2b corresponds to the square root of a comparison between (1) the variance of the rate of change of movement in a respective direction (e.g., the y direction) and (2) the variance of the amount of movement in the respective direction (e.g., using Equation 1, below)

$$\text{Hjorth Mobility} = \sqrt{\frac{\text{Var}\left(\frac{dy}{dt}\right)}{\text{Var}(y)}} \quad (1)$$

In some embodiments, the term "Hjorth purity" used in Table 2 corresponds to the square root of a comparison between (1) the square of the variance of the rate of change of movement in a respective direction (e.g., the y direction) and (2) the product of the variance of the amount of movement in the respective direction and the variance of the acceleration in the respective direction (e.g., as shown in Equation 2, below)

$$\text{Hjorth Purity} = \sqrt{\frac{\left(\text{Var}\left(\frac{dy}{dt}\right)\right)^2}{\text{Var}(y)\text{Var}\left(\frac{d^2y}{dt^2}\right)}} \quad (2)$$

TABLE 3

State-Transition Features

| Feature | Signal Processing to Derive Feature |
|---|---|
| Tilt Angle and Tilt Variation | Mean and variance of the low pass filtered signals. |
| Coordinated motion (low pass, mutual information) | Mutual information between XY, XZ and YZ pairs of low pass filtered signals. |
| Coordinated motion (high pass, mutual information) | Mutual information between XY, XZ and YZ pairs of envelope of high pass filtered signals. |
| Coordinated motion (low pass, correlation) | Correlation of the XY, XZ and YZ zero-mean low pass filtered signals. |
| Coordinated motion (high pass, correlation) | Correlation of the XY, XZ and YZ envelope of the high pass filtered signals. |
| Max Energy and Time of Max Energy | Peak amplitude and normalized time to peak of the envelope of the high pass signal. |
| Spectral Energy | Dominant modes of the spectrum of the high pass signal. |
| Tilt Variation Extrema and Associated Time | Signed peak amplitude and normalized time to peak of the derivative of the low pass signal. |

Figure 4B:
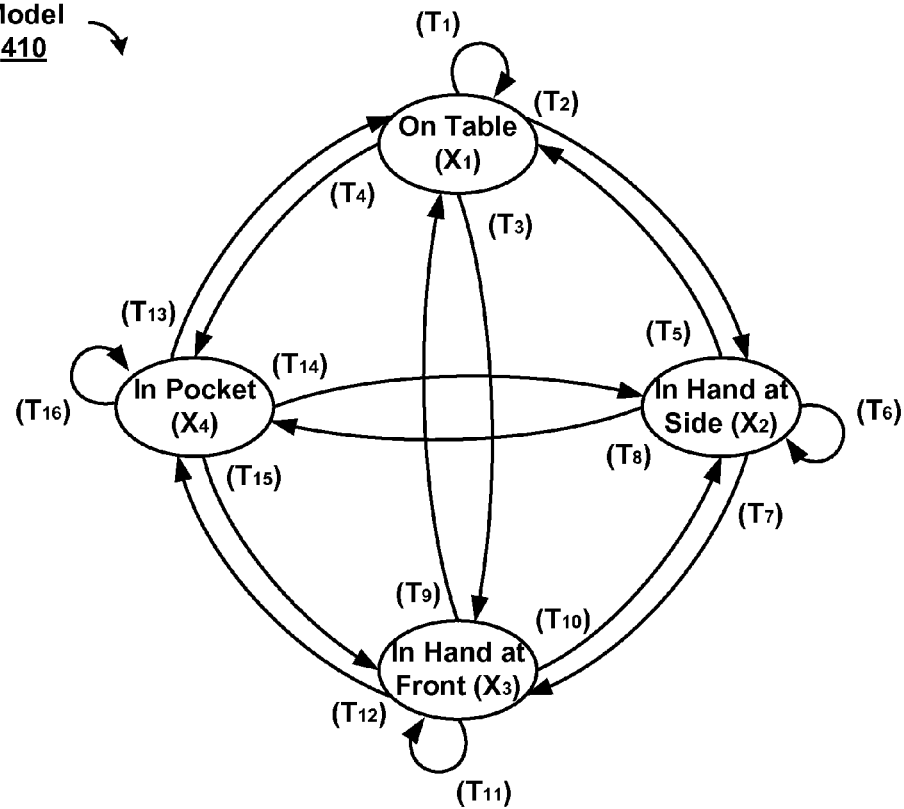

FIG. 4B illustrates an example of a probabilistic model which defines the specific set of states associated with the device. In FIG. 4B, the probabilistic model is Markov Model 410. While four states (e.g., "On Table," "In Hand at Side," "In Hand at Front," and "In Pocket") are shown in FIG. 4B, it should be understood that, in principle Markov Model 410 could have any number of states. In some embodiments, the probabilistic model imposes logical constraints on the transition between the states, preventing infeasible events such as going from "On Table" to "In Pocket" without first going through "In Hand at Side" (e.g., the transition probability $P(T_4)$ from $X_1$ to $X_4$ is set to zero). The same set of states and transitions are used when the device is in a stable state and when the device is in a state transition. When the device is in a stable state, output from Stable-State Classifiers 408 is used to update the state probabilities of Markov Model 410, optionally, without updating the model transition probabilities (e.g., as described in greater detail below with reference to FIG. 4C). In contrast, when the device is in a state transition, output from the State-Transition Classifiers 414 is used to update the model transition probabilities are changed from P to P' (e.g., as described in greater detail below with reference to FIG. 4D).

The use of a probabilistic model for determining device state increases the robustness of the overall classification and allows for improved management of resource utilization. In terms of robustness, the probabilistic model (e.g., Markov Model 410) incorporates the idea that the past provides information about the future. For example, the longer the device goes without observing a transition between states, the more confident the device is that a current state associated with the device is constant (unchanging with time). In addition, if recent observations have all indicated the same respective state associated with the device, the probabilistic model (e.g., Markov Model 410) will have a high probability of the respective state being the current state and thus will assign a lower probability on other states. This assignment of probabilities effectively places a lower weight on new measurements that indicate a different state from the respective state, which reduces the likelihood that outlier sensor measurements will result in state misclassifications. In terms of resource utilization, the probabilistic model is, optionally, used to adapt the update rate of the underlying classifiers based on the current confidence level (probability) of one or more of the states (e.g., each state). In particular, as a confidence level in a current state increases, the update rate of the stable state measurements (e.g., the frequency of measurement epochs) is, optionally, decreased until a transition measurement occurs, at which point the update rate increases again.

Markov Model 410 has two different modes of operation, a stable-state update mode of operation for use when Pre-Classifier 404 does not detect a transition between states and a state-transition update mode of operation for use when Pre-Classifier 404 detects a transition between states. In the stable-state updated mode, a Stable-State Markov Model Transition Matrix 420 is used. In the state-transition updated mode, a State-Transition Markov Model Transition Matrix 422 is used.

A stable-state update of Markov Model 410 is invoked by an updated Stable-State Classifier 408 output. The update consists of two parts, a motion update (e.g., equation 3, below) and a measurement update (e.g., equation 4, below):

$$\tilde{P}(X_{i,t}) = \sum_{j=1}^{n} P(X_{i,t} \mid X_{j,t-1}) P(X_{j,t-1}) \quad (3)$$

Equation 3 updates the model states, where $\tilde{P}(X_{i,t})$ is the model-predicted probability of state $X_i$ at time t, which is calculated by adding up the probabilities that the state transitioned from other states $X_j$ to state $X_i$. In equation 3, the probability that state $X_j$ transitioned to state $X_i$ is based on a state-transition matrix $P(X_{i,t}|X_{j,t-1})$ (e.g., Stable-State Markov Model Transition Matrix 420 in FIG. 4B) that specifies a probability of transition between state $X_j$ and state $X_i$ and a probability $P(X_{j,t-1})$ of state $X_j$ being a current state associated with the device at a prior time step.

After determining the model-predicted probability, a combined probability is determined based on the model-predicted probability and a measurement probability based on the Stable-State Classifier 408 outputs (e.g., using equation 4).

$$P(X_{i,t}) = \alpha P(X_{i,t}|y_t) \tilde{P}(X_{i,t}) \quad (4)$$

Equation 4 computes a combined probability of model states, where $P(X_{i,t})$ is the combined probability of state $X_i$ at time t, which is calculated by combining the model-predicted probability of state $X_i$ at time t, $\tilde{P}(X_{i,t})$, with a measurement probability, $P(X_{i,t}|y_t)$, that is computed directly by Stable-State Classifiers 408, as described in greater detail below with reference to FIG. 4C. In Equation 4, above, $\alpha$ is a scaling parameter. The elements in the state transition matrix, $P(X_{i,t}|X_{j,t-1})$, are deterministic and defined based on a given model. When the elements of the state transition matrix are other than 1's and 0's, this component of the model allows for diffusion of the probabilities over time (e.g., over sequential measurement epochs). In other words, in some situations, without any observations (e.g., contributions from measurement probability $P(X_{i,t}|y_t)$), this component will eventually lead to lower certainty in Markov Model 410 states over time.

In contrast, the state-transition update of Markov Model 410 is invoked by an updated State-Transition Classifier 414 output. The update involves first computing transition probabilities for P' based on State-Transition Classifier 414 outputs and prior model state probabilities (e.g., as shown in equation 5, below), and then updating the model state probability accordingly (e.g., as shown in equation 6, below). It is effectively a motion update with a modified state transition matrix built from the outputs of the transition classifiers.

$$P'(X_{i,t} \mid X_{j,t-1}) = \sum_{k=1}^{m} P(X_{i,t} \mid T_{k,t}) P(T_{k,t} \mid X_{j,t-1}) \quad (5)$$

Figure 4C:
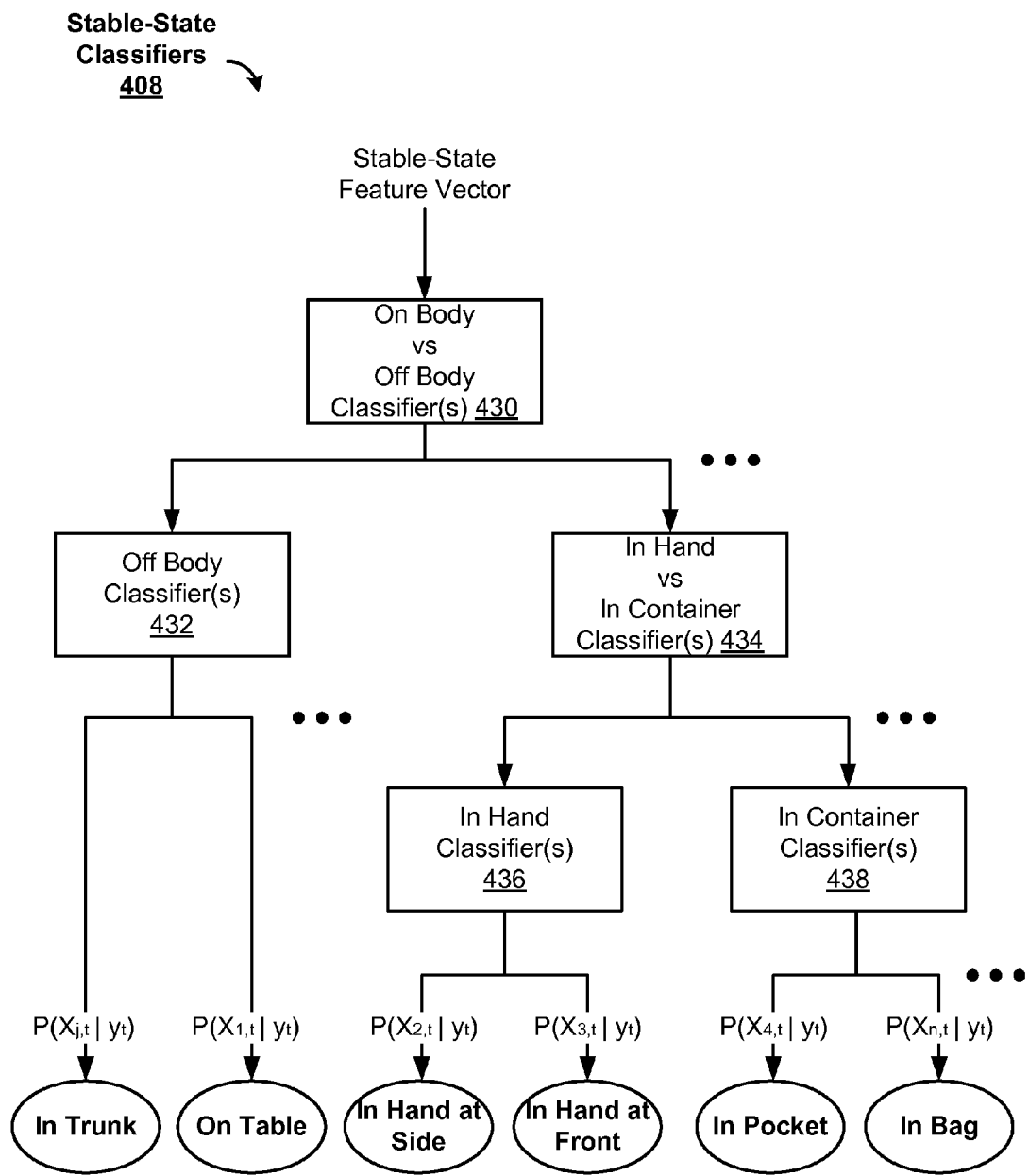
Figure 4D:
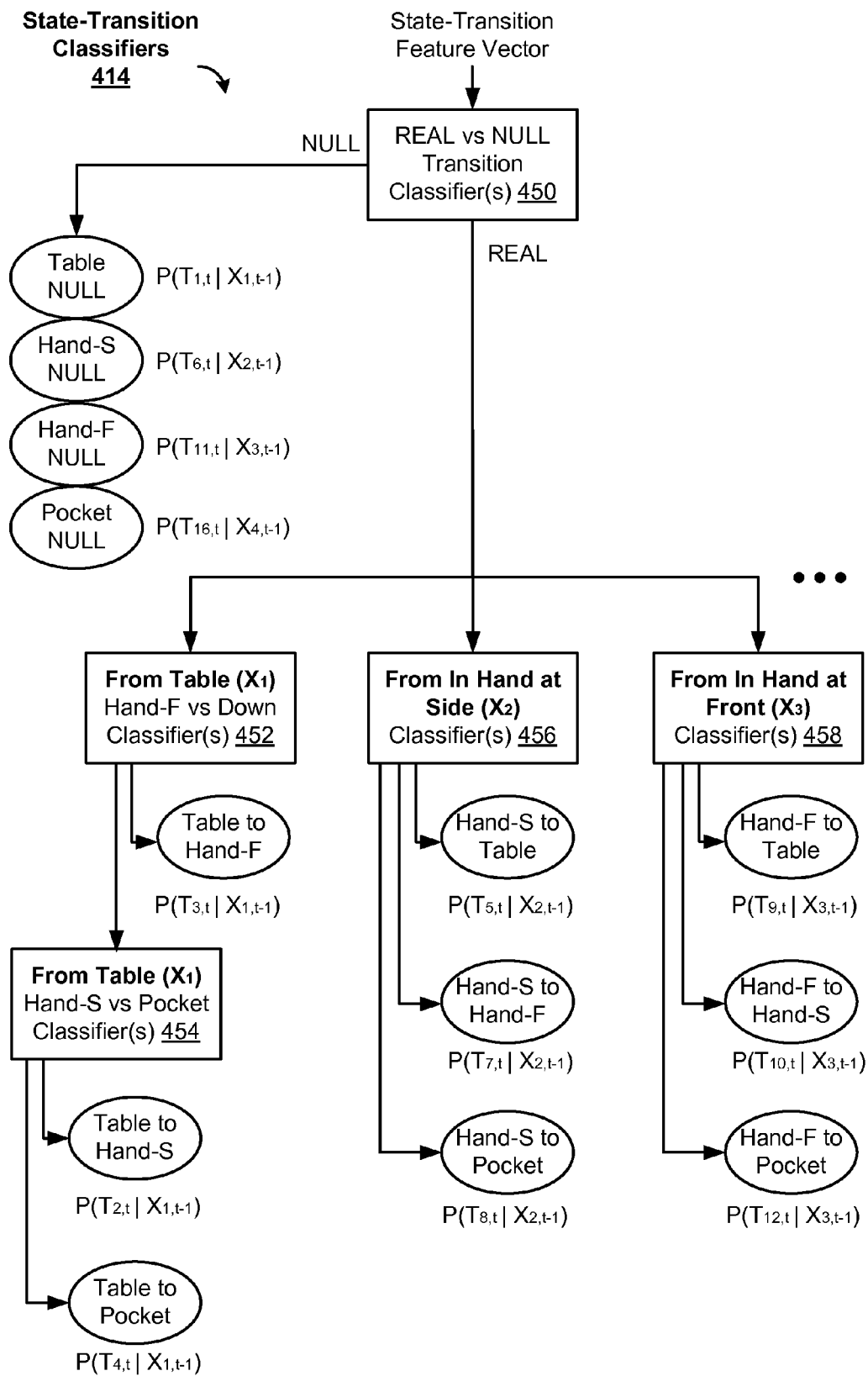
Figure 5A:
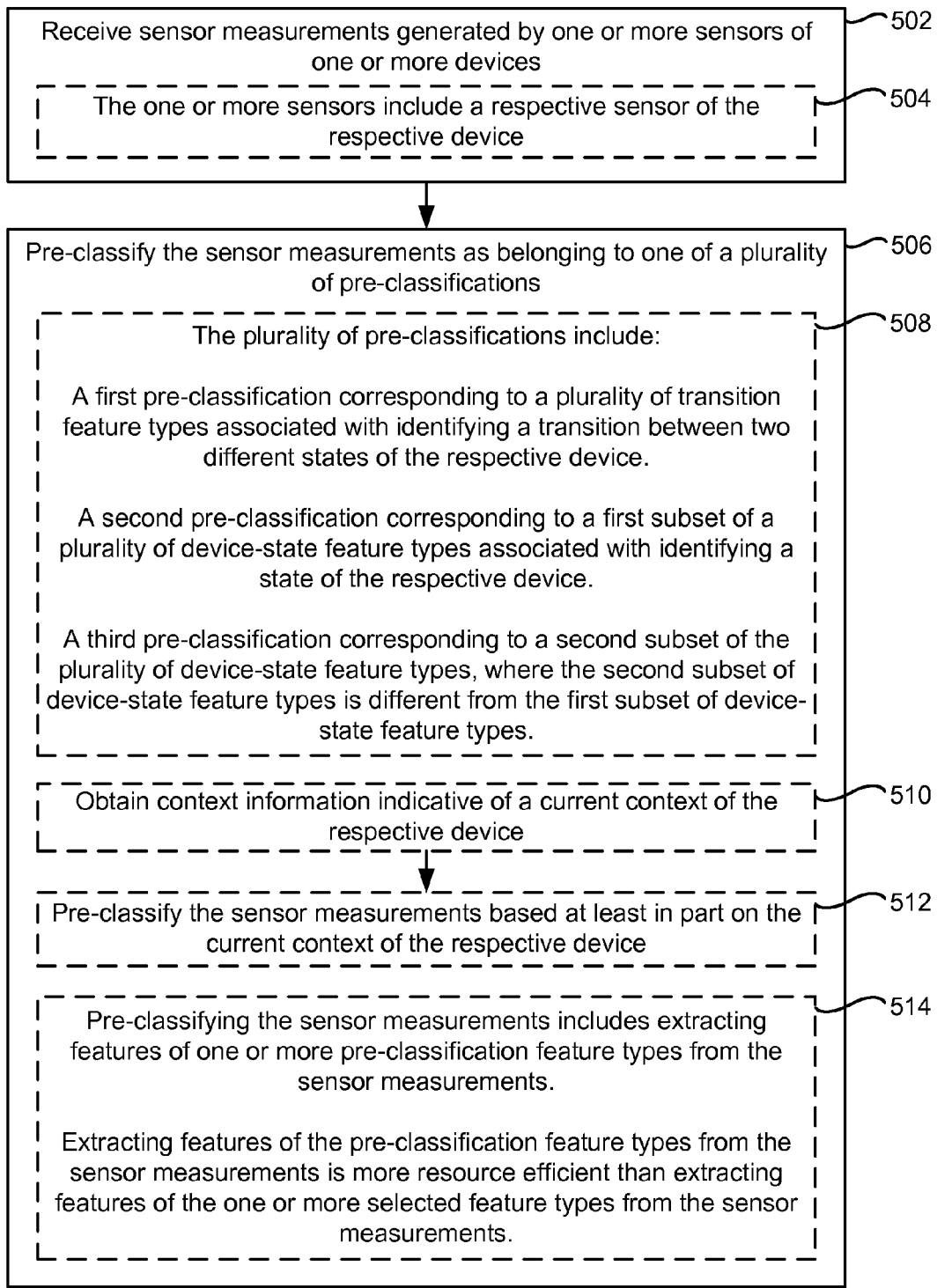
FIGS. 5A-5I are flow diagrams of a method for determining a state of a device, according to some embodiments.
Figure 5B:
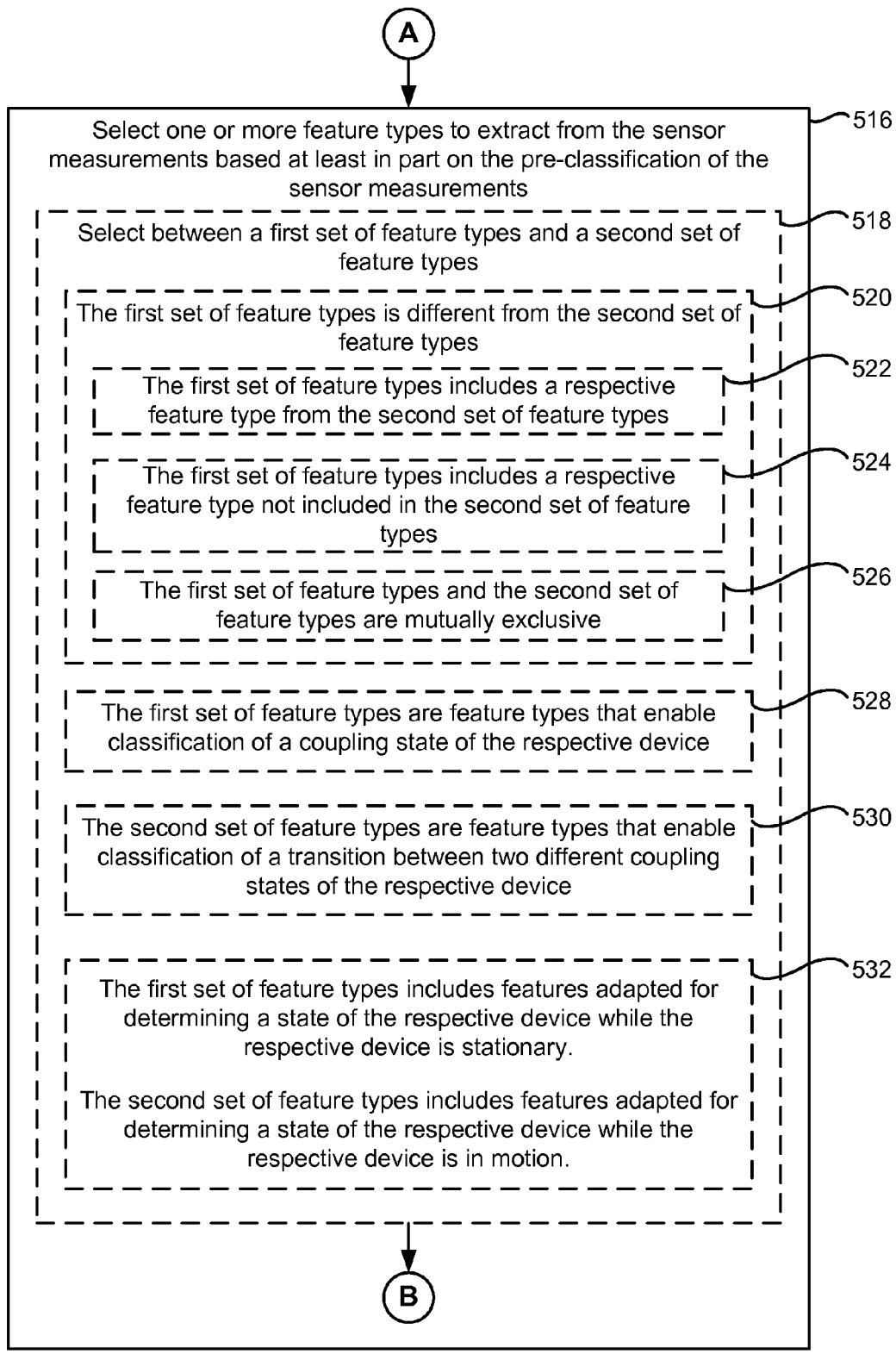
Figure 5C:
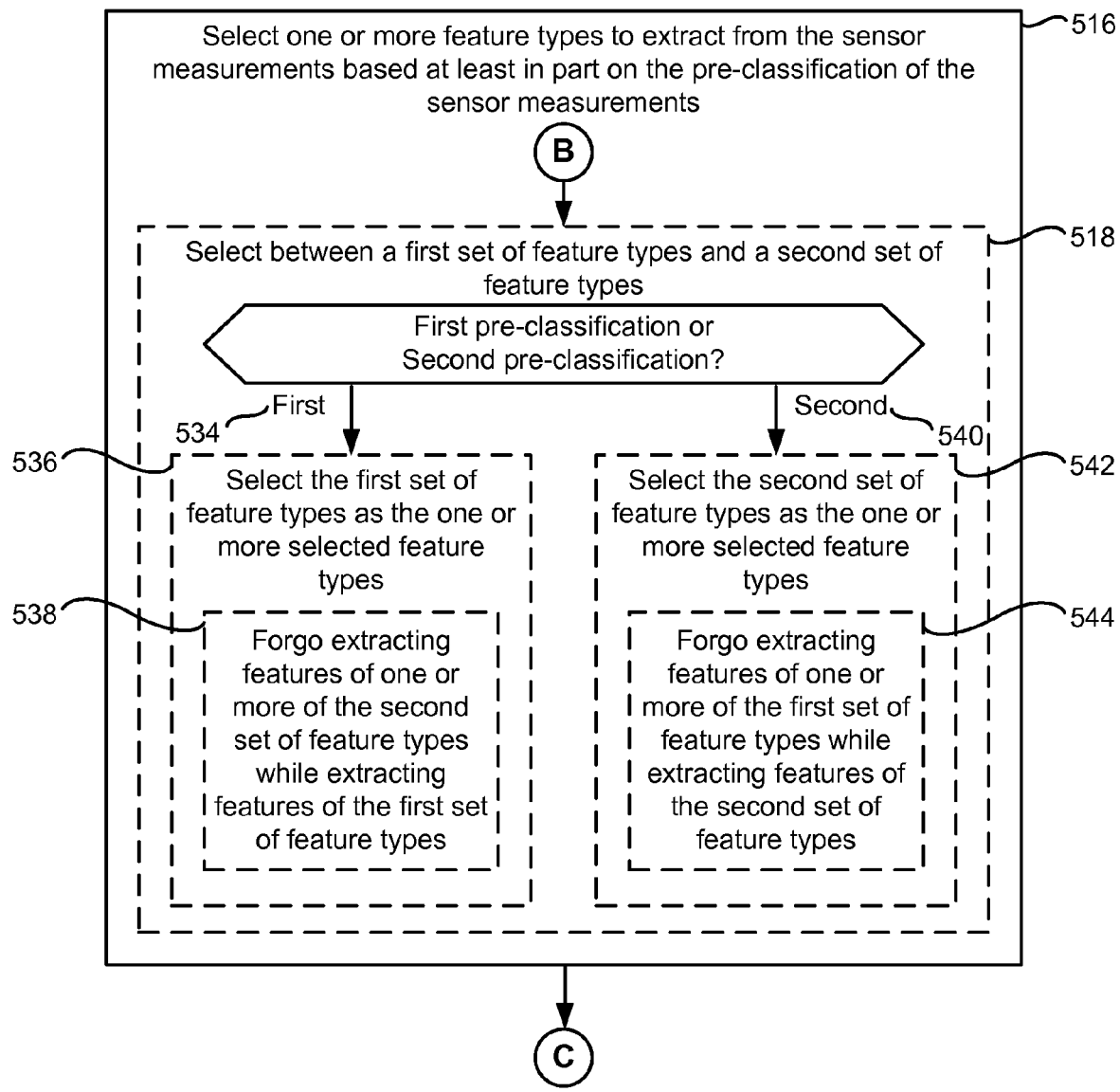
Figure 5D:
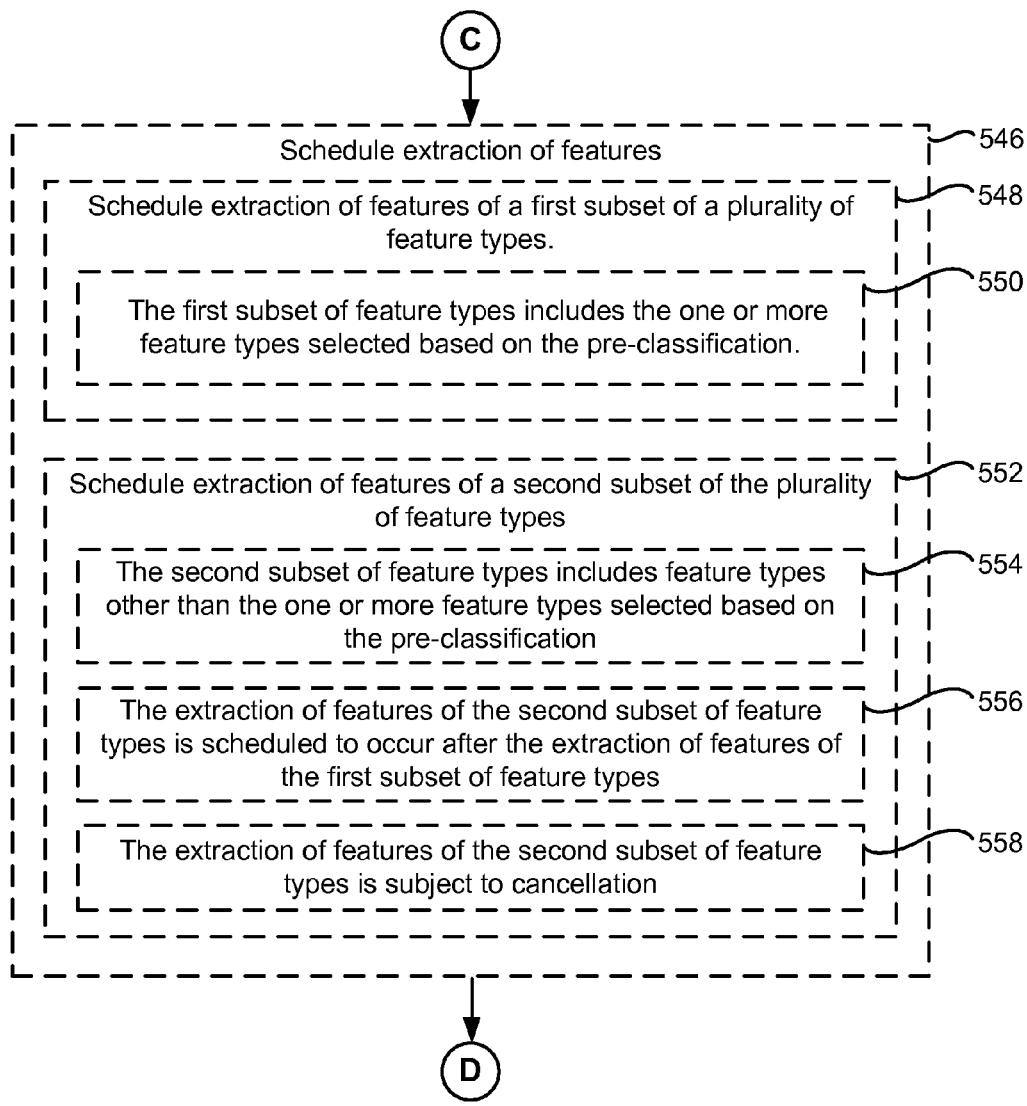
Figure 5E:
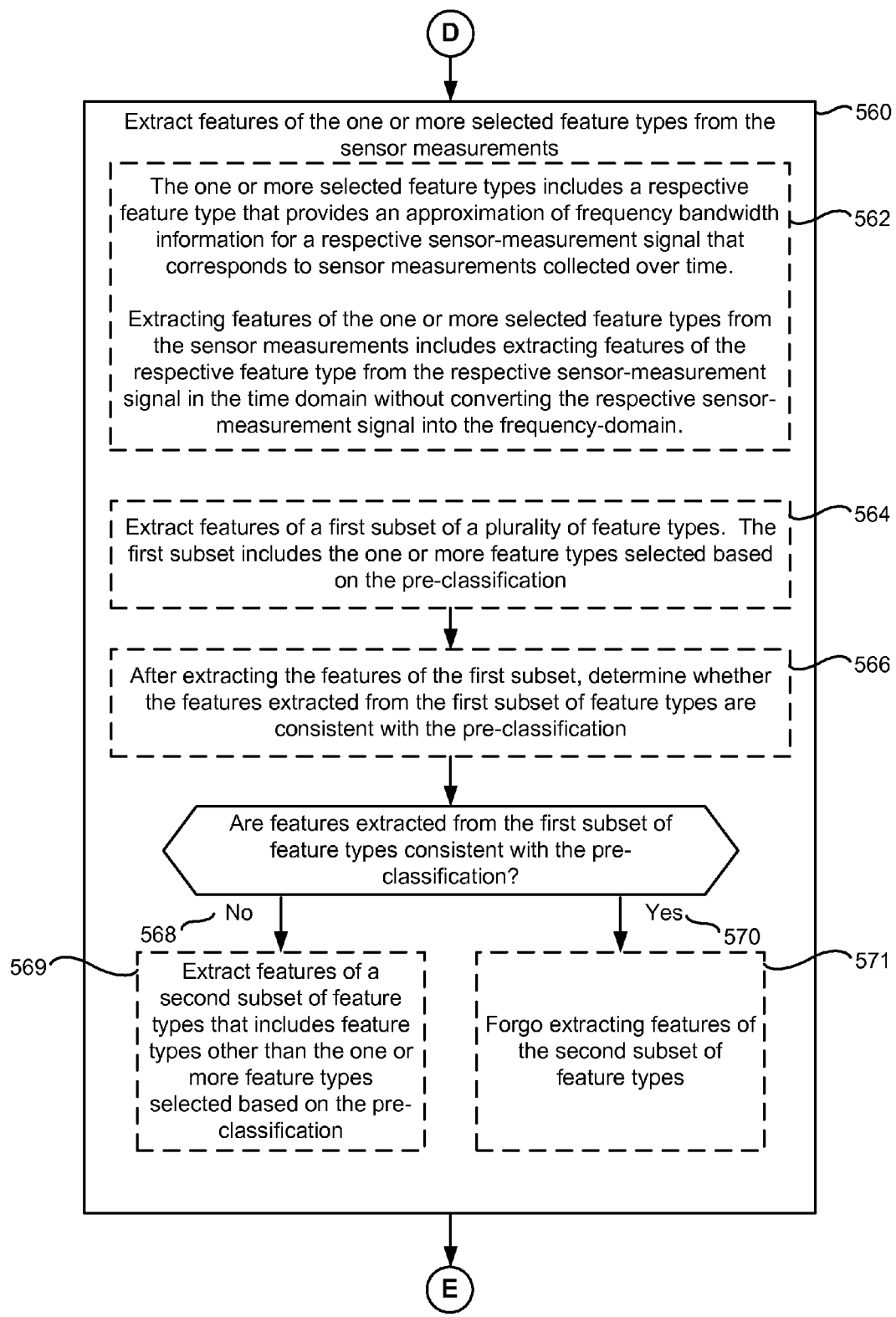
Figure 5F:
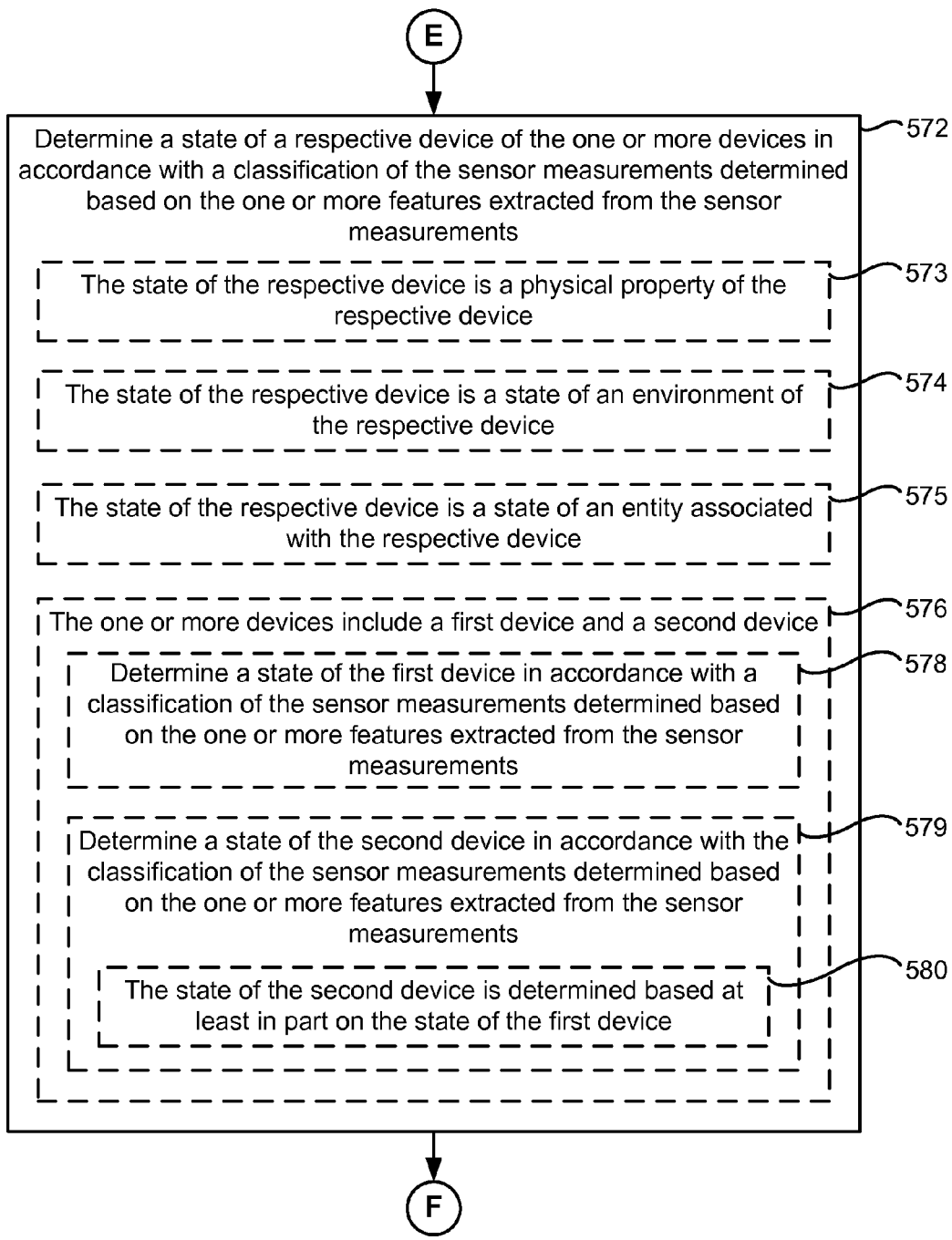
Figure 5G:
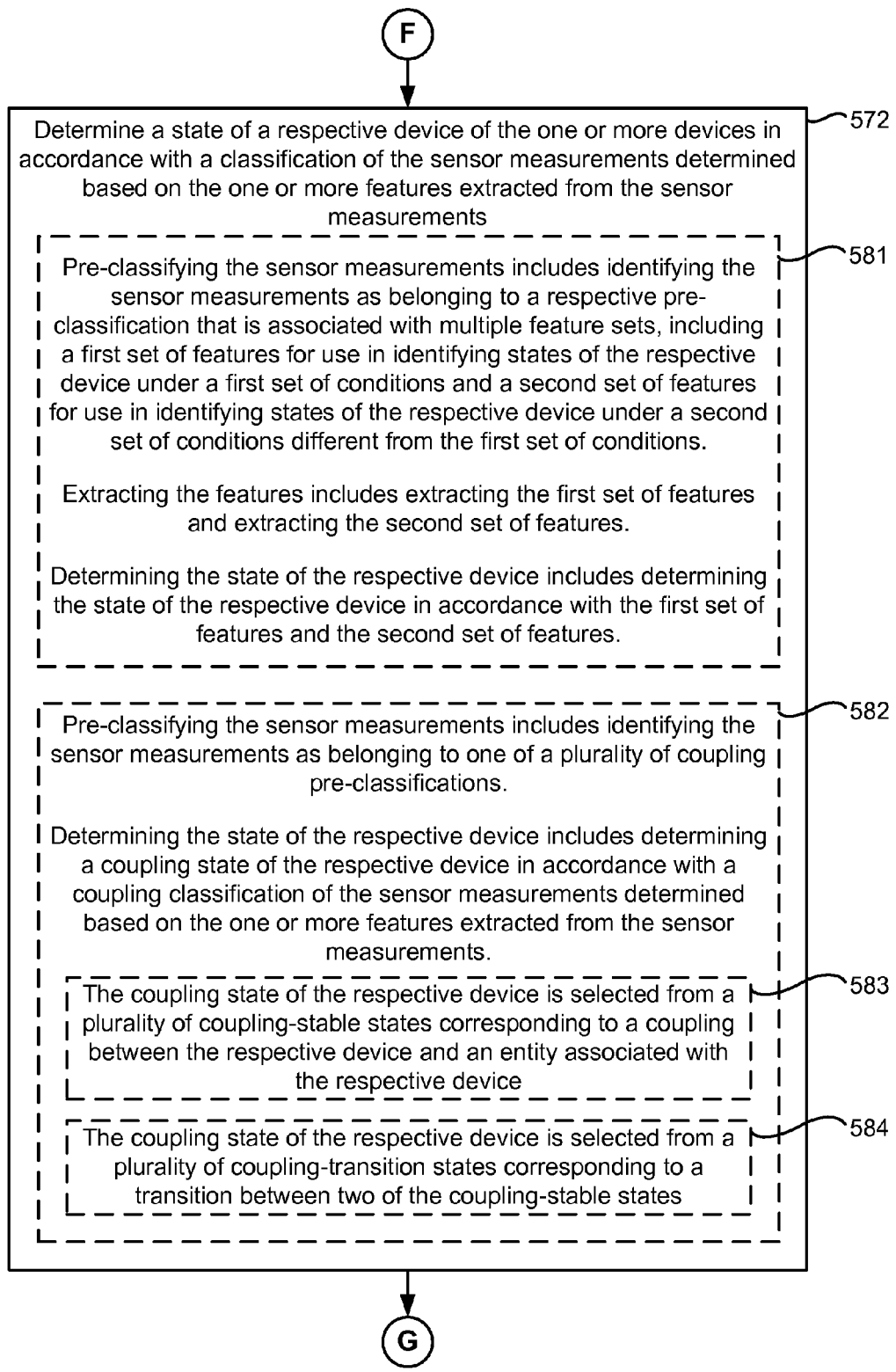
Figure 5H:
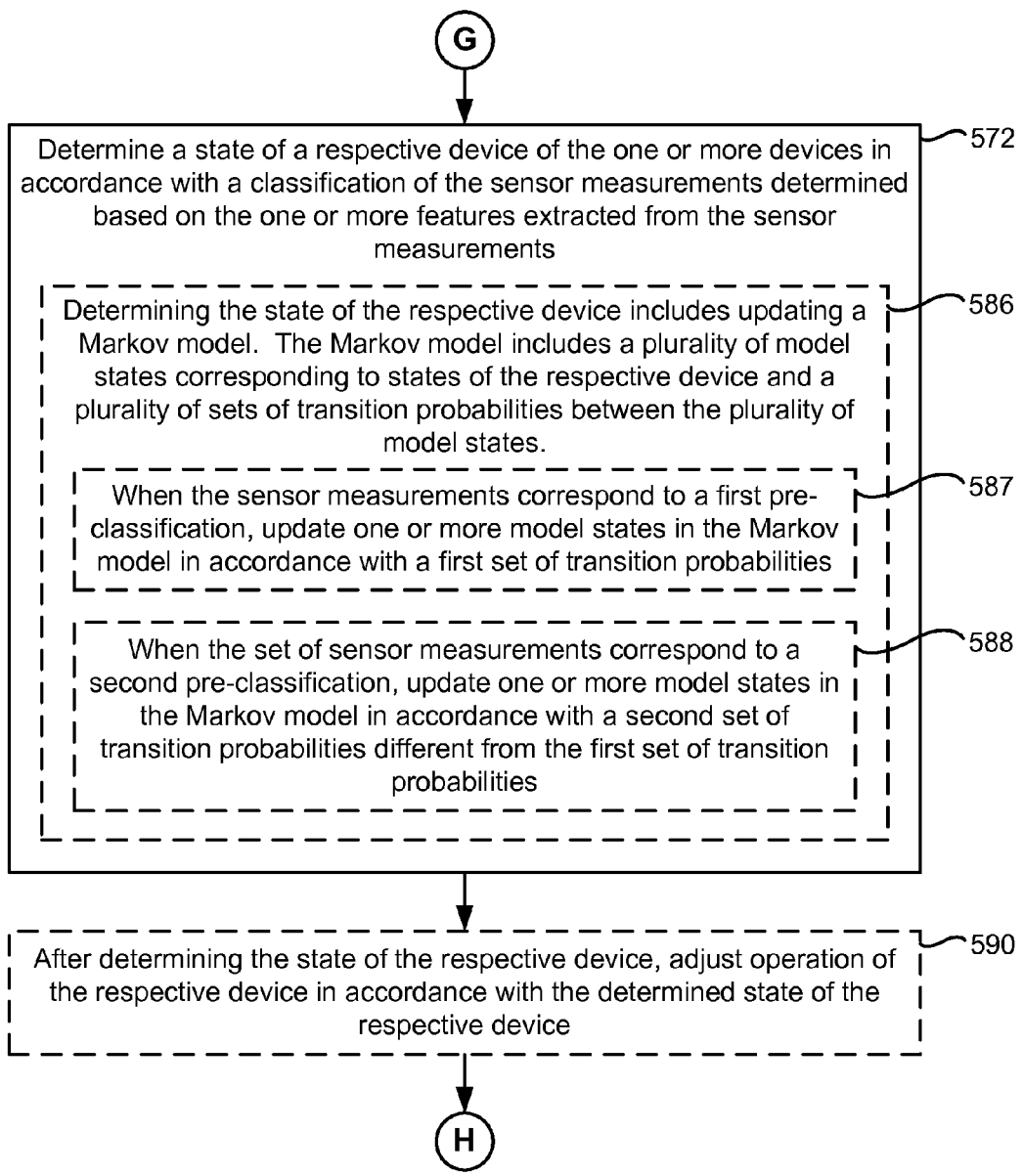
Figure 5I:
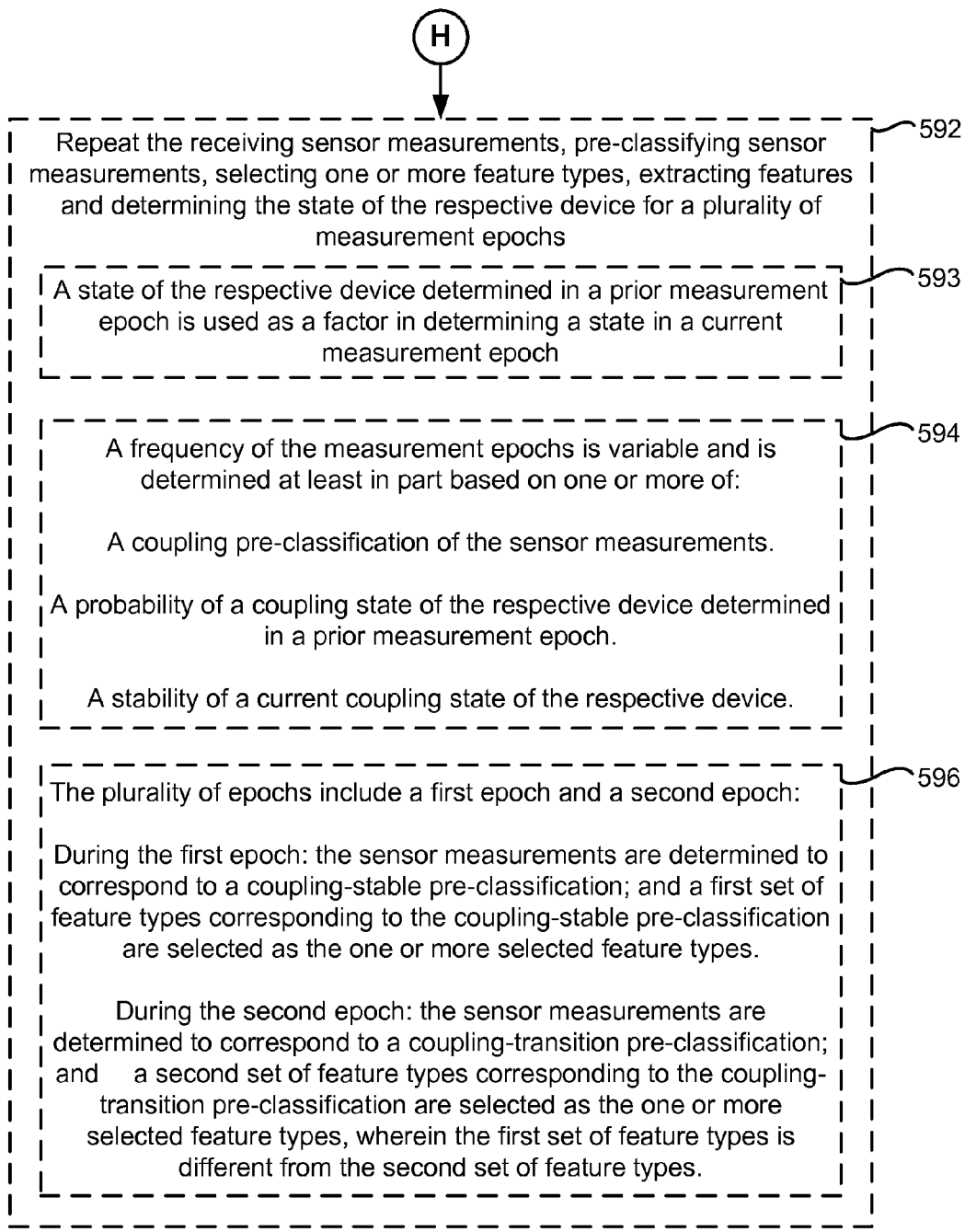

Equation 5 computes a modified transition matrix, where $P'(X_{i,t}|X_{j,t-1})$ (e.g., State-Transition Markov Model Transition Matrix 422 in FIG. 4B) is the measurement-based state transition matrix which includes elements corresponding to updated transition probability for a transition from state $X_j$ to state $X_i$, which is calculated based on a measurement transition probability $P(T_{k,t}|X_{j,t-1})$, that is computed directly by State-Transition Classifiers 414, as described in greater detail below with reference to FIG. 4D. In some embodiments, the updated transition probability is the same as the measurement transition probabilities computed by State-Transition Classifiers 414. In some embodiments, the measurement transition probabilities are modified by a transition definition matrix P $(X_{i,t}|T_{k,t})$ that defines how transitions relate to each other and the model states. In a simple model, the elements of the transition definition matrix are 1's and 0's, which encode the arrows shown in Markov Model 410 in FIG. 4B. For example, P(Table|OnTableFromPocket)=1, while P(Pocket|OnTableFromPocket)=0 (for a ToTable transition, the probability that the next state is table is 100%, whereas the probability that the next state is anything else is 0%). In still more complex models (e.g., where there are dependencies between the probabilities of transitioning between different states of the probabilistic model, the transition definition matrix can have elements with values between 1 and 0 that encode these more complex dependencies).

After determining the modified state transition matrix, probabilities of the states of Markov Model 410 are updated using the modified state transition matrix (e.g., using equation 6) to determine updated probabilities for the model states of Markov Model 410.

$$P(X_{i,t}) = \sum_{j=1}^{n} P'(X_{i,t} \mid X_{j,t-1}) P(X_{j,t-1}) \quad (6)$$

Equation 6 updates the model states, where $P(X_{i,t})$ is the model-predicted probability of state $X_i$ at time t, which is calculated by adding up the probabilities that the state transitioned from other states $X_j$ to state $X_i$. In contrast to equation 3, in equation 6, the probability that state $X_j$ transitioned to state $X_i$ is based on a measurement-based state transition matrix $P'(X_{i,t}|X_{j,t-1})$ that specifies a probability of transitioning between state $X_j$ and state $X_i$ in accordance with the output of State-Transition Classifiers 414. The measurement-based state transition matrix is combined with the probabilities $P(X_{j,t-1})$ of states $X_j$ being a current state associated with the device to generate updated model-predicted probabilities for the various model states.

For example, if State-Transition Classifiers 414 indicate that it was almost certain that the device transitioned from On Table to In Hand at Front, then $P'(T_3)$ (also referred to as $P'(X_{3,t}|X_{1,t-1})$) will be increased to approximately 1 and any probability that the device was in the On Table state at the prior time step will flow to a probability the device is In Hand at Front at the next time step. Thus, if in the prior time step there was a high probability (e.g., approximately 1) that the device was On Table, then there will be a substantially increased probability that the device is in the In Hand at Front state at the next time step. In contrast, if there was a relatively low probability (e.g., approximately 0) that the device was in the On Table state at the prior time step, then there will be relatively little contribution to a change in the probability that the device is in the In Hand at Front state at the next time step due to a flow of probability from the On Table state. In this example, the error correction benefits of Markov Model 410 are illustrated, as a single erroneously identified transition (e.g., a transition that corresponds to a transition from a state that is not a current state of the device) will have very little impact on the overall model state probabilities, while a correctly identified transition (e.g., a transition that corresponds to a transition from a state that is a current state of the device) will enable the device to quickly switch from a prior state to a next state.

FIG. 4C illustrates a set of example Stable-State Classifiers 408 in accordance with some embodiments. In this example, Stable-State Classifiers 408 are implemented as a voting machine. As shown in FIG. 4C, an On Body vs Off Body Classifier 430 (or set of classifiers) receives a Stable-State Feature vector and determines a probability that the device is On Body or Off Body. Off Body Classifier(s) 432 determine a probability that, if the device is Off Body, the device is In Trunk or On Table. Similarly, In Hand vs. In Container Classifier(s) 434 determine a probability that, if the device is On Body, the device is In Hand or In a Container. Subsequently, corresponding classifiers (e.g., In Hand Classifier(s) 436 and In Container Classifier(s) 438) further divide probabilities so as to produce a set of measurement probabilities, $P(X_{i,t}|y_t)$ which are combined with model-predicted probabilities to ascertain a combined probability of the states associated with the device for the current measurement epoch, as described above with reference to equations 3-4.

For Example in FIG. 4C, the probability of a current state of device is divided between "In Trunk," "On Table," "In Hand at Side," "In Hand at Front," "In Pocket," and "In Bag." While the above six states are provided for ease of illustration, it should be understood that, in principle, Stable-State Classifiers 408 could determine measurement probabilities for any number of states of a probabilistic model. Additionally, while a specific voting machine is illustrated in FIG. 4C, any of a variety of different types of voting machines (e.g. support vector machine, neural network, decision tree) could be used depending on the situation and implementation. The resulting overall output of the classifier voting machines are interpreted as probabilities, indicating the likelihood of the given state. By using a group of underlying classification algorithms rather than any single one, in this embodiment, the output of the voting machine classifier is more robust and can more accurately reflect the confidence of the classification. In some embodiments, a feedback infinite impulse filter on the voting machine output is also employed to suppress spurious misclassifications.

FIG. 4D illustrates a set of example State-Transition Classifiers 414 in accordance with some embodiments. In this example, State-Transition Classifiers 414 are implemented in a hierarchy. As shown in FIG. 4D, a REAL vs NULL Classifier 450 (or set of classifiers) receives a State-Transition Feature vector and determines a probability that the device experienced a transition (e.g., determining whether Pre-Classifier 404 accidentally identified a transition or identified a transition that is not modeled in the probabilistic model). The probability that the transition was a null transition is assigned to all of the null transitions in the matrix. For example, if it is almost certain that there was no transition, null transitions for all of Markov Model 410 states are set to approximately 1 and the estimated state of the device will remain substantially constant for the current measurement epoch. In contrast, if the transition is determined to have some probability of being a real transition, a non-zero probability is assigned to the real (e.g., non-null transitions). In particular, State-Transition Classifiers 414 determine conditional probabilities using a plurality of conditional classifiers. From Table Hand-F vs Down Classifier 452 determines a probability, if the state is On Table, that the state transitioned to Hand-F (In Hand at Front) or some other state. The probability that the state transitioned from On Table to some other state is handled by From Table Hand-S vs Pocket Classifier 454, which determines a probability, if the state is On Table, that the state transitioned to Hand-S (In Hand at Side) or In Pocket. Similarly, From In Hand at Side Classifier 456 determines a probability, if the state is In Hand at Side, that the state transitioned to On Table, Hand-F (In Hand at Front) or In Pocket. Likewise, From In Hand at Front Classifier 458 determines a probability, if the state is In Hand at Front, that the state transitioned to On Table, Hand-S (In Hand at Side at Front) or In Pocket. State-Transition Classifiers 414 assign probabilities so as to produce a set of measurement transition probabilities, $P(T_{k,t}|X_{j,t-1})$, which are, optionally, combined with a transition definition matrix and are used to produce a modified state transition matrix for use in updating Markov Model 410 for the current measurement epoch, as described in greater detail above with reference to equations 5-6.

For Example in FIG. 4D, measurement transition probabilities are calculated for null transitions for "On Table," "In Hand at Side," "In Hand at Front," "In Pocket," and measurement transition probabilities are calculated for transitions away from "On Table," "In Hand at Side," "In Hand at Front," states. While examples of thirteen transitions states are provided above for ease of illustration, it should be understood that, in principle, State-Transition Classifiers 414 could determine measurement transition probabilities for any number of transitions between states of the probabilistic model. Additionally, while a specific voting machine is illustrated in FIG. 4D, any of a variety of different types of voting machines (e.g. support vector machine, neural network, decision tree) could be used depending on the situation. The resulting overall output of the classifier voting machines are interpreted as transition probabilities, indicating the likelihood of transition between states. Additionally, in some implementations, the results of the voting machine are normalized, weighted and/or combined to produce an overall transition probability result and confidence metric. By using a group of underlying classification algorithms rather than any single one, the output of the voting machine classifier is more robust and can more accurately reflect the confidence of the transition probability. In some embodiments, a feedback infinite impulse filter on the voting machine output is also employed to suppress spurious misclassification of transitions.

Posture States

While the examples of the system and method of determining a state associated with a device described above relate primarily to device coupling states, it should be understood that the state associated with the device could be virtually any state of a device, state of an environment of a device or state of an entity associated with a device. In other words, the framework described above is general enough to be applicable to a number of different types of state classification that include measurable stable-states and state-transitions between those stable-states.

For example, the framework above could also be used in a situation where the device is associated with an entity (e.g., user) and the states are body posture states of the user. For this user-posture implementation, the steady states include one or more of sitting, standing, walking, running and the transitions refer to changes between those (sitDown, standUp, start-Walking, stopWalking) While the overall framework is the same as that discussed above, at least some of the specific details would be slightly different, as described below.

In an example of a user-posture implementation, Pre-Classifier 404 would make determinations as to whether to operate in a stable-state mode or a state-transition mode based on filtered signals corresponding to YZ accelerations detected by sensors of the device. For example, the device low-pass filters the YZ norm of the raw accelerations, and median filters that norm. In some embodiments, the transient is obtained by subtracting the median filtered value from the low-pass filtered one.

In the user-posture implementation example, Pre-Classifier 404 seeks half a second of relative inactivity, followed by period of elevated transient accelerations, followed by another half second of "silence." In some embodiment, the length of the period of elevated activity is required to fall within reasonable bounds (e.g., from 1.75 to 3 seconds) for common activities such as sitting/standing transitions. The rationale for the upper bound on the period of elevated activity is that if the device is experiencing a relatively high level of continuous activity, either there is no transition and the device is simply being subjected to continuous transient accelerations or the device is being transitioned between a large number of states quickly (e.g., the user is repeatedly standing up and sitting down) and it would be futile and/or computationally or energy inefficient to attempt to keep track of all of the transitions. In some embodiments, inactivity or silence detection is determined by a threshold on the transient YZ acceleration norm. An example of a stillness threshold for filtered accelerations is approximately 0.5 m/s$^2$. Table 4 includes a list of example user-posture features for use as stable-state and/or state-transition features for the user-posture implementation.

TABLE 4

Posture Transition Features

| Feature | Signal Processing to Derive Feature |
| --- | --- |
| Sit vs Stand Gravity Signature | Ratio of the time of occurrence of the negative peak to the time of occurrence of the positive peak in the transient acceleration norm signal. |
| Tilt | The "direction cosines" of Y and Z tilt. Using the median-filtered accelerations, compute the ratio of y and Z accelerations to the total median acceleration at start and end of the transition segment. |
| Sit/Stand Gravity Work Signature Fit Error | The fraction of the energy in the transient YZ acceleration norm that is not captured by the first four gravity work modes. |
| Sit/Stand Balance Lean Signature Fit Error | The fraction of the energy in the transient Y acceleration that is not captured by the first four balance lean modes. |
| Sit/Stand Gravity Work Signature Fit | The "shape" of the coefficients corresponding to the first four gravity work modes. This is computed by dividing the associated four coefficients by the sum of the absolute values of those four coefficients. |
| Sit/Stand Balance Lean Signature Fit | The "shape" of the coefficients corresponding to the first four balance lean modes. This is computed by dividing the associated four coefficients by the sum of the absolute values of those four coefficients. |

While device-coupling implementation and user-posture implementation have been described separately and could be implemented independently, in some embodiments multiple different implementations are combined. In other words, one set of state information (e.g., states of a first Markov Model) is optionally used to provide context information that influences a second set of state information (e.g., states of a second Markov Model). One example is using user-posture state information to condition user-device coupling classifiers. In some embodiments, the features described for device-body coupling above with reference to Table 4 are relevant when the user is either sitting or standing. When the user is engaged in more active motion (e.g., walking or running) a different set of features can be used which take advantage of the relation between motion of the phone while walking based on phone location. For example, the features used to distinguish whether a device is in a user's pocket or a user's hand while a user is walking (e.g., period of movement, damping and/or device swinging in hand) are different from (e.g., includes one or more features not included in) the features used to distinguish whether a device is in a user's pocket or a user's hand while the user is stationary (e.g., detected tremor and/or device orientation). Leveraging this information, the stable-state classifiers can be modified to include one or more sets of conditional classifiers for one or more respective classifications (e.g., a set including an "In Hand Classifier (v1)" for not-walking and an In Hand Classifier (v2) for walking for the "In Hand at Side" vs "In Hand at Front" classification). In some embodiments, only one of the classifiers in each set is used depending on which differentiating condition is most likely (e.g., walking or not-walking). In some embodiments, the output of the classifiers in a set of two or more classifiers for a respective classification are combined by a weighted sum, where the weight is based on the probability of the differentiating condition (e.g., walking or not-walking) determined by a separate posture context algorithm.

A specific example of user-device coupling that is conditioned on posture is described below, however it should be understood that this example is merely illustrative and does not limit the more general concepts described above. In the posture conditioned user-device coupling example, Sensor Data Filter(s) 402 receive Signals from the acceleration channels and break them into low and high pass bands using 51 tap FIR filters, where the low pass band is 0-3.5 Hz and the high pass is 4.5-20 Hz. Sensor Data Filter(s) 402 further generate an envelope of the high pass signal and low pass filter the envelope. Sensor Data Filter(s) 402 optionally resample both the low pass and envelope signal to 12.5 Hz. In some embodiments, in addition to pre-filtered low and high pass filtered traces, Sensor Data Filter(s) 402 extracts a narrow-band walk signal and provides some of the features for phone location determination.

As discussed above, Pre-Classifier 404 acts as a resource manager by managing how frequently the features (e.g., Stable-State Feature Vector or State-Transition Feature Vector), and thus classifiers (e.g., Stable-State Classifiers 408 and/or State-Transition Classifiers 414) and Markov Model 410, are updated. There are two primary ways that Pre-Classifier 404 acts as a resource manager. First, state-transition features are only generated when a transition is determined to be likely by Pre-Classifier 404. Second, stable-state features are generated at a rate corresponding to the current confidence in the state estimate. For example, if Markov Model 410 is very confident in its state estimate and that state has not changed for some time, the update rate will decrease accordingly. It should be noted that a stable-state does not necessarily imply a motionless state, rather a stable-state is a state in which the current state of the device has been unchanged for a period of time. For example, if the device has been sitting on a car seat during a long drive, the device will see forward motion (or even changes in motion as the device speeds up, slows down and turns). However, Pre-Classifier 404 can still go into a low power state where measurement epochs occur infrequently once it has determined that the device is off Body.

Similarly, resource utilization is minimized by reducing the processing requirements of Pre-Classifier 404, so that features that are examined by Pre-Classifier 404 do not cause a large amount of power usage. In some embodiments, Pre-Classifier 404 for the user-device coupling implementation is a simple peak detection algorithm which can be done with very minimal processing resources. Additional power management can be achieved by turning off some of the classifiers when contextual information indicates that the classifiers are not providing useful information. For example, if the device is off Body one or more classifiers, including the posture detection classifiers and, optionally, Pre-Classifier 404 will be turned off.

Multiple State Estimation

As discussed above, in some situations multiple feature vectors (e.g., multiple sets of stable-state features or multiple sets of state-transition features) are generated (e.g., if there is some uncertainty as to a current conditions under which the device is operating). For example, in some situations there is a set of features that are used to determine different device coupling states under a set of conditions where a user is walking and there is a different set of features that are used to determine different device coupling states under a set of conditions where a user is stationary (e.g., standing or sitting). As another example, in some situations there is a set of features that are used to determine different user posture states under a set of conditions where a user is in a first transport state (e.g., in a vehicle) and there is a different set of features that are used to determine different user posture states under a set of conditions where a user is in a second transport state (e.g., not in a vehicle). In such situations, for each of a plurality of user posture states classifiers will identify multiple probability components that correspond to the probability that user is in a respective posture for a plurality of different transport states. For example, when there are multiple probability components that correspond to a probability that the device is in a respective coupling state, $P(X_{i,t}|y_t)$ from equation 4 is computed as the sum of these probability components as shown in equation 7 (separate device coupling probabilities $P(X_t|B_{j,t}, y_t)$ and background condition (transport and posture) probabilities $P(B_{j,t}|y_t)$) or equation 8 (joint device coupling, posture and transport probabilities $P(X_t, B_{j,t}|y_t)$ for different combinations of device coupling, posture and transport), below.

$$P(X_t | y_t) = \sum_j P(X_t | B_{j,t}, y_t) P(B_{j,t} | y_t) \quad (7)$$

$$P(X_t | y_t) = \sum_j P(X_t, B_{j,t} | y_t) \quad (8)$$

In some embodiments, the background condition states are grouped into two sets $S_1=(P, NotInVehicle)$ and $S_2=(P, InVehicle)$, where P represents different possible posture states. In this example, the measurement probability is given by:

$$P(X_t|y_t)=P(X_t|InVehicle, y_t)P(InVehicle|y_t)+P(X_t|NotInVehicle, y_t)P(NotInVehicle|y_t) \quad (9)$$

Where, optionally, $P(X_t|NotInVehicle, y_t)=1-P(InVehicle)$. In this example, $P(X_t|InVehicle, y_t)$ and $P(X_t|NotInVehicle, y_t)$ are computed using sets of conditional device coupling classifiers and $P(InVehicle|y_t)$ and $P(NotInVehicle|y_t)$ are computed by a separate probability estimator for the transport state, such as a separate Transport Markov Model.

In some embodiments, Equation 9 is implemented under the assumption that $P(InVehicle)=0$, and, for a stable state, Stable-State Classifiers 408 produce $P(X_t|NotInVehicle, y_t)$ by combining conditional classifiers for three types of background stable states corresponding to different posture states: $B_1=(Walking, NotInVehicle)$, $B_2=(Standing, NotInVehicle)$, $B_3=(Sitting, NotInVehicle)$. Preclassifier 404 is configured to preclassify two sets of these stable states $S_1=B_1$ (e.g., a "walking stable-state") and $S_2=\{B_2, B_3\}$ (e.g., a "stationary stable-state"). In some situations, stable states are grouped together into sets based on whether they can be evaluated using the same set of features (e.g., states that can be evaluated using the same set of features can be grouped together because there will be minimal additional work to generate features). In some embodiments, when a respective set is preclassified as having a probability above a predefined threshold (e.g., 0, 5, 10, 15, 30 or 50 percent likely or some other reasonable threshold), Preclassifier 404 triggers a feature extraction and classification path corresponding to the respective set. For example, when preclassifier triggers generation of a walking stable state feature set and a stationary stable state feature set, the device generates feature sets for use in determining two probabilities $P(X_t, Walking|NotInVehicle, y_t)$ and $P(X_t|B_{2,t} \vee B_{3,t})$ which are combined as shown in Equation 10.

$$P(X_t | NotInVehicle, y_t) = P(X_t, Walking| NotInVehicle, y_t) + \quad (10)$$
$$P(X_t | B_{2,t} \vee B_{3,t}) P(Standing \vee Sitting| NotInVehicle, y_t)$$

In equation 10, above, the background probability for standing or sitting $P(Standing \vee Sitting|NotInVehicle, y_t)$ is, optionally, computed by summing the total probability that the user is walking and subtracting that probability from 1. For example, as shown in Equations 11-12:

$$P(Walking| NotInVehicle, y_t) = \quad (11)$$
$$\sum_i P(X_{i,t}, Walking| NotInVehicle, y_t)$$

$$P(Standing \vee Sitting| NotInVehicle, y_t) = \quad (12)$$
$$1 - P(Walking| NotInVehicle, y_t)$$

In some embodiments, Equation 9 is implemented without making the assumption that $P(InVehicle)=0$ by adding a classifier for in Vehicle (e.g., by adding classifiers to produce $P(X_t|InVehicle, y_t)$ and $P(InVehicle|y_t)$. Thus, in some embodiments, Preclassifier 404 is configured to preclassify a third set stable states $S_3=\{B_4, B_5, B_6\}$ (e.g., an "in vehicle stable-state"), where $B_4=(Walking, InVehicle)$, $B_5=(Standing, InVehicle)$, $B_6=(Sitting, InVehicle)$. In some embodiments, when a respective set is preclassified as having a probability above a predefined threshold (e.g., 0, 5, 10, 15, 30 or 50 percent likely or some other reasonable threshold), Preclassifier 404 triggers a feature extraction and classification path corresponding to the respective set of features. For example, when preclassifier triggers generation of an in vehicle stable state, the device generates feature sets for determining three probabilities: The probability that the device is in a particular coupling state and a user is walking in a vehicle $P(X_t, \text{Walking}|\text{InVehicle}, y_t)$, the conditional probability that the device is in a particular coupling state given that a user is standing or sitting in a vehicle $P(X_t|\text{Standing}\lor \text{Sitting}, \text{InVehicle}, y_t)=P(X_t|B_5 \lor B_6)$, and the probability that a user is in a vehicle $P(\text{InVehicle})=P(B_4 \lor B_5 \lor B_6)$ which are combined as shown in Equation 13, below.

$$P(X_t \mid \text{InVehicle}, y_t) = P(X_t, \text{Walking}|\ \text{InVehicle}, y_t) + \qquad (13)$$
$$P(X_t \mid B_{5,t} \lor B_{6,t}) P(\text{Standing} \lor \text{Sitting}| \text{InVehicle}, y_t)$$

Equation 13, above, the background probability for standing or sitting $P(\text{Standing}\lor \text{Sitting}|\text{InVehicle}, y_t)$ is, optionally, computed by summing the total probability that the user is walking and subtracting that probability from 1. For example:

$$P(\text{Walking}|\ \text{InVehicle}, y_t) = \sum_i P(X_{i,t}, \text{Walking}|\ \text{InVehicle}, y_t) \qquad (14)$$

$$P(\text{Standing}\lor \text{Sitting}|\ \text{InVehicle}, y_t) = 1 - P(\text{Walking}|\ \text{InVehicle}, y_t) \qquad (15)$$

In many situations, generating different sets of features for a plurality of different conditions under which a device may be operating and combining probability estimations for the different sets of features, as described above, provides a more accurate estimation of the state associated with the device (e.g., posture or device coupling state) than attempting to classify the state associated with the device without taking into account the possible different conditions under which the device is operating.

Recovering from Misclassification

The system and method for determining a state associated with a device has a number of advantages over conventional methods for determining a state associated with a device, however an important advantage is that the method is able to efficiently and effectively recover from misclassifications (e.g., missed state-transition classifications and/or spurious stable-state misclassifications).

If State-Transition Classifiers 414 misclassify a transition with high confidence or Pre-Classifier 404 completely misses a transition, it is possible that the overall model will end up in the "wrong state" for a period of time. There are two ways that the system and method described herein mitigates this effect. First, is through use of priors from Markov Model 404. For example, if the Markov Model 404 is very confident that the phone is in On Table, but the detected transition starts from In Hand (In Hand at Side to Pocket, In Hand at Front to Table), that transition will have a low weight in the Markov Model. While this does not ensure that the new state will be correctly classified, it does prevent a confident misclassification and provides an indication of the uncertainty in the classification, which is more accurate representation of the state of the device than a confident misclassification. In particular, a misclassified transition originating from a low-probability state will typically lead to low confidence in all states (an "unknown" classification), which is more readily recoverable by the stable-state classifiers.

The use of both stable-state classifiers and state-transition classifiers in the state determination process accounts for the fact that no classifier is perfect. Even in the case that the device misses a transition or misclassifies a transition leading to a wrong state in Markov Model 410, the model can still recover and reach the correct state classification using the stable-state classifiers. In some embodiments, the latency of this recovery period is tied to both the degree of misclassification and the confidence of the stable-state measurements. If the misclassification leads to a situation where Markov Model 410 has low confidence in all states and the stable-state classifications have high confidence, Markov Model 410 can recover very quickly (within 1 to 2 stable-state measurements), thus in many situations is better for the model to have an "unknown" (low confidence) classification than to have a high confidence misclassification, because the device can recover from an "unknown" (low confidence) classification more quickly.

Even with well-trained classifiers, periodic misclassifications can occur (especially in the stable-state classifiers) due to things like poor data quality or data uncharacteristic of that contained in the training set. For example, if the device is a phone or media player in an arm band which is not included in the current data collected for user-device coupling, this state may be misclassified as a modeled device coupling state. There are several components of the described system and method that handle these types of spurious/transient misclassifications. First an infinite impulse response that is optionally used to filter classifier outputs helps to suppress spurious misclassifications. Second, in some embodiments, the output of classifiers (e.g., Stable-State Classifiers 408 and/or State-Transition Classifiers 414) is weighted. Rather than simply return a 1 or 0 from an individual classifier, the classifier outputs are converted to probabilities based on the strength of the classification. For a support vector machine model, the strength is determined based on the distance of the features from the margin. For a multi-layer perceptron model, the strength is determined based on the magnitude of the output neurons as well as the relative strength of the different neurons. Third, in some embodiments, multiple classifier models (support vector machines, multi-layer perceptron, decision trees) are used concurrently for the same classification problem, and their results combined to produce the overall classification. By using multiple classifier models concurrently, if one of the classifiers classifies incorrectly but the others do not, this single misclassification is significantly weakened. An advantage of this approach is that the overall system will only produce a strong misclassification if all classifiers agree on the misclassification, which is more unlikely than the occurrence of a misclassification in any single classifier. Finally, Markov Model 410 incorporates prior state information so that even if the voting machine (e.g., Stable-State Classifiers 408 and/or State-Transition Classifiers 414) produces a strong misclassification, this is moderated at Markov Model 410 by the prior state probabilities. For example, if the model is highly confident that the previous state was On Table, it will put less weight on a strong In Pocket classification. However, typically with more than one strong classification, the model will start to produce predicted probabilities of the states associated with the device that are in agreement with the classifiers. As such, the system and method described herein (and further explained below with reference to method 500) provides accurate classifications, efficient and quick recovery from misclassifications and low power usage and thus is particularly useful in mobile applications where quick recovery from misclassifications and low power usage are particularly important.

Attention is now directed to FIGS. 5A-5I, which illustrate a method 500 for determining a state associated with a device, in accordance with some embodiments. Method 500 is, optionally, governed by instructions that are stored in a non-transitory computer readable storage medium and that are executed by one or more processors of one or more computer systems (e.g., Device 102, FIG. 6 or Host 101, FIG. 7). Each of the operations shown in FIGS. 5A-5I typically corresponds to instructions stored in a computer memory or non-transitory computer readable storage medium (e.g., Memory 1110 of Device 102 in FIG. 6 or Memory 1210 of Host 101 in FIG. 7). The computer readable storage medium optionally (and typically) includes a magnetic or optical disk storage device, solid state storage devices such as Flash memory, or other non-volatile memory device or devices. The computer readable instructions stored on the computer readable storage medium typically include one or more of: source code, assembly language code, object code, or other instruction format that is interpreted or executed by one or more processors. In various embodiments, some operations in method 500 are combined and/or the order of some operations is changed from the order shown in FIGS. 5A-5I.

The following operations are performed at a processing apparatus having one or more processors and memory storing one or more programs that, when executed by the one or more processors, cause the respective processing apparatus to perform the method. In some embodiments, the processing apparatus is a component of Device 102 (e.g., the processing apparatus includes the one or more CPU(s) 1102 in FIG. 6). In some embodiments, the processing apparatus is separate from Device 102 (e.g., the processing apparatus includes the one or more CPU(s) 1202 in FIG. 7).

The processing apparatus receives (502) sensor measurements generated by one or more sensors of one or more devices (e.g., one or more sensors 220 of Navigation Sensing Device 102 and/or one or more sensors 230 of Auxiliary Device 106). In some embodiments, the one or more sensors include (504) a respective sensor of the respective device. After receiving the sensor measurements, the processing apparatus pre-classifies (506) the sensor measurements as belonging to one of a plurality of pre-classifications (e.g., coupling pre-classifications such as stable-state or state-transition). For example, as described above with reference to FIGS. 4A-4D, Pre-Classifier 404 determines whether to provide filtered signals to Stable-State Feature Generator 406 or to State-Transition Feature Generator 412 based on whether the pre-classification indicates that the filtered signals correspond to a stable-state or a state-transition.

In some embodiments, the plurality of pre-classifications include (508) a first pre-classification corresponding to a plurality of transition feature types (e.g., state-transition features) associated with identifying a transition between two different states of the respective device; a second pre-classification corresponding to a first subset of a plurality of device-state feature types (e.g., stable-state features) associated with identifying a state of the respective device; and/or a third pre-classification corresponding to a second subset of the plurality of device-state feature types (e.g., stable-state features), where the second subset of device-state feature types is different from the first subset of device-state feature types. In some embodiments, the first subset of device-state feature types enables identification of a device state of the respective device from a first subset of states of the respective device (e.g., device states corresponding to motion of the respective device) and the second subset of device-state feature types enables identification of a device state from a second subset of states of the respective device (e.g., stationary device states of the respective device). For example, processing apparatus has a set of state-transition classifiers (e.g., 414 in FIG. 4A) and two subsets of stable-state classifiers (e.g., 408 in FIG. 4A), where the two subsets of stable-state classifiers include a subset of stable-state classifiers for while the device is in motion (walking, running, driving) and a subset of stable-state classifiers for while the device is stationary (On Table, In Hand, In Pocket). In this example, Pre-Classifier 404 selects one of three different pathways (e.g., state-transition classifiers, device in motion stable-state classifiers, and device stationary stable-state classifiers).

In some embodiments, the processing apparatus obtains (510) context information indicative of a current context of the respective device (e.g., the processing apparatus retrieves or determines/generates context information), and pre-classifies (512) the sensor measurements based at least in part on the current context of the respective device. For example, if there is a high probability that the respective device is Off Body, then the processing apparatus would turn off all subsequent posture-type feature generation, as the processing apparatus will not typically be able to detect the posture of the user if the device is not physically associated with the user. More generally, if the respective device is in the trunk of a car, the processing apparatus can conserve energy by ceasing, at least temporarily, to extract features other than those that are helpful in determining whether or not the respective device has been removed from the trunk of the car. In some embodiments, the current context of the respective device is determined based at least in part on system signals. For example, a system signal indicating that the respective device is connected to a charger optionally prompts the processing apparatus to forgo generating features related to user body posture. In some embodiments, the current context of the respective device is determined based on stored information about a current user of the respective device (e.g., some classifiers are turned on, turned off, or modified if a user is male or is over 200 lbs).

In some embodiments, pre-classifying the sensor measurements includes (514) extracting features of one or more pre-classification feature types from the sensor measurements, and extracting features of the pre-classification feature types from the sensor measurements is more resource efficient than extracting features of the one or more selected feature types from the sensor measurements (e.g., the pre-classification features are generated using low-power algorithms to provide a rough estimate of the general type of behavior currently exhibited by the respective device). For example, extracting the same quantity of features of the pre-classification feature types would take a smaller amount of CPU resources than extracting a similar quantity of features of the selected feature types. In some embodiments, extracting features of the pre-classification feature types enables the processing apparatus to forgo extracting features of one or more unselected feature types, thereby reducing the CPU usage and power usage due to extracting features from the sensor measurements and conserving battery life if the respective device is battery operated. In some embodiments, the pre-classification feature types include peak detection on frequency filtered sensor measurements. In some embodiments, the pre-classification feature types include threshold detection on frequency filtered sensor measurements (e.g., the "Derivative Low Pass" signal in Table 1). In some embodiments, the pre-classification feature types include peak detection on envelope filtered sensor measurements (e.g., the "Envelope Low Pass" signal and the "Envelope High Pass" signal in Table 1). In some embodiments, the pre-classification feature types include threshold detection on envelope filtered sensor measurements (e.g., the "Envelope Low Pass" signal and the "Envelope High Pass" signal in Table 1).

After pre-classifying the sensor measurements, the processing apparatus selects (516) one or more feature types to extract from the sensor measurements based at least in part on the pre-classification of the sensor measurements (e.g., the processing apparatus determines whether to extract stable-state features or transition features). For example, as described above with respect to FIGS. 4A-4D, Pre-Classifier 404 determines whether to transmit the filtered signals to Stable-State Feature Generator 406 or State-Transition Feature Generator 412. In some embodiments, the processing apparatus selects (518) between a first set of feature types and a second set of feature types. In some implementations, the first set of feature types is (520) different from the second set of feature types. In some implementations, the first set of feature types includes (522) a respective feature type from the second set of feature types. In some implementations, the first set of feature types includes (524) a respective feature type not included in the second set of feature types. In some implementations, the first set of feature types and the second set of feature types are (526) mutually exclusive.

In some embodiments, the first set of feature types are feature types that enable (528) classification of a coupling state of the respective device (e.g., a Stable-State Feature Vector for processing by Stable-State Classifiers 408 as described in greater detail above with reference to FIGS. 4A-4D). In some embodiments, the first set of feature types include device orientation angle of the respective device (e.g., the "Tilt Angle" feature in Table 2c). In some embodiments, the first set of feature types include device orientation variation of the respective device (e.g., the "Tilt Variation and High Frequency Variation" feature in Table 2b). In some embodiments, the first set of feature types include correlation of movement of the respective device along two or more axes (e.g., the "Coordinated Movement" features in Table 2b). In some embodiments, the first set of feature types include bandwidth of a sensor measurement signal (e.g., the "Signal Bandwidth" feature in Table 2b). In some embodiments, the first set of feature types include variability in bandwidth of a sensor measurement signal (e.g., the "Variability in Signal Bandwidth" feature in Table 2b). In some embodiments, the first set of feature types include spectral energy of a sensor measurement signal (e.g., the "Spectral Energy" feature in Table 2a).

In some embodiments, the second set of feature types are feature types that enable (530) classification of a transition between two different coupling states of the respective device (e.g., a State-Transition Feature Vector for processing by State-Transition Classifiers 412 as described in greater detail above with reference to FIGS. 4A-4D). In some embodiments, the second set of feature types include device orientation angle of the respective device (e.g., the "Tilt Angle and Tilt Variation" feature in Table 3). In some embodiments, the second set of feature types include device orientation variation of the respective device (e.g., the "Tilt Angle and Tilt Variation" feature in Table 3). In some embodiments, the second set of feature types include mutual information between movement of the respective device along two or more axes (e.g., the "Coordinated Motion (high pass, mutual information) and Coordinated Motion (low pass, mutual information)" features in Table 3). In some embodiments, the second set of feature types include correlation of movement of the respective device along two or more axes (e.g., the "Coordinated Motion (high pass, correlation) and Coordinated Motion (low pass, correlation)" features in Table 3). In some embodiments, the second set of feature types include maximum energy of a sensor measurement signal (e.g., the "Max Energy and Time of Max Energy" feature in Table 3). In some embodiments, the second set of feature types include spectral energy of a sensor measurement signal (e.g., the "Spectral Energy" feature in Table 3). In some embodiments, the second set of feature types include device orientation variation extrema of the respective device (e.g., the "Tilt Variation Extrema and Associated Time" feature in Table 3).

In some embodiments, the first set of feature types includes (532) features adapted for determining a state of the respective device while the respective device is stationary and the second set of feature types includes features adapted for determining a state of the respective device while the respective device is in motion. In some embodiments, the feature selection process performed by the pre-classifier includes not just selecting between stable or transition features, but also selecting between different types of stable features or transition features. For example, if the user is walking, the processing apparatus generates a different set of "stable" features for device coupling than if the user is standing still. In some implementations, determining which set of features to use is based in part on other context information.

In some embodiments, the processing apparatus performs different operations based on whether the first sensor measurements correspond to a first pre-classification or a second pre-classification (e.g., whether the Filtered Signals correspond to a Stable-State or a State-Transition, as described above with reference to FIGS. 4A-4D). In accordance with a determination (e.g., during the pre-classification) that the sensor measurements correspond to a first (e.g., coupling-stable) pre-classification (534), the processing apparatus selects (536) a first set of feature types as the one or more selected feature types and, optionally, forgoes (538) extracting features of one or more of the second set of feature types while extracting features of the first set of feature types. In contrast, in accordance with a determination (e.g., during the pre-classification) that the set of sensor measurements correspond to a second (e.g., coupling-transition) pre-classification (540), the processing apparatus selects (542) a second set of feature types as the one or more selected feature types (different from the first set of feature types) and, optionally, forgoes (544) extracting features of one or more of the first set of feature types while extracting features of the second set of feature types. In other words, in some embodiments, the processing apparatus does not extract both stable-state and transition features at the same time, which reduces the processing and energy requirements of the processing apparatus, thereby conserving energy.

In some embodiments, prior to extracting features of the one or more feature types selected based on the pre-classification, the processing apparatus schedules (546) extraction of one or more features. In some embodiments, the processing apparatus schedules (548) extraction of features of a first subset of a plurality of feature types, where the first subset of feature types includes (550) the one or more feature types selected based on the pre-classification. In some embodiments, the processing apparatus also schedules (552) extraction of features of a second subset of the plurality of feature types, where the second subset of feature types includes (552) feature types other than the one or more feature types selected based on the pre-classification. In some embodiments, the extraction of features of the second subset of feature types is scheduled to occur after (556) the extraction of features of the first subset of feature types. In some embodiments, the extraction of features of the second subset of feature types is (558) subject to cancellation.

After selecting the one or more feature types to extract, the processing apparatus extracts (560) features of the one or more selected feature types from the sensor measurements. In some embodiments, the one or more selected feature types includes (562) a respective feature type that provides an approximation of frequency bandwidth information for a respective sensor-measurement signal that corresponds to sensor measurements collected over time, and extracting features of the one or more selected feature types from the sensor measurements includes extracting features of the respective feature type from the respective sensor-measurement signal in the time domain without converting the respective sensor-measurement signal into the frequency-domain. For example, the "Variability in Signal Bandwidth" and "Signal Bandwidth" features described with reference to Table 2b provide information about the sensor-measurement signal in the time domain without converting the respective sensor-measurement signal into the frequency-domain.

In some embodiments, the processing apparatus extracts the features of the one or more selected feature types by extracting (564) features of a first subset of a plurality of feature types, where the first subset includes the one or more feature types selected based on the pre-classification. After extracting the features of the first subset, the processing apparatus determines (566) whether the features extracted from the first subset of feature types are consistent with the pre-classification. In accordance with a determination that the features extracted from the first subset of feature types are not (568) consistent with the pre-classification, the processing apparatus extracts (569) features of a second subset of feature types that includes feature types other than the one or more feature types selected based on the pre-classification. In contrast, in accordance with a determination that the features extracted from the first subset of feature types are (570) consistent with the pre-classification, the processing apparatus forgoes (571) extracting features of the second subset of feature types. In some embodiments, the second subset of feature types start to be extracted before extraction of the second subset of feature types is cancelled. In some embodiments, the features of the first subset of feature types and the features of the second subset of feature types are features to be extracted from sensor measurements from a same respective measurement epoch.

Thus, in some implementations, instead of Pre-classifier 404 making a final determination as to whether to extract either stable-state features or state-transition features, Pre-Classifier 404, instead schedules the extraction of both stable-state features and state-transition features and schedule extraction of the type of features that are more likely to be useful based on the pre-classification of the filtered signals (e.g., by placing instructions to extract the features in a work queue of tasks assigned to one or more processors for execution). In some implementations, once the features of the first subset of feature types (e.g., stable-state features or state-transition features) have been extracted, if it is determined that the pre-classification was correct, then features of the second subset of features types (e.g., state-transition features or stable-state features, respectively) need not be extracted and extraction of features of the second subset of feature types is, optionally, cancelled (e.g., removed from the work queue) by the processing apparatus. In contrast, once the features of the first subset of feature types have been extracted, if it is determined that the pre-classification was incorrect, then extraction of features of the second subset of feature types proceeds without having to schedule extraction of features of the second subset of feature types (e.g., because the extraction of features of the second subset of feature types was previously scheduled). In some embodiments the pre-classification is determined to be correct when the features of the first subset of feature types can be successfully used (e.g., by Stable-State Classifiers 408 or State-Transition Classifiers 414) to generate information (e.g., transition probabilities or state probabilities for updating Markov Model 410) for determining a state of the device.

For example, if the pre-classification indicates that the device is likely undergoing a state-transition, the processing apparatus optionally schedules extraction of state-transition features followed by extraction of stable-state features. In this example, if the state-transition features indicate that the device is undergoing a recognizable transition, then the processing apparatus optionally cancels extraction of the stable-state features, while if the state-transition features indicate that the device is not undergoing a transition, then the processing apparatus optionally continues with extraction of the stable-state features, and, optionally use the stable-state features to attempt to identify a recognizable state of the device. As another example, if the pre-classification indicates that the device is likely in a stable-state, the processing apparatus optionally schedules extraction of stable-state features followed by extraction of state-transition features. In this example, if the stable-state features indicate that the device is in a recognizable state, then the processing apparatus optionally cancels extraction of the state-transition features, while if the stable-state features indicate that the device is not in a recognizable state, then the processing apparatus optionally continues with extraction of the state-transition features, and, optionally uses the state-transition features to attempt to identify a recognizable transition. An advantage of scheduling extraction of both state-transition features and stable-state features is that, when the processing apparatus mistakenly pre-classifies a state of the device and thus requests extraction of an incorrect type of features, there is a shorter delay to get the correct type of features than if the processing apparatus were to schedule extraction of the correct type of features after the error was identified. However, by scheduling extraction of the features in sequence, the computational efficiency (and energy efficiency) of the system can be preserved by cancelling extraction of features that are not needed when the pre-classification is determined to be correct based on previously extracted features (e.g., the features of the first type of features).

After extracting the features of the one or more selected feature types, the processing apparatus determines (572) a state of a respective device of the one or more devices in accordance with a classification of the sensor measurements determined based on the one or more features extracted from the sensor measurements (e.g., using Markov Model 410 described in greater detail above with reference to FIGS. 4A-4D). In some embodiments, the state of the respective device is a sensor-interpretation state that is used to interpret sensor measurements from sensors of the respective device. In some embodiments, states for a plurality of the one or more devices are determined by the processing apparatus. In some embodiments, the state of the respective device is (573) a physical property of the respective device (e.g., a coupling state of the respective device or a navigational state of the respective device). In some embodiments, the state of the respective device is (574) a state of an environment of the respective device (e.g., a state of an entity associated with the respective device or a state of an environment surrounding the respective device such whether the respective device is in a car or an elevator). In some embodiments, the state of the respective device is (575) a state of an entity associated with the respective device (e.g., a posture of a user of the device).

In some embodiments, the one or more devices include (576) a first device (e.g., Navigation Sensing Device 102) and a second device (e.g., Auxiliary Device 106). For example, the two devices are optionally, a smartphone with a plurality of sensors and a Bluetooth headset with one or more sensors; two smartphones that are in communication with each other; or with a remote computer such as a set top box or home entertainment system. In some of these embodiments, the processing apparatus determines (578) a state of the first device in accordance with a classification of the sensor measurements determined based on the one or more features extracted from the sensor measurements and determines (579) a state of the second device in accordance with the classification of the sensor measurements determined based on the one or more features extracted from the sensor measurements. In other words, a state of the first device is determined based at least in part on sensor measurements from the second device (e.g., in addition to one or more sensor measurements from the first device). In some embodiments the second device provides the processing apparatus with processes signal features. In some embodiments, the second device provides the processing apparatus with raw sensor data. In some embodiments, the state of the second device is determined (580) based at least in part on the state of the first device and/or based on sensor measurements from one or more sensors of the first device.

In some embodiments, pre-classifying the sensor measurements includes (581) identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions; extracting the features includes extracting the first set of features and extracting the second set of features; and determining the state of the respective device includes determining the state of the respective device in accordance with the first set of features and the second set of features. In some embodiments, the first set of conditions is "InVehicle" and the second set of conditions is "NotInVehicle." In some embodiments, the first set of conditions is "Walking" and the second set of conditions is "Stationary." While the examples described herein specifically identify two feature sets associated with a respective pre-classification, in some situations a larger number of feature sets (e.g., 3, 4, 5 or more feature sets) are associated with a respective pre-classification (e.g., where the pre-classification corresponds to a larger number of possible conditions under which the device is operating). For example, in some situations, a pre-classification indicates that a device is in a stable state but indicates that it is uncertain whether the device is associated with a walking user or a stationary user and thus the pre-classification will trigger the generation of a set of "Walking" stable-state features and a set of "Stationary" stable-state features (e.g., as described in greater detail above with reference to Equations 7-13). As another example, in some situations, a pre-classification indicates that a device is in a state transition but indicates that it is uncertain whether the device is associated with a walking user or a stationary user and thus the pre-classification will trigger the generation of a set of "Walking" state-transition features and a set of "Stationary" state-transition features.

In some embodiments, pre-classifying the sensor measurements includes identifying the sensor measurements as belonging to one of a plurality of coupling pre-classifications and determining the state of the respective device includes determining (582) a coupling state of the respective device in accordance with a coupling classification of the sensor measurements determined based on the one or more features extracted from the sensor measurements. In other words, at least some of the features that are used to pre-classify the sensor measurements are extracted from same sensor measurements from which the features that are used to classify the state of the device are made. For example, as described in greater detail above with reference to FIGS. 4A-4D, the filtered signals are used by both Pre-Classifier 404 and the classifiers (e.g., Stable-State Feature Generator 406 or State-Transition Feature Generator 412, depending on the pre-classification of the filtered signals).

In some embodiments, the coupling state of the respective device includes (583) a plurality of coupling-stable states corresponding to a coupling between the respective device and an entity (e.g., an owner/user of the respective device) associated with the respective device. For example, in FIG. 4B, Markov Model 410 includes at least four coupling states, "On Table," "In Hand at Side," "In Hand at Front," and "In Pocket." In some embodiments, the coupling state of the respective device includes (584) a plurality of coupling-transition states corresponding to a transition between two of the coupling-stable states. For example, in FIG. 4B, Markov Model 410 includes at least 12 transitions between different coupling states.

In some embodiments, determining the state of the respective device includes updating (586) a Markov Model, where the Markov Model includes: a plurality of model states corresponding to states of the respective device; and (e.g., coupling-stable states of the respective device) a plurality of sets of transition probabilities between the plurality of model states. For example, Markov Model 410 in FIG. 4B includes at least four model states ($X_1$, $X_2$, $X_3$ and $X_4$) and at least sixteen transitions (e.g., $T_1$, $T_2$, $T_3$, $T_4$, $T_5$, $T_6$, $T_7$, $T_8$, $T_9$, $T_{10}$, $T_{11}$, $T_{12}$, $T_{13}$, $T_{14}$, $T_{14}$, $T_{15}$, and $T_{16}$). In some embodiments, in accordance with a determination (e.g., during the pre-classification) that the sensor measurements correspond to a first (e.g., coupling-stable) pre-classification, the processing apparatus updates (587) one or more model states in the Markov Model in accordance with a first set of transition probabilities (e.g., a first state transition matrix for the Markov Model corresponding to the first pre-classification). For example, as described above with reference to equations 3-4, when Pre-Classifier 404 determines that the state associated with the device is in stable-state, stable-state features are produced and used to generate a measurement probability $P(X_{i,t}|y_t)$ that is combined with a model-predicted probability $\tilde{P}(X_{i,t})$ (generated based on the first set of transition probabilities) to generate a combined probability of the various model states.

In some embodiments, in accordance with a determination (e.g., during the pre-classification) that the set of sensor measurements correspond to a second (e.g., coupling-transition) pre-classification, the processing apparatus updates (588) one or more model states in the Markov Model in accordance with a second set of transition probabilities different from the first set of transition probabilities (e.g., a second state transition matrix for the Markov Model corresponding to the second pre-classification). In some embodiments, the second set of transition probabilities is derived, at least in part, from the features selected by the pre-classifier. For example, as described above with reference to equation 5, when Pre-Classifier 404 determines that the state associated with the device is in transition, state-transition features are produced and used to generate a measurement-based state transition matrix (e.g., State-Transition Markov Model Transition Matrix 422 in FIG. 4B) for use in place of a stable-state transition matrix (e.g., Stable-State Transition Markov Model Transition Matrix 420 in FIG. 4B). After the measurement-based state transition matrix is generated, a model update is performed using the measurement-based state transition matrix (e.g., in accordance with equation 6). In other words, in some embodiments, the same model states are modeled in the Markov Model for both a stable-state mode and a state-transition mode, but the transition probabilities of the Markov Model are changed in accordance with depending on the pre-classification of the respective device.

In some embodiments, after determining the state of the respective device, the processing apparatus adjusts (590) operation of the respective device in accordance with the determined state of the respective device. For example, the processing apparatus turns a display on when a device is removed from a pocket or bag or turns a display off when the respective device is placed in a pocket or bag. As another example, the processing apparatus recalibrates sensors of the respective device when the respective is picked up from a table; locks the respective device when the respective device is placed on a table, in a pocket, or in a bag; and/or unlocks the respective device when the respective device is picked up from a table, removed from a pocket, or removed from a bag. As another example, the processing apparatus enables motion tracking features when the respective device is physically associated with the user and/or disables motion tracking features when the respective device is placed on a stationary object such as a table.

In some embodiments, the processing apparatus repeats (592) the receiving sensor measurements, pre-classifying sensor measurements, selecting one or more feature types, extracting features and determining the state of the respective device for a plurality of measurement epochs. In some embodiments, a state of the respective device determined in a prior measurement epoch is used (593) as a factor in determining a state in a current measurement epoch. In some embodiments, a frequency of the measurement epochs is variable and is determined (594) at least in part based on a coupling pre-classification of the sensor measurements (e.g., stable-state or transition), a probability of a coupling state of the respective device determined in a prior measurement epoch (e.g., a degree of certainty of a coupling state), and/or a stability of a current coupling state of the respective device (e.g., length of time that a coupling state has remained at high probability). In some embodiments, the processing apparatus increases an amount of time between measurement epochs when there is greater certainty and/or stability in the state associated with the device. In some embodiments, the processing apparatus decreases an amount of time between measurement epochs when there is less certainty and/or stability in the state associated with the device.

In some embodiments, the plurality of epochs include (596) a first epoch and a second epoch, and during the first epoch: the sensor measurements are determined to correspond to a coupling-stable pre-classification and a first set of feature types corresponding to the coupling-stable pre-classification are selected as the one or more selected feature types. In contrast, during the second epoch the sensor measurements are determined to correspond to a coupling-transition pre-classification and a second set of feature types corresponding to the coupling-transition pre-classification are selected as the one or more selected feature types, where the first set of feature types is different from the second set of feature types. In other words the processing apparatus selects between different features to generate based upon conditions at the device during successive measurement epochs. Thus, when the device is in a stable-state, stable-state features are generated and when the state of the device is in transition, state-transition features are generated, thereby conserving energy and processing power.

It should be understood that the particular order in which the operations in FIGS. 5A-5I have been described are merely exemplary and are not intended to indicate that the described order is the only order in which the operations could be performed. One of ordinary skill in the art would recognize various ways to reorder the operations described herein.

System Structure

Figure 6:
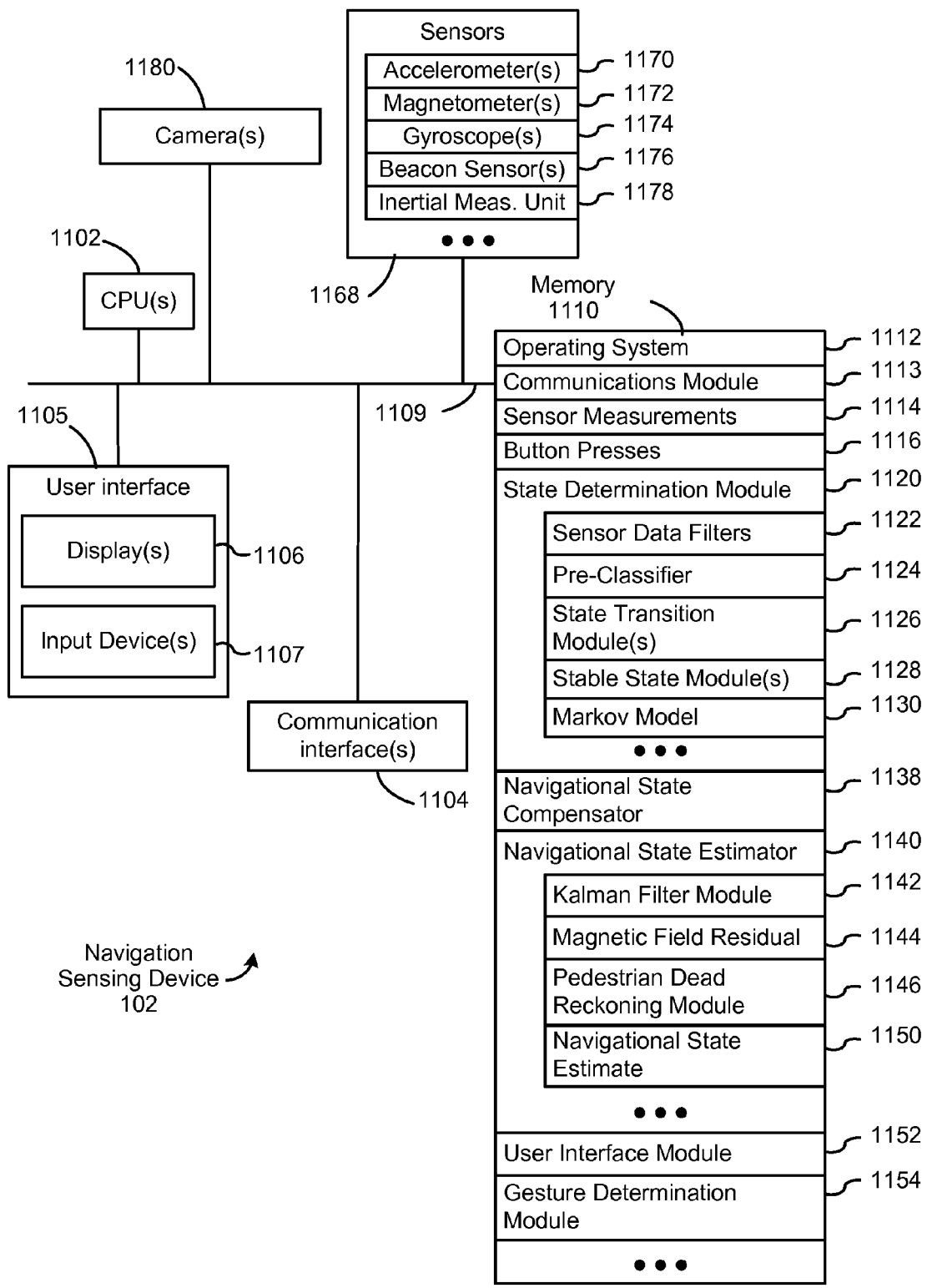
FIG. 6 presents a block diagram of an example navigation sensing device, according to some embodiments.

FIG. 6 is a block diagram of Navigation sensing Device 102 (herein "Device 102"). Device 102 typically includes one or more processing units (CPUs) 1102, one or more network or other Communications Interfaces 1104 (e.g., a wireless communication interface, as described above with reference to FIG. 1), Memory 1110, Sensors 1168 (e.g., Sensors 220 such as one or more Accelerometers 1170, Magnetometers 1172, Gyroscopes 1174, Beacon Sensors 1176, Inertial Measurement Units 1178, Thermometers, Barometers, and/or Proximity Sensors, etc.), one or more Cameras 1180, and one or more Communication Buses 1109 for interconnecting these components. In some embodiments, Communications Interfaces 1104 include a transmitter for transmitting information, such as accelerometer and magnetometer measurements, and/or the computed navigational state of Device 102, and/or other information to Host 101. Communication buses 1109 typically include circuitry (sometimes called a chipset) that interconnects and controls communications between system components. Device 102 optionally includes user interface 1105 comprising Display 1106 (e.g., Display 104 in FIG. 1) and Input Devices 1107 (e.g., keypads, buttons, etc.). Memory 1110 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 1110 optionally includes one or more storage devices remotely located from the CPU(s) 1102. Memory 1110, or alternately the non-volatile memory device(s) within Memory 1110, comprises a non-transitory computer readable storage medium. In some embodiments, Memory 1110 stores the following programs, modules and data structures, or a subset thereof:

- Operating System 1112 that includes procedures for handling various basic system services and for performing hardware dependent tasks;
- Communication Module 1113 that is used for connecting Device 102 to Host 101 and/or Device 106 via Communication Network Interface(s) 1104 (wired or wireless); Communication Module 1113 is optionally adapted for connecting Device 102 to one or more communication networks, such as the Internet, other wide area networks, local area networks, metropolitan area networks, and so on;
- Sensor Measurements 1114 (e.g., data representing accelerometer measurements, magnetometer measurements, gyroscope measurements, global positioning system measurements, beacon sensor measurements, inertial measurement unit measurements, thermometer measurements, atmospheric pressure measurements, proximity measurements, etc.);
- data representing Button Presses 1116;
- State Determination Module 1120 for determining a state associated with Device 102 (e.g., a state of Device 102 such as a navigational state and/or a state of an environment in which Device 102 is currently located), optionally including:

Sensor Data Filters 1122 for filtering raw sensor data generated by the sensors (e.g., Sensor Data Filter(s) 402 in FIGS. 4A-4D);

Pre-Classifier 1124 for determining, based on the sensor data (e.g., as filtered by Sensor Data Filters 1122), which types of features to generate based on the sensor data (e.g., Pre-Classifier 404 in FIGS. 4A-4D) and, optionally, scheduling features to be extracted;

State Transition Module(s) 1126 for generating (e.g., via State-Transition Feature Generator(s) 412 in FIGS. 4A-4D) state-transition features associated with state transitions between different states associated with Device 102 based on the sensor data, and applying (e.g., via State-Transition Classifier(s) 414 in FIGS. 4A-4D) state-transition classifiers to the state-transition features (e.g., for use in updating model transition probabilities of a probabilistic model such as Markov Model 1130);

Stable State Module(s) 1128 for generating (e.g., via Stable-State Feature Generator(s) 406 in FIGS. 4A-4D) stable-state features associated with a stable state associated with Device 102 based on the sensor data, and applying (e.g., via Stable-State Classifier(s) 408 in FIGS. 4A-4D) stable-state classifiers to the features (e.g., for use in updating model state probabilities of a probabilistic model such as Markov Model 1130); and Markov Model 1130 for updating probabilities of states associated with Device 102 in accordance with model state probabilities and model transition probabilities (e.g., Markov Model 410 in FIGS. 4A-4D);

Navigational State Compensator 1138 for determining a fixed compensation (e.g., a rotational offset) for compensating for drift in the navigational state estimate;

Navigation State Estimator 1140 for estimating navigational states of Device 102, optionally including:

Kalman Filter Module 1142 that determines the attitude of Device 102, as described in U.S. Pat. Pub. No. 2010/0174506 Equations 8-29, wherein the Kalman filter module includes: a sensor model (e.g., the sensor model described in Equations 28-29 of U.S. Pat. Pub. No. 2010/0174506), a dynamics model (e.g., the dynamics model described in Equations 15-21 of U.S. Pat. Pub. No. 2010/0174506), a predict module that performs the predict phase operations of the Kalman filter, an update module that performs the update operations of the Kalman filter, a state vector of the Kalman filter (e.g., the state vector $\hat{x}$ in Equation 10 of U.S. Pat. Pub. No. 2010/0174506), a mapping, Kalman filter matrices, and attitude estimates (e.g., the attitude estimates as obtained from the quaternion in the state vector $\hat{x}$ in Equation 10 of U.S. Pat. Pub. No. 2010/0174506);

Magnetic Field Residual 1144 that is indicative of a difference between a magnetic field detected based on measurements from Magnetometer(s) 1172 and a magnetic field estimated based on Kalman Filter Module 1142;

Pedestrian Dead Reckoning Module 1146, for determining a direction of motion of the entity and updating a position of the device in accordance with the direction of motion of the entity, stride length, and stride count (additional details regarding pedestrian dead reckoning can be found in A. Jimenez, F. Seco, C. Prieto, and J. Guevara, "A comparison of Pedestrian Dead-Reckoning algorithms using a low-cost MEMS IMU," IEEE International Symposium on Intelligent Signal Processing 26-28 Aug. 2009, p. 37-42, which is incorporated herein by reference in its entirety); and data representing Navigational State Estimate 1150 (e.g., an estimate of the position and/or attitude of Device 102).

optionally, User Interface Module 1152 that receives commands from the user via Input Device(s) 1107 and generates user interface objects in Display(s) 1106 in accordance with the commands and the navigational state of Device 102, User Interface Module 1152 optionally includes one or more of: a cursor position module for determining a cursor position for a cursor to be displayed in a user interface in accordance with changes in a navigational state of the navigation sensing device, an augmented reality module for determining positions of one or more user interface objects to be displayed overlaying a dynamic background such as a camera output in accordance with changes in a navigational state of the navigation sensing device, a virtual world module for determining a portion of a larger user interface (a portion of a virtual world) to be displayed in accordance with changes in a navigational state of the navigation sensing device, a pedestrian dead reckoning module for tracking movement of Device 102 over time, and other application specific user interface modules; and optionally, Gesture Determination Module 1154 for determining gestures in accordance with detected changes in the navigational state of Device 102.

It is noted that in some of the embodiments described above, Device 102 does not include a Gesture Determination Module 1154, because gesture determination is performed by Host 101. In some embodiments described above, Device 102 also does not include State Determination Module 1120, Navigational State Estimator 1140 and User Interface Module because Device 102 transmits Sensor Measurements 1114 and, optionally, data representing Button Presses 1116 to a Host 101 at which a navigational state of Device 102 is determined.

Each of the above identified elements may be stored in one or more of the previously mentioned memory devices, and each of the above identified programs or modules corresponds to a set of instructions for performing a function described above. The set of instructions can be executed by one or more processors (e.g., CPUs 1102). The above identified modules or programs (i.e., sets of instructions) need not be implemented as separate software programs, procedures or modules, and thus various subsets of these modules may be combined or otherwise re-arranged in various embodiments. In some embodiments, Memory 1110 may store a subset of the modules and data structures identified above. Furthermore, Memory 1110 may store additional modules and data structures not described above.

Although FIG. 6 shows a "Navigation sensing Device 102," FIG. 6 is intended more as functional description of the various features which may be present in a navigation sensing device. In practice, and as recognized by those of ordinary skill in the art, items shown separately could be combined and some items could be separated.

Figure 7:
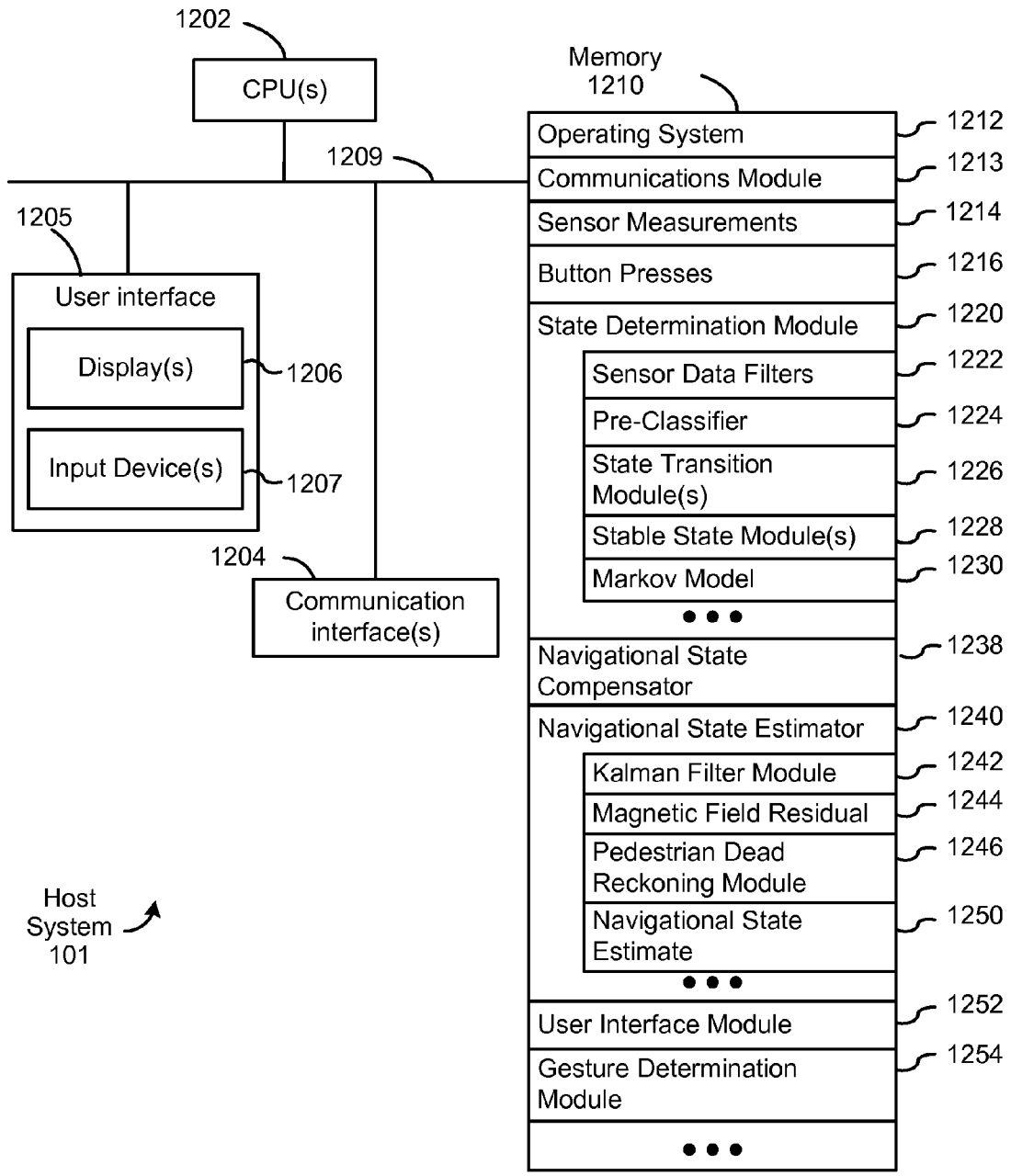
FIG. 7 presents a block diagram of an example host computer system, according to some embodiments.

FIG. 7 is a block diagram of Host Computer System 101 (herein "Host 101"). Host 101 typically includes one or more processing units (CPUs) 1202, one or more network or other Communications Interfaces 1204 (e.g., any of the wireless interfaces described above with reference to FIG. 1), Memory 1210, and one or more Communication Buses 1209 for interconnecting these components. In some embodiments, Communication Interfaces 1204 include a receiver for receiving information, such as accelerometer and magnetometer measurements, and/or the computed attitude of a navigation sensing device (e.g., Device 102), and/or other information from Device 102. Communication Buses 1209 optionally include circuitry (sometimes called a chipset) that interconnects and controls communications between system components. Host 101 optionally includes a User Interface 1205 comprising a Display 1206 (e.g., Display 104 in FIG. 1) and Input Devices 1207 (e.g., a navigation sensing device such as a multi-dimensional pointer, a mouse, a keyboard, a trackpad, a trackball, a keypad, buttons, etc.). Memory 1210 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 1210 optionally includes one or more storage devices remotely located from the CPU(s) 1202. Memory 1210, or alternately the non-volatile memory device(s) within Memory 1210, comprises a non-transitory computer readable storage medium. In some embodiments, Memory 1210 stores the following programs, modules and data structures, or a subset thereof:

- Operating System 1212 that includes procedures for handling various basic system services and for performing hardware dependent tasks;
- Communication Module 1213 that is used for connecting Host 101 to Device 102 and/or Device 106, and/or other devices or systems via Communication Network Interface(s) 1204 (wired or wireless), and for connecting Host 101 to one or more communication networks, such as the Internet, other wide area networks, local area networks, metropolitan area networks, and so on;
- Sensor Measurements 1214 (e.g., data representing accelerometer measurements, magnetometer measurements, gyroscope measurements, global positioning system measurements, beacon sensor measurements, inertial measurement unit measurements, thermometer measurements, atmospheric pressure measurements, proximity measurements, etc.);
- data representing Button Presses 1216;
- State Determination Module 1220 for determining a state associated with Device 102 (e.g., a state of Device 102 such as a navigational state and/or a state of an environment in which Device 102 is currently located), optionally including:
  - Sensor Data Filters 1222 for filtering raw sensor data generated by the sensors of Device 102 (e.g., Sensor Data Filter(s) 402 in FIGS. 4A-4D);
  - Pre-Classifier 1224 for determining, based on the sensor data (e.g., as filtered by Sensor Data Filters 1222), which types of features to generate based on the sensor data (e.g., Pre-Classifier 404 in FIGS. 4A-4D) and, optionally, scheduling features to be extracted;
  - State Transition Module(s) 1226 for generating (e.g., via State-Transition Feature Generator(s) 412 in FIGS. 4A-4D) state-transition features associated with state transitions between different states associated with Device 102 based on the sensor data, and applying (e.g., via State-Transition Classifier(s) 414 in FIGS. 4A-4D) state-transition classifiers to the state-transition features (e.g., for use in updating model transition probabilities of a probabilistic model such as Markov Model 1230);
  - Stable State Module(s) 1228 for generating (e.g., via Stable-State Feature Generator(s) 406 in FIGS. 4A-4D) stable-state features associated with a stable state associated with Device 102 based on the sensor data, and applying (e.g., via Stable-State Classifier(s) 408 in FIGS. 4A-4D) stable-state classifiers to the features (e.g., for use in updating model state probabilities of a probabilistic model such as Markov Model 1230); and
  - Markov Model 1230 for updating probabilities of states associated with Device 102 in accordance with model state probabilities and model transition probabilities (e.g., Markov Model 410 in FIGS. 4A-4D);
- Navigational State Compensator 1238 for determining a fixed compensation (e.g., a rotational offset) for compensating for drift in the navigational state estimate of Device 102;
- Navigation State Estimator 1240 for estimating navigational states of Device 102, optionally including:
  - Kalman Filter Module 1242 that determines the attitude of Device 102, as described in U.S. Pat. Pub. No. 2010/0174506 Equations 8-29, wherein the Kalman filter module includes: a sensor model (e.g., the sensor model described in Equations 28-29 of U.S. Pat. Pub. No. 2010/0174506), a dynamics model (e.g., the dynamics model described in Equations 15-21 of U.S. Pat. Pub. No. 2010/0174506), a predict module that performs the predict phase operations of the Kalman filter, an update module that performs the update operations of the Kalman filter, a state vector of the Kalman filter (e.g., the state vector $\hat{x}$ in Equation 10 of U.S. Pat. Pub. No. 2010/0174506), a mapping, Kalman filter matrices, and attitude estimates (e.g., the attitude estimates as obtained from the quaternion in the state vector $\hat{x}$ in Equation 10 of U.S. Pat. Pub. No. 2010/0174506);
  - Magnetic Field Residual 1244 that is indicative of a difference between a magnetic field detected based on measurements from Magnetometer(s) 1272 and a magnetic field estimated based on Kalman Filter Module 1242;
  - Pedestrian Dead Reckoning Module 1246, for determining a direction of motion of the entity and updating a position of the device in accordance with the direction of motion of the entity, stride length and stride count; and
  - data representing Navigational State Estimate 1250 (e.g., an estimate of the position and/or attitude of Device 102).
- optionally, User Interface Module 1252 that receives commands from the user via Input Device(s) 1207 and generates user interface objects in Display(s) 1206 in accordance with the commands and the navigational state of Device 102, User Interface Module 1252 optionally includes one or more of: a cursor position module for determining a cursor position for a cursor to be displayed in a user interface in accordance with changes in a navigational state of the navigation sensing device, an augmented reality module for determining positions of one or more user interface objects to be displayed overlaying a dynamic background such as a camera output in accordance with changes in a navigational state of the navigation sensing device, a virtual world module for determining a portion of a larger user interface (a portion of a virtual world) to be displayed in accordance with changes in a navigational state of the navigation sensing device, a pedestrian dead reckoning module for tracking movement of Device 102 over time, and other application specific user interface modules; and optionally, Gesture Determination Module 1254 for determining gestures in accordance with detected changes in the navigational state of Device 102.

It is noted that in some of the embodiments described above, Host 101 does not store data representing Sensor Measurements 1214, because sensor measurements of Device 102 are processed at Device 102, which sends data representing Navigational State Estimate 1250 to Host 101. In other embodiments, Device 102 sends data representing Sensor Measurements 1214 to Host 101, in which case the modules for processing that data are present in Host 101.

Each of the above identified elements may be stored in one or more of the previously mentioned memory devices, and each of the above identified programs or modules corresponds to a set of instructions for performing a function described above. The set of instructions can be executed by one or more processors (e.g., CPUs 1202). The above identified modules or programs (i.e., sets of instructions) need not be implemented as separate software programs, procedures or modules, and thus various subsets of these modules may be combined or otherwise re-arranged in various embodiments. The actual number of processors and software modules used to implement Host 101 and how features are allocated among them will vary from one implementation to another. In some embodiments, Memory 1210 may store a subset of the modules and data structures identified above. Furthermore, Memory 1210 may store additional modules and data structures not described above.

Note that method 500 described above is optionally governed by instructions that are stored in a non-transitory computer readable storage medium and that are executed by one or more processors of Device 102 or Host 101. As noted above, in some embodiments these methods may be performed in part on Device 102 and in part on Host 101, or on a single integrated system which performs all the necessary operations. Each of the operations shown in FIGS. 5A-5I optionally correspond to instructions stored in a computer memory or computer readable storage medium of Device 102 or Host 101. The computer readable storage medium optionally includes a magnetic or optical disk storage device, solid state storage devices such as Flash memory, or other non-volatile memory device or devices. In some embodiments, the computer readable instructions stored on the computer readable storage medium are in source code, assembly language code, object code, or other instruction format that is interpreted or executed by one or more processors.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method comprising:
   at a processing apparatus having one or more processors and memory storing one or more programs that, when executed by the one or more processors, cause the respective processing apparatus to perform the method:
   receiving sensor measurements generated by one or more sensors of one or more devices;
   pre-classifying the sensor measurements as belonging to one of a plurality of pre-classifications;
   selecting one or more feature types to extract from the sensor measurements based at least in part on the pre-classification of the sensor measurements, including:
      in accordance with a determination that the sensor measurements correspond to a first pre-classification, selecting a first set of feature types as the one or more selected feature types; and
      in accordance with a determination that the set of sensor measurements correspond to a second pre-classification, selecting a second set of feature types as the one or more selected feature types, wherein the first set of feature types is different from the second set of feature types;
   extracting features of the one or more selected feature types from the sensor measurements, including:
      in accordance with a determination that the sensor measurements correspond to the first pre-classification, forgoing extracting features of one or more of the second set of feature types while extracting features of the first set of feature types; and
      in accordance with a determination that the set of sensor measurements correspond to the second pre-classification, forgoing extracting features of one or more of the first set of feature types while extracting features of the second set of feature types; and
   determining a state of a respective device of the one or more devices in accordance with a classification of the sensor measurements determined based on the one or more features extracted from the sensor measurements.

2. The method of claim 1, wherein the state of the respective device comprises one or more of:
   a physical property of the respective device;
   a state of an environment of the respective device; and
   a state of an entity associated with the respective device.

3. The method of claim 1, wherein:
   pre-classifying the sensor measurements includes identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions;
   extracting the features includes extracting the first set of features and extracting the second set of features; and
   determining the state of the respective device includes determining the state of the respective device in accordance with the first set of features and the second set of features.

4. The method of claim 1, wherein:
   pre-classifying the sensor measurements includes identifying the sensor measurements as belonging to one of a plurality of coupling pre-classifications; and
   determining the state of the respective device includes determining a coupling state of the respective device in accordance with a coupling classification of the sensor measurements determined based on the one or more features extracted from the sensor measurements.

5. The method of claim 4, wherein the coupling state of the respective device is selected from a set consisting of:
   a plurality of coupling-stable states corresponding to a coupling between the respective device and an entity associated with the respective device; and a plurality of coupling-transition states corresponding to a transition between two of the coupling-stable states.

6. The method of claim 1, wherein:
the first set of feature types includes features adapted for determining a state of the respective device while the respective device is stationary; and
the second set of feature types includes features adapted for determining a state of the respective device while the respective device is in motion.

7. The method of claim 1, wherein the first set of feature types are feature types that enable classification of a coupling state of the respective device.

8. The method of claim 1, wherein the second set of feature types are feature types that enable classification of a transition between two different coupling states of the respective device.

9. The method of claim 1, wherein the first set of feature types and the second set of feature types are mutually exclusive.

10. The method of claim 1, wherein the plurality of pre-classifications include:
a first pre-classification corresponding to a plurality of transition feature types associated with identifying a transition between two different states of the respective device;
a second pre-classification corresponding to a first subset of a plurality of device-state feature types associated with identifying a state of the respective device; and
a third pre-classification corresponding to a second subset of the plurality of device-state feature types, wherein the second subset of device-state feature types is different from the first subset of device-state feature types.

11. The method of claim 1, wherein:
the method includes obtaining context information indicative of a current context of the respective device; and
the sensor measurements are pre-classified based at least in part on the current context of the respective device.

12. The method of claim 1, wherein:
pre-classifying the sensor measurements includes extracting features of one or more pre-classification feature types from the sensor measurements; and
extracting features of the pre-classification feature types from the sensor measurements is more resource efficient than extracting features of the one or more selected feature types from the sensor measurements.

13. The method of claim 1, wherein:
the one or more selected feature types includes a respective feature type that provides an approximation of frequency bandwidth information for a respective sensor-measurement signal that corresponds to sensor measurements collected over time; and
extracting features of the one or more selected feature types from the sensor measurements includes extracting features of the respective feature type from the respective sensor-measurement signal in the time domain without converting the respective sensor-measurement signal into the frequency-domain.

14. The method of claim 1, wherein:
determining the state of the respective device includes updating a Markov model, wherein the Markov model includes:
a plurality of model states corresponding to states of the respective device; and
a plurality of sets of transition probabilities between the plurality of model states;
in accordance with a determination that the sensor measurements correspond to a first pre-classification, updating one or more model states in the Markov model in accordance with a first set of transition probabilities; and
in accordance with a determination that the set of sensor measurements correspond to a second pre-classification, updating one or more model states in the Markov model in accordance with a second set of transition probabilities different from the first set of transition probabilities.

15. The method of claim 1, wherein the receiving sensor measurements, pre-classifying sensor measurements, selecting one or more feature types, extracting features and determining the state of the respective device are repeated for a plurality of measurement epochs.

16. The method of claim 15, wherein a state of the respective device determined in a prior measurement epoch is used as a factor in determining a state in a current measurement epoch.

17. The method of claim 15, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

18. The method of claim 15, wherein:
the plurality of epochs include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

19. The method of claim 1, further comprising, after determining the state of the respective device, adjusting operation of the respective device in accordance with the determined state of the respective device.

20. The method of claim 1, wherein:
the one or more devices include a first device and a second device; and
the method comprises:
determining a state of the first device in accordance with a classification of the sensor measurements determined based on the one or more features extracted from the sensor measurements; and
determining a state of the second device in accordance with the classification of the sensor measurements determined based on the one or more features extracted from the sensor measurements.

21. The method of claim 1, further comprising, prior to extracting features of the one or more feature types selected based on the pre-classification:
scheduling extraction of features of a first subset of a plurality of feature types, wherein the first subset of feature types includes the one or more feature types selected based on the pre-classification; and
scheduling extraction of features of a second subset of the plurality of feature types, wherein:

the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation.

22. The method of claim 1, further comprising:
extracting features of a first subset of a plurality of feature types, wherein the first subset includes the one or more feature types selected based on the pre-classification; and
after extracting the features of the first subset:
determining whether the features extracted from the first subset of feature types are consistent with the pre-classification;
in accordance with a determination that the features extracted from the first subset of feature types are not consistent with the pre-classification, extracting features of a second subset of feature types that includes feature types other than the one or more feature types selected based on the pre-classification; and
in accordance with a determination that the features extracted from the first subset of feature types are consistent with the pre-classification, forgoing extracting features of the second subset of feature types.

23. The method of claim 22, further comprising, prior to extracting the features of the first subset of the plurality of feature types:
scheduling extraction of features of the first subset of feature types; and
scheduling extraction of features of the second subset of feature types.

24. A processing apparatus, comprising:
one or more processors;
a set of one or more sensors;
memory; and
one or more programs, wherein the one or more programs are stored in the memory and configured to be executed by the one or more processors, the one or more programs including instructions for:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements, including:
in accordance with a determination that the sensor measurements correspond to a first pre-classification, selecting a first set of feature types as the one or more selected feature types; and
in accordance with a determination that the set of sensor measurements correspond to a second pre-classification, selecting a second set of feature types as the one or more selected feature types, wherein the first set of feature types is different from the second set of feature types;
extracting features of the one or more selected feature types from the sensor measurements, including:
in accordance with a determination that the sensor measurements correspond to the first pre-classification, forgoing extracting features of one or more of the second set of feature types while extracting features of the first set of feature types; and
in accordance with a determination that the set of sensor measurements correspond to the second pre-classification, forgoing extracting features of one or more of the first set of feature types while extracting features of the second set of feature types; and
determining a state of a respective device of the one or more devices in accordance with a classification of the sensor measurements determined based on the one or more features extracted from the sensor measurements.

25. The processing apparatus of claim 24, wherein the state of the respective device comprises one or more of:
a physical property of the respective device;
a state of an environment of the respective device; and
a state of an entity associated with the respective device.

26. The processing apparatus of claim 24, wherein:
pre-classifying the sensor measurements includes identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions;
extracting the features includes extracting the first set of features and extracting the second set of features; and
determining the state of the respective device includes determining the state of the respective device in accordance with the first set of features and the second set of features.

27. The processing apparatus of claim 24, wherein:
pre-classifying the sensor measurements includes identifying the sensor measurements as belonging to one of a plurality of coupling pre-classifications; and
determining the state of the respective device includes determining a coupling state of the respective device in accordance with a coupling classification of the sensor measurements determined based on the one or more features extracted from the sensor measurements.

28. The processing apparatus of claim 27, wherein the coupling state of the respective device is selected from a set consisting of:
a plurality of coupling-stable states corresponding to a coupling between the respective device and an entity associated with the respective device; and
a plurality of coupling-transition states corresponding to a transition between two of the coupling-stable states.

29. The processing apparatus of claim 24, wherein:
the first set of feature types includes features adapted for determining a state of the respective device while the respective device is stationary; and
the second set of feature types includes features adapted for determining a state of the respective device while the respective device is in motion.

30. The processing apparatus of claim 24, wherein the first set of feature types are feature types that enable classification of a coupling state of the respective device.

31. The processing apparatus of claim 24, wherein the second set of feature types are feature types that enable classification of a transition between two different coupling states of the respective device.

32. The processing apparatus of claim 24, wherein the first set of feature types and the second set of feature types are mutually exclusive.

33. The processing apparatus of claim 24, wherein the plurality of pre-classifications include:
- a first pre-classification corresponding to a plurality of transition feature types associated with identifying a transition between two different states of the respective device;
- a second pre-classification corresponding to a first subset of a plurality of device-state feature types associated with identifying a state of the respective device; and
- a third pre-classification corresponding to a second subset of the plurality of device-state feature types, wherein the second subset of device-state feature types is different from the first subset of device-state feature types.

34. The processing apparatus of claim 24, wherein:
the one or more programs include instructions for obtaining context information indicative of a current context of the respective device; and
the sensor measurements are pre-classified based at least in part on the current context of the respective device.

35. The processing apparatus of claim 24, wherein:
pre-classifying the sensor measurements includes extracting features of one or more pre-classification feature types from the sensor measurements; and
extracting features of the pre-classification feature types from the sensor measurements is more resource efficient than extracting features of the one or more selected feature types from the sensor measurements.

36. The processing apparatus of claim 24, wherein:
the one or more selected feature types includes a respective feature type that provides an approximation of frequency bandwidth information for a respective sensor-measurement signal that corresponds to sensor measurements collected over time; and
extracting features of the one or more selected feature types from the sensor measurements includes extracting features of the respective feature type from the respective sensor-measurement signal in the time domain without converting the respective sensor-measurement signal into the frequency-domain.

37. The processing apparatus of claim 24, wherein:
determining the state of the respective device includes updating a Markov model, wherein the Markov model includes:
- a plurality of model states corresponding to states of the respective device; and
- a plurality of sets of transition probabilities between the plurality of model states;

in accordance with a determination that the sensor measurements correspond to a first pre-classification, updating one or more model states in the Markov model in accordance with a first set of transition probabilities; and
in accordance with a determination that the set of sensor measurements correspond to a second pre-classification, updating one or more model states in the Markov model in accordance with a second set of transition probabilities different from the first set of transition probabilities.

38. The processing apparatus of claim 24, wherein the receiving sensor measurements, pre-classifying sensor measurements, selecting one or more feature types, extracting features and determining the state of the respective device are repeated for a plurality of measurement epochs.

39. The processing apparatus of claim 38, wherein a state of the respective device determined in a prior measurement epoch is used as a factor in determining a state in a current measurement epoch.

40. The processing apparatus of claim 38, wherein a frequency of the measurement epochs is variable and is determined at least in part based on one or more of:
- a coupling pre-classification of the sensor measurements;
- a probability of a coupling state of the respective device determined in a prior measurement epoch; and
- a stability of a current coupling state of the respective device.

41. The processing apparatus of claim 38, wherein:
the plurality of epochs include a first epoch and a second epoch;
during the first epoch:
- the sensor measurements are determined to correspond to a coupling-stable pre-classification; and
- a first set of feature types corresponding to the coupling-stable pre-classification are selected as the one or more selected feature types; and during the second epoch:
- the sensor measurements are determined to correspond to a coupling-transition pre-classification; and
- a second set of feature types corresponding to the coupling-transition pre-classification are selected as the one or more selected feature types, wherein the first set of feature types is different from the second set of feature types.

42. The processing apparatus of claim 24, wherein the one or more programs include instructions for, after determining the state of the respective device, adjusting operation of the respective device in accordance with the determined state of the respective device.

43. The processing apparatus of claim 24, wherein:
the one or more devices include a first device and a second device; and
the one or more programs include instructions for:
- determining a state of the first device in accordance with a classification of the sensor measurements determined based on the one or more features extracted from the sensor measurements; and
- determining a state of the second device in accordance with the classification of the sensor measurements determined based on the one or more features extracted from the sensor measurements.

44. The processing apparatus of claim 24, wherein the one or more programs include instructions for, prior to extracting features of the one or more feature types selected based on the pre-classification:
scheduling extraction of features of a first subset of a plurality of feature types, wherein the first subset of feature types includes the one or more feature types selected based on the pre-classification; and
scheduling extraction of features of a second subset of the plurality of feature types, wherein:
- the second subset of feature types includes feature types other than the one or more feature types selected based on the pre-classification;
- the extraction of features of the second subset of feature types is scheduled to occur after the extraction of features of the first subset of feature types; and
- the extraction of features of the second subset of feature types is subject to cancellation.

45. The processing apparatus of claim 24, wherein the one or more programs include instructions for:
extracting features of a first subset of a plurality of feature types, wherein the first subset includes the one or more feature types selected based on the pre-classification; and after extracting the features of the first subset:
  determining whether the features extracted from the first subset of feature types are consistent with the pre-classification;
  in accordance with a determination that the features extracted from the first subset of feature types are not consistent with the pre-classification, extracting features of a second subset of feature types that includes feature types other than the one or more feature types selected based on the pre-classification; and
  in accordance with a determination that the features extracted from the first subset of feature types are consistent with the pre-classification, forgoing extracting features of the second subset of feature types.

46. The processing apparatus of claim 45, wherein the one or more programs include instructions for, prior to extracting the features of the first subset of the plurality of feature types:
  scheduling extraction of features of the first subset of feature types; and
  scheduling extraction of features of the second subset of feature types.

47. A non-transitory computer readable storage medium storing one or more programs, the one or more programs comprising instructions, which when executed by a processing apparatus with one or more processors, cause the processing apparatus to:
  receive sensor measurements generated by one or more sensors of one or more devices;
  pre-classify the sensor measurements as belonging to one of a plurality of pre-classifications;
  select one or more feature types to extract from the sensor measurements based at least in part on the pre-classification of the sensor measurements, wherein the selecting includes:
    in accordance with a determination that the sensor measurements correspond to a first pre-classification, selecting a first set of feature types as the one or more selected feature types; and
    in accordance with a determination that the set of sensor measurements correspond to a second pre-classification, selecting a second set of feature types as the one or more selected feature types, wherein the first set of feature types is different from the second set of feature types;
  extract features of the one or more selected feature types from the sensor measurements, wherein the extracting includes:
    in accordance with a determination that the sensor measurements correspond to the first pre-classification, forgoing extracting features of one or more of the second set of feature types while extracting features of the first set of feature types; and
    in accordance with a determination that the set of sensor measurements correspond to the second pre-classification, forgoing extracting features of one or more of the first set of feature types while extracting features of the second set of feature types; and
  determine a state of a respective device of the one or more devices in accordance with a classification of the sensor measurements determined based on the one or more features extracted from the sensor measurements.

48. The non-transitory computer readable storage medium of claim 47, wherein the state of the respective device comprises one or more of:
  a physical property of the respective device;
  a state of an environment of the respective device; and
  a state of an entity associated with the respective device.

49. The non-transitory computer readable storage medium of claim 47, wherein:
  pre-classifying the sensor measurements includes identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions;
  extracting the features includes extracting the first set of features and extracting the second set of features; and
  determining the state of the respective device includes determining the state of the respective device in accordance with the first set of features and the second set of features.

50. The non-transitory computer readable storage medium of claim 47, wherein:
  pre-classifying the sensor measurements includes identifying the sensor measurements as belonging to one of a plurality of coupling pre-classifications; and
  determining the state of the respective device includes determining a coupling state of the respective device in accordance with a coupling classification of the sensor measurements determined based on the one or more features extracted from the sensor measurements.

51. The non-transitory computer readable storage medium of claim 50, wherein the coupling state of the respective device is selected from a set consisting of:
  a plurality of coupling-stable states corresponding to a coupling between the respective device and an entity associated with the respective device; and
  a plurality of coupling-transition states corresponding to a transition between two of the coupling-stable states.

52. The non-transitory computer readable storage medium of claim 47, wherein:
  the first set of feature types includes features adapted for determining a state of the respective device while the respective device is stationary; and
  the second set of feature types includes features adapted for determining a state of the respective device while the respective device is in motion.

53. The non-transitory computer readable storage medium of claim 47, wherein the first set of feature types are feature types that enable classification of a coupling state of the respective device.

54. The non-transitory computer readable storage medium of claim 47, wherein the second set of feature types are feature types that enable classification of a transition between two different coupling states of the respective device.

55. The non-transitory computer readable storage medium of claim 47, wherein the first set of feature types and the second set of feature types are mutually exclusive.

56. The non-transitory computer readable storage medium of claim 47, wherein the plurality of pre-classifications include:
  a first pre-classification corresponding to a plurality of transition feature types associated with identifying a transition between two different states of the respective device;
  a second pre-classification corresponding to a first subset of a plurality of device-state feature types associated with identifying a state of the respective device; and
  a third pre-classification corresponding to a second subset of the plurality of device-state feature types, wherein the second subset of device-state feature types is different from the first subset of device-state feature types.

57. The non-transitory computer readable storage medium of claim 47, wherein:
the one or more programs include instructions which, when executed, cause the processing apparatus to obtain context information indicative of a current context of the respective device; and
the sensor measurements are pre-classified based at least in part on the current context of the respective device.

58. The non-transitory computer readable storage medium of claim 47, wherein:
pre-classifying the sensor measurements includes extracting features of one or more pre-classification feature types from the sensor measurements; and
extracting features of the pre-classification feature types from the sensor measurements is more resource efficient than extracting features of the one or more selected feature types from the sensor measurements.

59. The non-transitory computer readable storage medium of claim 47, wherein:
the one or more selected feature types includes a respective feature type that provides an approximation of frequency bandwidth information for a respective sensor-measurement signal that corresponds to sensor measurements collected over time; and
extracting features of the one or more selected feature types from the sensor measurements includes extracting features of the respective feature type from the respective sensor-measurement signal in the time domain without converting the respective sensor-measurement signal into the frequency-domain.

60. The non-transitory computer readable storage medium of claim 47, wherein:
determining the state of the respective device includes updating a Markov model, wherein the Markov model includes:
a plurality of model states corresponding to states of the respective device; and
a plurality of sets of transition probabilities between the plurality of model states;
in accordance with a determination that the sensor measurements correspond to a first pre-classification, updating one or more model states in the Markov model in accordance with a first set of transition probabilities; and
in accordance with a determination that the set of sensor measurements correspond to a second pre-classification, updating one or more model states in the Markov model in accordance with a second set of transition probabilities different from the first set of transition probabilities.

61. The non-transitory computer readable storage medium of claim 47, wherein the receiving sensor measurements, pre-classifying sensor measurements, selecting one or more feature types, extracting features and determining the state of the respective device are repeated for a plurality of measurement epochs.

62. The non-transitory computer readable storage medium of claim 61, wherein a state of the respective device determined in a prior measurement epoch is used as a factor in determining a state in a current measurement epoch.

63. The non-transitory computer readable storage medium of claim 61, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

64. The non-transitory computer readable storage medium of claim 61, wherein:
the plurality of epochs include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

65. The non-transitory computer readable storage medium of claim 47, wherein the one or more programs include instructions which, when executed, cause the processing apparatus to, after determining the state of the respective device, adjust operation of the respective device in accordance with the determined state of the respective device.

66. The non-transitory computer readable storage medium of claim 47, wherein:
the one or more devices include a first device and a second device; and
the one or more programs include instructions which, when executed, cause the processing apparatus to:
determine a state of the first device in accordance with a classification of the sensor measurements determined based on the one or more features extracted from the sensor measurements; and
determine a state of the second device in accordance with the classification of the sensor measurements determined based on the one or more features extracted from the sensor measurements.

67. The non-transitory computer readable storage medium of claim 47, wherein the one or more programs include instructions which, when executed, cause the processing apparatus to, prior to extracting features of the one or more feature types selected based on the pre-classification:
schedule extraction of features of a first subset of a plurality of feature types, wherein the first subset of feature types includes the one or more feature types selected based on the pre-classification; and
schedule extraction of features of a second subset of the plurality of feature types, wherein:
the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation.

68. The non-transitory computer readable storage medium of claim 47, wherein the one or more programs include instructions which, when executed, cause the processing apparatus to:
extract features of a first subset of a plurality of feature types, wherein the first subset includes the one or more feature types selected based on the pre-classification; and after extracting the features of the first subset:
  determine whether the features extracted from the first subset of feature types are consistent with the pre-classification;
  in accordance with a determination that the features extracted from the first subset of feature types are not consistent with the pre-classification, extract features of a second subset of feature types that includes feature types other than the one or more feature types selected based on the pre-classification; and
  in accordance with a determination that the features extracted from the first subset of feature types are consistent with the pre-classification, forgo extracting features of the second subset of feature types.

69. The non-transitory computer readable storage medium of claim 47, wherein the one or more programs include instructions which, when executed, cause the processing apparatus to, prior to extracting the features of the first subset of the plurality of feature types:
  schedule extraction of features of the first subset of feature types; and
  schedule extraction of features of the second subset of feature types.

70. A method comprising:
  at a processing apparatus having one or more processors and memory storing one or more programs that, when executed by the one or more processors, cause the respective processing apparatus to perform the method:
    receiving sensor measurements generated by one or more sensors of one or more devices;
    pre-classifying the sensor measurements as belonging to one of a plurality of pre-classifications, wherein pre-classifying the sensor measurements includes identifying the sensor measurements as belonging to one of a plurality of coupling pre-classifications;
    selecting one or more feature types to extract from the sensor measurements based at least in part on the pre-classification of the sensor measurements;
    extracting features of the one or more selected feature types from the sensor measurements; and
    determining a state of a respective device of the one or more devices in accordance with a classification of the sensor measurements determined based on the one or more features extracted from the sensor measurements, wherein determining the state of the respective device includes determining a coupling state of the respective device in accordance with a coupling classification of the sensor measurements determined based on the one or more features extracted from the sensor measurements, wherein the coupling state of the respective device is selected from a set consisting of:
      a plurality of coupling-stable states corresponding to a coupling between the respective device and an entity associated with the respective device; and
      a plurality of coupling-transition states corresponding to a transition between two of the coupling-stable states.

71. The method of claim 70, wherein selecting the one or more feature types includes:
  in accordance with a determination that the sensor measurements correspond to a first pre-classification, selecting a first set of feature types as the one or more selected feature types; and
  in accordance with a determination that the set of sensor measurements correspond to a second pre-classification, selecting a second set of feature types as the one or more selected feature types, wherein the first set of feature types is different from the second set of feature types.

72. The method of claim 71, wherein the first set of feature types are feature types that enable classification of a coupling state of the respective device.

73. The method of claim 72, wherein the second set of feature types are feature types that enable classification of a transition between two different coupling states of the respective device.

74. The method of claim 70, wherein the plurality of pre-classifications include:
  a first pre-classification corresponding to a plurality of transition feature types associated with identifying a transition between two different states of the respective device;
  a second pre-classification corresponding to a first subset of a plurality of device-state feature types associated with identifying a state of the respective device; and
  a third pre-classification corresponding to a second subset of the plurality of device-state feature types, wherein the second subset of device-state feature types is different from the first subset of device-state feature types.

75. A processing apparatus, comprising:
  one or more processors;
  a set of one or more sensors;
  memory; and
  one or more programs, wherein the one or more programs are stored in the memory and configured to be executed by the one or more processors, the one or more programs including instructions for:
    receiving sensor measurements generated by one or more sensors of one or more devices;
    pre-classifying the sensor measurements as belonging to one of a plurality of pre-classifications, wherein pre-classifying the sensor measurements includes identifying the sensor measurements as belonging to one of a plurality of coupling pre-classifications;
    selecting one or more feature types to extract from the sensor measurements based at least in part on the pre-classification of the sensor measurements;
    extracting features of the one or more selected feature types from the sensor measurements; and
    determining a state of a respective device of the one or more devices in accordance with a classification of the sensor measurements determined based on the one or more features extracted from the sensor measurements, wherein determining the state of the respective device includes determining a coupling state of the respective device in accordance with a coupling classification of the sensor measurements determined based on the one or more features extracted from the sensor measurements, wherein the coupling state of the respective device is selected from a set consisting of:
      a plurality of coupling-stable states corresponding to a coupling between the respective device and an entity associated with the respective device; and
      a plurality of coupling-transition states corresponding to a transition between two of the coupling-stable states.

76. The processing apparatus of claim 75, wherein selecting the one or more feature types includes:
  in accordance with a determination that the sensor measurements correspond to a first pre-classification, selecting a first set of feature types as the one or more selected feature types; and in accordance with a determination that the set of sensor measurements correspond to a second pre-classification, selecting a second set of feature types as the one or more selected feature types, wherein the first set of feature types is different from the second set of feature types.

77. The processing apparatus of claim 76, wherein the first set of feature types are feature types that enable classification of a coupling state of the respective device.

78. The processing apparatus of claim 77, wherein the second set of feature types are feature types that enable classification of a transition between two different coupling states of the respective device.

79. The processing apparatus of claim 77, wherein the plurality of pre-classifications include:
 a first pre-classification corresponding to a plurality of transition feature types associated with identifying a transition between two different states of the respective device;
 a second pre-classification corresponding to a first subset of a plurality of device-state feature types associated with identifying a state of the respective device; and
 a third pre-classification corresponding to a second subset of the plurality of device-state feature types, wherein the second subset of device-state feature types is different from the first subset of device-state feature types.

80. A non-transitory computer readable storage medium storing one or more programs, the one or more programs comprising instructions, which when executed by a processing apparatus with one or more processors, cause the processing apparatus to:
 receiving sensor measurements generated by one or more sensors of one or more devices;
 pre-classifying the sensor measurements as belonging to one of a plurality of pre-classifications, wherein pre-classifying the sensor measurements includes identifying the sensor measurements as belonging to one of a plurality of coupling pre-classifications;
 selecting one or more feature types to extract from the sensor measurements based at least in part on the pre-classification of the sensor measurements;
 extracting features of the one or more selected feature types from the sensor measurements; and
 determining a state of a respective device of the one or more devices in accordance with a classification of the sensor measurements determined based on the one or more features extracted from the sensor measurements, wherein determining the state of the respective device includes determining a coupling state of the respective device in accordance with a coupling classification of the sensor measurements determined based on the one or more features extracted from the sensor measurements, wherein the coupling state of the respective device is selected from a set consisting of:
  a plurality of coupling-stable states corresponding to a coupling between the respective device and an entity associated with the respective device; and
  a plurality of coupling-transition states corresponding to a transition between two of the coupling-stable states.

81. The non-transitory computer readable storage medium of claim 80, wherein selecting the one or more feature types includes:
 in accordance with a determination that the sensor measurements correspond to a first pre-classification, selecting a first set of feature types as the one or more selected feature types; and
 in accordance with a determination that the set of sensor measurements correspond to a second pre-classification, selecting a second set of feature types as the one or more selected feature types, wherein the first set of feature types is different from the second set of feature types.

82. The non-transitory computer readable storage medium of claim 81, wherein the first set of feature types are feature types that enable classification of a coupling state of the respective device.

83. The non-transitory computer readable storage medium of claim 82, wherein the second set of feature types are feature types that enable classification of a transition between two different coupling states of the respective device.

84. The non-transitory computer readable storage medium of claim 82, wherein the plurality of pre-classifications include:
 a first pre-classification corresponding to a plurality of transition feature types associated with identifying a transition between two different states of the respective device;
 a second pre-classification corresponding to a first subset of a plurality of device-state feature types associated with identifying a state of the respective device; and
 a third pre-classification corresponding to a second subset of the plurality of device-state feature types, wherein the second subset of device-state feature types is different from the first subset of device-state feature types.

85. A method comprising:
 at a processing apparatus having one or more processors and memory storing one or more programs that, when executed by the one or more processors, cause the respective processing apparatus to perform the method:
  receiving sensor measurements generated by one or more sensors of one or more devices;
  pre-classifying the sensor measurements as belonging to one of a plurality of pre-classifications, wherein pre-classifying the sensor measurements includes extracting features of one or more pre-classification feature types from the sensor measurements;
  selecting one or more feature types to extract from the sensor measurements based at least in part on the pre-classification of the sensor measurements;
  extracting features of the one or more selected feature types from the sensor measurements, wherein extracting features of the pre-classification feature types from the sensor measurements is more resource efficient than extracting features of the one or more selected feature types from the sensor measurements; and
  determining a state of a respective device of the one or more devices in accordance with a classification of the sensor measurements determined based on the one or more features extracted from the sensor measurements.

86. The method of claim 85, wherein:
 pre-classifying the sensor measurements includes identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions;
 extracting the features includes extracting the first set of features and extracting the second set of features; and
 determining the state of the respective device includes determining the state of the respective device in accordance with the first set of features and the second set of features.

87. The method of claim 85, wherein:
pre-classifying the sensor measurements includes identifying the sensor measurements as belonging to one of a plurality of coupling pre-classifications; and
determining the state of the respective device includes determining a coupling state of the respective device in accordance with a coupling classification of the sensor measurements determined based on the one or more features extracted from the sensor measurements.

88. The method of claim 85, further comprising, prior to extracting features of the one or more feature types selected based on the pre-classification:
scheduling extraction of features of a first subset of a plurality of feature types, wherein the first subset of feature types includes the one or more feature types selected based on the pre-classification; and
scheduling extraction of features of a second subset of the plurality of feature types, wherein:
the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation.

89. The method of claim 85, further comprising:
extracting features of a first subset of a plurality of feature types, wherein the first subset includes the one or more feature types selected based on the pre-classification; and
after extracting the features of the first subset:
determining whether the features extracted from the first subset of feature types are consistent with the pre-classification;
in accordance with a determination that the features extracted from the first subset of feature types are not consistent with the pre-classification, extracting features of a second subset of feature types that includes feature types other than the one or more feature types selected based on the pre-classification; and
in accordance with a determination that the features extracted from the first subset of feature types are consistent with the pre-classification, forgoing extracting features of the second subset of feature types.

90. A processing apparatus, comprising:
one or more processors;
a set of one or more sensors;
memory; and
one or more programs, wherein the one or more programs are stored in the memory and configured to be executed by the one or more processors, the one or more programs including instructions for:
receiving sensor measurements generated by one or more sensors of one or more devices;
pre-classifying the sensor measurements as belonging to one of a plurality of pre-classifications, wherein pre-classifying the sensor measurements includes extracting features of one or more pre-classification feature types from the sensor measurements;
selecting one or more feature types to extract from the sensor measurements based at least in part on the pre-classification of the sensor measurements;
extracting features of the one or more selected feature types from the sensor measurements, wherein extracting features of the pre-classification feature types from the sensor measurements is more resource efficient than extracting features of the one or more selected feature types from the sensor measurements; and
determining a state of a respective device of the one or more devices in accordance with a classification of the sensor measurements determined based on the one or more features extracted from the sensor measurements.

91. The processing apparatus of claim 90, wherein:
pre-classifying the sensor measurements includes identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions;
extracting the features includes extracting the first set of features and extracting the second set of features; and
determining the state of the respective device includes determining the state of the respective device in accordance with the first set of features and the second set of features.

92. The processing apparatus of claim 90, wherein:
pre-classifying the sensor measurements includes identifying the sensor measurements as belonging to one of a plurality of coupling pre-classifications; and
determining the state of the respective device includes determining a coupling state of the respective device in accordance with a coupling classification of the sensor measurements determined based on the one or more features extracted from the sensor measurements.

93. The processing apparatus of claim 90, wherein the one or more programs include instructions for, prior to extracting features of the one or more feature types selected based on the pre-classification:
scheduling extraction of features of a first subset of a plurality of feature types, wherein the first subset of feature types includes the one or more feature types selected based on the pre-classification; and
scheduling extraction of features of a second subset of the plurality of feature types, wherein:
the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation.

94. The processing apparatus of claim 90, wherein the one or more programs include instructions for:
extracting features of a first subset of a plurality of feature types, wherein the first subset includes the one or more feature types selected based on the pre-classification; and
after extracting the features of the first subset:
determining whether the features extracted from the first subset of feature types are consistent with the pre-classification;
in accordance with a determination that the features extracted from the first subset of feature types are not consistent with the pre-classification, extracting features of a second subset of feature types that includes feature types other than the one or more feature types selected based on the pre-classification; and in accordance with a determination that the features extracted from the first subset of feature types are consistent with the pre-classification, forgoing extracting features of the second subset of feature types.

95. A non-transitory computer readable storage medium storing one or more programs, the one or more programs comprising instructions, which when executed by a processing apparatus with one or more processors, cause the processing apparatus to:
receive sensor measurements generated by one or more sensors of one or more devices;
pre-classify the sensor measurements as belonging to one of a plurality of pre-classifications, wherein pre-classifying the sensor measurements includes extracting features of one or more pre-classification feature types from the sensor measurements;
select one or more feature types to extract from the sensor measurements based at least in part on the pre-classification of the sensor measurements;
extract features of the one or more selected feature types from the sensor measurements, wherein extracting features of the pre-classification feature types from the sensor measurements is more resource efficient than extracting features of the one or more selected feature types from the sensor measurements; and
determine a state of a respective device of the one or more devices in accordance with a classification of the sensor measurements determined based on the one or more features extracted from the sensor measurements.

96. The non-transitory computer readable storage medium of claim 95, wherein:
pre-classifying the sensor measurements includes identifying the sensor measurements as belonging to a respective pre-classification that is associated with multiple feature sets, including a first set of features for use in identifying states of the respective device under a first set of conditions and a second set of features for use in identifying states of the respective device under a second set of conditions different from the first set of conditions;
extracting the features includes extracting the first set of features and extracting the second set of features; and
determining the state of the respective device includes determining the state of the respective device in accordance with the first set of features and the second set of features.

97. The non-transitory computer readable storage medium of claim 95, wherein:
pre-classifying the sensor measurements includes identifying the sensor measurements as belonging to one of a plurality of coupling pre-classifications; and
determining the state of the respective device includes determining a coupling state of the respective device in accordance with a coupling classification of the sensor measurements determined based on the one or more features extracted from the sensor measurements.

98. The non-transitory computer readable storage medium of claim 95, wherein the one or more programs include instructions which, when executed, cause the processing apparatus to, prior to extracting features of the one or more feature types selected based on the pre-classification:
schedule extraction of features of a first subset of a plurality of feature types, wherein the first subset of feature types includes the one or more feature types selected based on the pre-classification; and
schedule extraction of features of a second subset of the plurality of feature types, wherein:
the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation.

99. The non-transitory computer readable storage medium of claim 95, wherein the one or more programs include instructions which, when executed, cause the processing apparatus to:
extract features of a first subset of a plurality of feature types, wherein the first subset includes the one or more feature types selected based on the pre-classification; and
after extracting the features of the first subset:
determine whether the features extracted from the first subset of feature types are consistent with the pre-classification;
in accordance with a determination that the features extracted from the first subset of feature types are not consistent with the pre-classification, extract features of a second subset of feature types that includes feature types other than the one or more feature types selected based on the pre-classification; and
in accordance with a determination that the features extracted from the first subset of feature types are consistent with the pre-classification, forgo extracting features of the second subset of feature types.

100. A method comprising:
at a processing apparatus having one or more processors and memory storing one or more programs that, when executed by the one or more processors, cause the respective processing apparatus to perform the method:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
extracting features of the one or more selected feature types from the sensor measurements;
determining a state of a respective device of the one or more devices in accordance with a classification of the sensor measurements determined based on the one or more features extracted from the sensor measurements, wherein determining the state of the respective device includes updating a Markov model, wherein:
the Markov model includes a plurality of model states corresponding to states of the respective device and a plurality of sets of transition probabilities between the plurality of model states; and
updating the Markov model includes:
in accordance with a determination that the sensor measurements correspond to a first pre-classification, updating one or more model states in the Markov model in accordance with a first set of transition probabilities; and
in accordance with a determination that the set of sensor measurements correspond to a second pre-classification, updating one or more model states in the Markov model in accordance with a second set of transition probabilities different from the first set of transition probabilities.

101. The method of claim 100, wherein the receiving sensor measurements, pre-classifying sensor measurements, selecting one or more feature types, extracting features and determining the state of the respective device are repeated for a plurality of measurement epochs.

102. The method of claim 101, wherein a state of the respective device determined in a prior measurement epoch is used as a factor in determining a state in a current measurement epoch.

103. The method of claim 101, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

104. The method of claim 101, wherein:
the plurality of epochs include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

105. A processing apparatus, comprising:
one or more processors;
a set of one or more sensors;
memory; and
one or more programs, wherein the one or more programs are stored in the memory and configured to be executed by the one or more processors, the one or more programs including instructions for:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
extracting features of the one or more selected feature types from the sensor measurements;
determining a state of a respective device of the one or more devices in accordance with a classification of the sensor measurements determined based on the one or more features extracted from the sensor measurements, wherein determining the state of the respective device includes updating a Markov model, wherein:
the Markov model includes a plurality of model states corresponding to states of the respective device and a plurality of sets of transition probabilities between the plurality of model states; and
updating the Markov model includes:
in accordance with a determination that the sensor measurements correspond to a first pre-classification, updating one or more model states in the Markov model in accordance with a first set of transition probabilities; and
in accordance with a determination that the set of sensor measurements correspond to a second pre-classification, updating one or more model states in the Markov model in accordance with a second set of transition probabilities different from the first set of transition probabilities.

106. The processing apparatus of claim 105, wherein the receiving sensor measurements, pre-classifying sensor measurements, selecting one or more feature types, extracting features and determining the state of the respective device are repeated for a plurality of measurement epochs.

107. The processing apparatus of claim 106, wherein a state of the respective device determined in a prior measurement epoch is used as a factor in determining a state in a current measurement epoch.

108. The processing apparatus of claim 106, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

109. The processing apparatus of claim 106, wherein:
the plurality of epochs include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

110. A non-transitory computer readable storage medium storing one or more programs, the one or more programs comprising instructions, which when executed by a processing apparatus with one or more processors, cause the processing apparatus to:
receive sensor measurements generated by one or more sensors of one or more devices;
pre-classify the sensor measurements as belonging to one of a plurality of pre-classifications;
select one or more feature types to extract from the sensor measurements based at least in part on the pre-classification of the sensor measurements;
extract features of the one or more selected feature types from the sensor measurements;
determine a state of a respective device of the one or more devices in accordance with a classification of the sensor measurements determined based on the one or more features extracted from the sensor measurements, wherein determining the state of the respective device includes updating a Markov model, wherein:
the Markov model includes a plurality of model states corresponding to states of the respective device and a plurality of sets of transition probabilities between the plurality of model states; and
updating the Markov model includes:
in accordance with a determination that the sensor measurements correspond to a first pre-classification, updating one or more model states in the Markov model in accordance with a first set of transition probabilities; and in accordance with a determination that the set of sensor measurements correspond to a second pre-classification, updating one or more model states in the Markov model in accordance with a second set of transition probabilities different from the first set of transition probabilities.

111. The non-transitory computer readable storage medium of claim 110, wherein the receiving sensor measurements, pre-classifying sensor measurements, selecting one or more feature types, extracting features and determining the state of the respective device are repeated for a plurality of measurement epochs.

112. The non-transitory computer readable storage medium of claim 111, wherein a state of the respective device determined in a prior measurement epoch is used as a factor in determining a state in a current measurement epoch.

113. The non-transitory computer readable storage medium of claim 111, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

114. The non-transitory computer readable storage medium of claim 111, wherein:
the plurality of epochs include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

115. A method comprising:
at a processing apparatus having one or more processors and memory storing one or more programs that, when executed by the one or more processors, cause the respective processing apparatus to perform the method:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
extracting features of the one or more selected feature types from the sensor measurements;
determining a state of a respective device of the one or more devices in accordance with a classification of the sensor measurements determined based on the one or more features extracted from the sensor measurements; and wherein:
the receiving sensor measurements, pre-classifying sensor measurements, selecting one or more feature types, extracting features and determining the state of the respective device are repeated for a plurality of measurement epochs that include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

116. The method of claim 115, wherein:
the first set of feature types includes features adapted for determining a state of the respective device while the respective device is stationary; and
the second set of feature types includes features adapted for determining a state of the respective device while the respective device is in motion.

117. The method of claim 115, wherein the first set of feature types are feature types that enable classification of a coupling state of the respective device.

118. The method of claim 117, wherein the second set of feature types are feature types that enable classification of a transition between two different coupling states of the respective device.

119. The method of claim 115, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

120. A processing apparatus, comprising:
one or more processors;
a set of one or more sensors;
memory; and
one or more programs, wherein the one or more programs are stored in the memory and configured to be executed by the one or more processors, the one or more programs including instructions for:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
extracting features of the one or more selected feature types from the sensor measurements;
determining a state of a respective device of the one or more devices in accordance with a classification of the sensor measurements determined based on the one or more features extracted from the sensor measurements; and wherein:
the receiving sensor measurements, pre-classifying sensor measurements, selecting one or more feature types, extracting features and determining the state of the respective device are repeated for a plurality of measurement epochs that include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

121. The processing apparatus of claim 120, wherein:
the first set of feature types includes features adapted for determining a state of the respective device while the respective device is stationary; and
the second set of feature types includes features adapted for determining a state of the respective device while the respective device is in motion.

122. The processing apparatus of claim 120, wherein the first set of feature types are feature types that enable classification of a coupling state of the respective device.

123. The processing apparatus of claim 122, wherein the second set of feature types are feature types that enable classification of a transition between two different coupling states of the respective device.

124. The processing apparatus of claim 120, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

125. A non-transitory computer readable storage medium storing one or more programs, the one or more programs comprising instructions, which when executed by a processing apparatus with one or more processors, cause the processing apparatus to:
receive sensor measurements generated by one or more sensors of one or more devices;
pre-classify the sensor measurements as belonging to one of a plurality of pre-classifications;
select one or more feature types to extract from the sensor measurements based at least in part on the pre-classification of the sensor measurements;
extract features of the one or more selected feature types from the sensor measurements;
determine a state of a respective device of the one or more devices in accordance with a classification of the sensor measurements determined based on the one or more features extracted from the sensor measurements; and
wherein:
the receiving sensor measurements, pre-classifying sensor measurements, selecting one or more feature types, extracting features and determining the state of the respective device are repeated for a plurality of measurement epochs that include a first epoch and a second epoch;
during the first epoch:
the sensor measurements are determined to correspond to a coupling-stable pre-classification; and
a first set of feature types corresponding to the coupling-stable pre-classification are selected as the one or more selected feature types; and
during the second epoch:
the sensor measurements are determined to correspond to a coupling-transition pre-classification; and
a second set of feature types corresponding to the coupling-transition pre-classification are selected as the one or more selected feature types, wherein the first set of feature types is different from the second set of feature types.

126. The non-transitory computer readable storage medium of claim 125, wherein:
the first set of feature types includes features adapted for determining a state of the respective device while the respective device is stationary; and
the second set of feature types includes features adapted for determining a state of the respective device while the respective device is in motion.

127. The non-transitory computer readable storage medium of claim 125, wherein the first set of feature types are feature types that enable classification of a coupling state of the respective device.

128. The non-transitory computer readable storage medium of claim 127, wherein the second set of feature types are feature types that enable classification of a transition between two different coupling states of the respective device.

129. The non-transitory computer readable storage medium of claim 125, wherein a frequency of the measurement epochs is variable and is determined at least in part based on one or more of:
a coupling pre-classification of the sensor measurements;
a probability of a coupling state of the respective device determined in a prior measurement epoch; and
a stability of a current coupling state of the respective device.

130. A method comprising:
at a processing apparatus having one or more processors and memory storing one or more programs that, when executed by the one or more processors, cause the respective processing apparatus to perform the method:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
scheduling extraction of features of a first subset of a plurality of feature types, wherein the first subset of feature types includes the one or more feature types selected based on the pre-classification; and
scheduling extraction of features of a second subset of the plurality of feature types, wherein:
the second subset of feature types includes feature types other than the one or more feature types selected based on the pre-classification;

the extraction of features of the second subset of feature types is scheduled to occur after the extraction of features of the first subset of feature types; and
the extraction of features of the second subset of feature types is subject to cancellation;
extracting features of the one or more selected feature types from the sensor measurements; and
determining a state of a respective device of the one or more devices in accordance with a classification of the sensor measurements determined based on the one or more features extracted from the sensor measurements.

131. The method of claim 130, wherein:
the first subset of feature types includes features adapted for determining a state of the respective device while the respective device is stationary; and
the second subset of feature types includes features adapted for determining a state of the respective device while the respective device is in motion.

132. The method of claim 130, wherein the first subset of feature types are feature types that enable classification of a coupling state of the respective device.

133. The method of claim 132, wherein the second subset of feature types are feature types that enable classification of a transition between two different coupling states of the respective device.

134. The method of claim 130, wherein the first subset of feature types and the second subset of feature types are mutually exclusive.

135. A processing apparatus, comprising:
one or more processors;
a set of one or more sensors;
memory; and
one or more programs, wherein the one or more programs are stored in the memory and configured to be executed by the one or more processors, the one or more programs including instructions for:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
scheduling extraction of features of a first subset of a plurality of feature types, wherein the first subset of feature types includes the one or more feature types selected based on the pre-classification; and
scheduling extraction of features of a second subset of the plurality of feature types, wherein:
the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation;
extracting features of the one or more selected feature types from the sensor measurements; and
determining a state of a respective device of the one or more devices in accordance with a classification of the sensor measurements determined based on the one or more features extracted from the sensor measurements.

136. The processing apparatus of claim 135, wherein:
the first subset of feature types includes features adapted for determining a state of the respective device while the respective device is stationary; and
the second subset of feature types includes features adapted for determining a state of the respective device while the respective device is in motion.

137. The processing apparatus of claim 135, wherein the first subset of feature types are feature types that enable classification of a coupling state of the respective device.

138. The processing apparatus of claim 137, wherein the second subset of feature types are feature types that enable classification of a transition between two different coupling states of the respective device.

139. The processing apparatus of claim 135, wherein the first subset of feature types and the second subset of feature types are mutually exclusive.

140. A non-transitory computer readable storage medium storing one or more programs, the one or more programs comprising instructions, which when executed by a processing apparatus with one or more processors, cause the processing apparatus to:
receive sensor measurements generated by one or more sensors of one or more devices;
pre-classify the sensor measurements as belonging to one of a plurality of pre-classifications;
select one or more feature types to extract from the sensor measurements based at least in part on the pre-classification of the sensor measurements;
schedule extraction of features of a first subset of a plurality of feature types, wherein the first subset of feature types includes the one or more feature types selected based on the pre-classification; and
schedule extraction of features of a second subset of the plurality of feature types, wherein:
the second subset of feature types includes feature types other than the one or more feature types selected based on the pre-classification;
the extraction of features of the second subset of feature types is scheduled to occur after the extraction of features of the first subset of feature types; and
the extraction of features of the second subset of feature types is subject to cancellation;
extract features of the one or more selected feature types from the sensor measurements; and
determine a state of a respective device of the one or more devices in accordance with a classification of the sensor measurements determined based on the one or more features extracted from the sensor measurements.

141. The non-transitory computer readable storage medium of claim 140, wherein:
the first subset of feature types includes features adapted for determining a state of the respective device while the respective device is stationary; and
the second subset of feature types includes features adapted for determining a state of the respective device while the respective device is in motion.

142. The non-transitory computer readable storage medium of claim 140, wherein the first subset of feature types are feature types that enable classification of a coupling state of the respective device.

143. The non-transitory computer readable storage medium of claim 142, wherein the second subset of feature types are feature types that enable classification of a transition between two different coupling states of the respective device.

144. The non-transitory computer readable storage medium of claim 140, wherein the first subset of feature types and the second subset of feature types are mutually exclusive.

145. A method comprising:
at a processing apparatus having one or more processors and memory storing one or more programs that, when executed by the one or more processors, cause the respective processing apparatus to perform the method:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
extracting features of the one or more selected feature types from the sensor measurements, wherein extracting the features of the one or more selected feature types includes extracting features of a first subset of a plurality of feature types, wherein the first subset includes the one or more feature types selected based on the pre-classification; and
after extracting the features of the first subset:
determining whether the features extracted from the first subset of feature types are consistent with the pre-classification;
in accordance with a determination that the features extracted from the first subset of feature types are not consistent with the pre-classification, extracting features of a second subset of feature types that includes feature types other than the one or more feature types selected based on the pre-classification; and
in accordance with a determination that the features extracted from the first subset of feature types are consistent with the pre-classification, forgoing extracting features of the second subset of feature types; and
determining a state of a respective device of the one or more devices in accordance with a classification of the sensor measurements determined based on the one or more features extracted from the sensor measurements.

146. The method of claim 145, wherein:
the first subset of feature types includes features adapted for determining a state of the respective device while the respective device is stationary; and
the second subset of feature types includes features adapted for determining a state of the respective device while the respective device is in motion.

147. The method of claim 145, wherein the first subset of feature types are feature types that enable classification of a coupling state of the respective device.

148. The method of claim 147, wherein the second subset of feature types are feature types that enable classification of a transition between two different coupling states of the respective device.

149. The method of claim 145, further comprising, prior to extracting the features of the first subset of the plurality of feature types:
scheduling extraction of features of the first subset of feature types; and
scheduling extraction of features of the second subset of feature types.

150. A processing apparatus, comprising:
one or more processors;
a set of one or more sensors;
memory; and
one or more programs, wherein the one or more programs are stored in the memory and configured to be executed by the one or more processors, the one or more programs including instructions for:
receiving sensor measurements generated by one or more sensors of one or more devices;
pre-classifying the sensor measurements as belonging to one of a plurality of pre-classifications;
selecting one or more feature types to extract from the sensor measurements based at least in part on the pre-classification of the sensor measurements;
extracting features of the one or more selected feature types from the sensor measurements, wherein extracting the features of the one or more selected feature types includes extracting features of a first subset of a plurality of feature types, wherein the first subset includes the one or more feature types selected based on the pre-classification; and
after extracting the features of the first subset:
determining whether the features extracted from the first subset of feature types are consistent with the pre-classification;
in accordance with a determination that the features extracted from the first subset of feature types are not consistent with the pre-classification, extracting features of a second subset of feature types that includes feature types other than the one or more feature types selected based on the pre-classification; and
in accordance with a determination that the features extracted from the first subset of feature types are consistent with the pre-classification, forgoing extracting features of the second subset of feature types; and
determining a state of a respective device of the one or more devices in accordance with a classification of the sensor measurements determined based on the one or more features extracted from the sensor measurements.

151. The processing apparatus of claim 150, wherein:
the first subset of feature types includes features adapted for determining a state of the respective device while the respective device is stationary; and
the second subset of feature types includes features adapted for determining a state of the respective device while the respective device is in motion.

152. The processing apparatus of claim 150, wherein the first subset of feature types are feature types that enable classification of a coupling state of the respective device.

153. The processing apparatus of claim 152, wherein the second subset of feature types are feature types that enable classification of a transition between two different coupling states of the respective device.

154. The processing apparatus of claim 150, wherein the one or more programs include instructions for, prior to extracting the features of the first subset of the plurality of feature types:
scheduling extraction of features of the first subset of feature types; and
scheduling extraction of features of the second subset of feature types.

155. A non-transitory computer readable storage medium storing one or more programs, the one or more programs comprising instructions, which when executed by a processing apparatus with one or more processors, cause the processing apparatus to:

receive sensor measurements generated by one or more sensors of one or more devices;

pre-classify the sensor measurements as belonging to one of a plurality of pre-classifications;

select one or more feature types to extract from the sensor measurements based at least in part on the pre-classification of the sensor measurements;

extract features of the one or more selected feature types from the sensor measurements, wherein extracting the features of the one or more selected feature types includes extracting features of a first subset of a plurality of feature types, wherein the first subset includes the one or more feature types selected based on the pre-classification; and after extracting the features of the first subset:
- determine whether the features extracted from the first subset of feature types are consistent with the pre-classification;
- in accordance with a determination that the features extracted from the first subset of feature types are not consistent with the pre-classification, extract features of a second subset of feature types that includes feature types other than the one or more feature types selected based on the pre-classification; and
- in accordance with a determination that the features extracted from the first subset of feature types are consistent with the pre-classification, forgo extracting features of the second subset of feature types; and determine a state of a respective device of the one or more devices in accordance with a classification of the sensor measurements determined based on the one or more features extracted from the sensor measurements.

156. The non-transitory computer readable storage medium of claim 155, wherein:
- the first subset of feature types includes features adapted for determining a state of the respective device while the respective device is stationary; and
- the second subset of feature types includes features adapted for determining a state of the respective device while the respective device is in motion.

157. The non-transitory computer readable storage medium of claim 155, wherein the first subset of feature types are feature types that enable classification of a coupling state of the respective device.

158. The non-transitory computer readable storage medium of claim 157, wherein the second subset of feature types are feature types that enable classification of a transition between two different coupling states of the respective device.

159. The non-transitory computer readable storage medium of claim 155, wherein the one or more programs include instructions which, when executed, cause the processing apparatus to, prior to extracting the features of the first subset of the plurality of feature types:
- schedule extraction of features of the first subset of feature types; and
- schedule extraction of features of the second subset of feature types.

* * * * *